United States Patent
Warikoo et al.

(10) Patent No.: US 10,920,182 B2
(45) Date of Patent: Feb. 16, 2021

(54) AFFINITY-BASED ANALYTICAL PURIFICATION OF BIOTHERAPEUTICS FOR BIOPROCESS MONITORING

(71) Applicant: Genzyme Corporation, Cambridge, MA (US)

(72) Inventors: Veena Warikoo, Westford, MA (US); Kevin Brower, Holliston, MA (US)

(73) Assignee: GENZYME CORPORATION, Cambridge, MA (US)

( * ) Notice: Subject to any disclaimer, the term of this patent is extended or adjusted under 35 U.S.C. 154(b) by 145 days.

(21) Appl. No.: 15/831,085

(22) Filed: Dec. 4, 2017

(65) Prior Publication Data

US 2018/0155801 A1 Jun. 7, 2018

Related U.S. Application Data

(62) Division of application No. 14/214,105, filed on Mar. 14, 2014, now abandoned.

(60) Provisional application No. 61/790,676, filed on Mar. 15, 2013.

(51) Int. Cl.
| | | |
|---|---|---|
| *C12Q 3/00* | (2006.01) | |
| *G01N 33/573* | (2006.01) | |
| *C07K 1/22* | (2006.01) | |
| *C12C 3/00* | (2006.01) | |

(52) U.S. Cl.
CPC ............... *C12C 3/00* (2013.01); *C07K 1/22* (2013.01); *G01N 33/573* (2013.01)

(58) Field of Classification Search
None
See application file for complete search history.

(56) References Cited

PUBLICATIONS

Rathore AS et al. Process Analytical Technology for biopharmaceutical products. 2010. Anal Bioanal Chem. p. 1-18 (Year: 2010).*
Le Floch F et al. HPCE Monitoring of the N-glycosylation Pattern and Sialylation of Murine Erythropoietin Produced by CHO cells in Batch Processes. 2004. Biotechnol. Prog. 20, 864-871 (Year: 2004).*
Aboud et al., "A new HPLC immunoaffinity assay for intact hepatitis A virus: Applications in vaccine process levelopment", Biotechnology Techniques, 12(6):439-43 (1998).
Bareither & Pollard, "A review of advanced small-scale parallel bioreactor technology for accelerated process development: current state and future need," Biotechnol Prog. 27(1):2-14 (2011).
Berry et al., "Immobilization of Fv antibody fragments on porous silica and their utility in affinity chromatography," J Chromatogr. 587(2):161-9 (1991).
Brower et al., "Single-step affinity purification of enzyme biotherapeutics: a platform methodology for accelerated process development.", Biotechnology Progress, 30(3):708-17 (2014).
Burgess & Thompson,"Advances in gentle immunoaffinity chromatography," Curr Opin Biotechnol. 13(4):304-8 (2002).
Callis et al., "Process analytical chemistry," Analytical Chemistry 59(9):624A-637A (1987).
Chon & Zarbis-Papastoitsis, "Advances in the production and downstream processing of antibodies," N Biotechnol. 28(5):458-63 (2011).
Cooley et al., "On-line liquid chromatography as a process analytical technology for monitoring and control of biotech processes", Dionex pp. 1-4 (2006).
Grandics et al., "Integration of cell culture with continuous, on-line sterile downstream processing", Annals of the New York Academy of Sciences, 646:322-33 (1991).
Harmsen & De Haard, "Properties, production, and applications of camelid single-domain antibody fragments," Appl Microbiol Biotechnol. 77(1):13-22 (2007).
Hirschfeld et al., "Chemical sensing in process analysis," Science 226(4672):312-8 (1984).
Hossler et al., "Optimal and consistent protein glycosylation in mammalian cell culture," Glycobiology 19(9):9336-49 (2009).
International Search Report and Written Opinion for International Application No. PCT/US2014/029720, dated Sep. 3, 2014, pp. 1-14.
Kelly, "Very large scale monoclonal antibody purification: The case for conventional unit operations." Biotechnology Prog. 23(5):995-1008 (2007).
Kourti, The Process Analytical Technology initiative and multivariate process analysis, monitoring and control. Anal Bioanal Chem. 384(5):1043-8 (2006).
Kuribayashi et al., "Rapid evaluation for heterogeneities in monoclonal antibodies by liquid chromatography/mass spectrometry with a column-switching system," J Pharm Biomed Anal. 67-68:1-9 (2012).
Le Floch et al., "HPCE monitoring of the N-glycosylation pattern and sialylation of murine erythropoietin produced by CHO cells in batch processes," Biotechnol Prog. 20(3):864-71 (2004).
Liu et al., "Capillary Electrophoresis with Laser-Induced Fluorescence Detection as a Tool for Enzyme Characterization and Inhibitor Screening." Analytical Sciences 24:333-37 (2008).
Lopes et al., "Chemometrics in bioprocess engineering: process analytical technology (PAT) applications," Chemometrics and Intelligent Laboratory Systems 74(2):269-75 (2004).
Naik et al., Performance of hexamer peptide ligands for affinity purification of immunoglobulin G from commercial cell culture media, J Chromatogr A. 1218(13):1691-700 (2011).
Rathore et al., "Process analytical technology (PAT) for biopharmaceutical products," Anal Bioanal Chem. 398(1):137-54 (2010).
Read et al., "Process analytical technology (PAT) for biopharmaceutical products: Part II. Concepts and applications," Biotechnol Bioeng. 105(2):285-95 (2010).
Romig et al., "Aptamer affinity chromatography: combinatorial chemistry applied to protein purification," J Chromatogr B Biomed Sci Appl. 731(2):275-84 (1999).
Teixeira et al., "Advances in on-line monitoring and control of mammalian cell cultures: Supporting the PAT initiative," Biotechnol Adv. 27(6):726-32 (2009).

(Continued)

*Primary Examiner* — Paul J Holland
(74) *Attorney, Agent, or Firm* — McDonnell Boehnen Hulbert & Berghoff LLP

(57) ABSTRACT

The invention as disclosed herein provides a method for purifying a non-antibody protein from solution, comprising a chromatography step wherein the solution is passed over an affinity construct containing an affinity ligand-coupled solid support, wherein the affinity construct is associated with a bioprocess unit operation, and isolating the non-antibody protein from solution.

14 Claims, 15 Drawing Sheets

(56) References Cited

PUBLICATIONS

Thompson & Burgess, "Purification of recombinant human transcription factor IIB by immunoaffinity chromatography," Protein Expr Purif. 5(5):468-75 (1994).
Thompson et al., "Isolation and characterization of a polyol-responsive monoclonal antibody useful for gentle purification of *Escherichia coli* RNA polymerase," Biochemistry 31(30): 7003-8 (1992).
Walter et al., "Aptamers as affinity ligands for downstream processing," Eng. Life Sci. 12(5):496-506 (2012).
Wang et al., "Monitoring of glycoprotein products in cell culture lysates using lectin affinity chromatography and capillary HPLC coupled to electrospray linear ion trap-Fourier transform mass spectrometry (LTQ/FTMS)," Biotechnol Prog. 22(3):873-80 (2006).
Weber et al., "Immunoaffinity purification of the epidermal growth factor receptor. Stoichiometry of binding and kinetics of self-phosphorylation," J Biol Chem. 259(23):14631-6 (1984).
Yang & Hancock, "Monitoring glycosylation pattern changes of glycoproteins using multi-lectin affinity chromatography," J Chromatogr A. 1070(1-2):57-64 (2005).
Zanadian & Jungbauer, "An immunoaffinity column with a monoclonal antibody as ligand for human follicle stimulating hormone," J Sep Sci. 32(10):1585-91 (2009).
Du et al., "The role of mannosylated enzyme and the mannose receptor in enzyme replacement therapy." Am J Hum Genet., 77(6):1061-1074 (Dec. 2005; Epub Oct. 27, 2005).
Godawat et al., "Periodic counter-current chromatography—design and operational considerations for integrated and continuous purification of proteins." Biotechnol J., 7(12):1496-1508 (Dec. 2012; Epub Nov. 9, 2012). Abstract submitted.
Warikoo et al., "Integrated continuous production of recombinant therapeutic proteins." Biotech & Bioeng., 109(12):3018-3029 (Dec. 2012; Epub Aug. 6, 2012).

* cited by examiner

Enzyme 1

Enzyme 2

AFFINITY-BASED ANALYTICAL PURIFICATION OF BIOTHERAPEUTICS FOR BIOPROCESS MONITORING

CROSS-REFERENCE TO RELATED APPLICATIONS

This application is a divisional of U.S. application Ser. No. 14/214,105, filed Mar. 14, 2014, which claims priority to U.S. Provisional Application No. 61/790,676, filed Mar. 15, 2013, each of which is incorporated by reference herein in its entirety.

TECHNICAL FIELD

The invention relates to methods of biotechnology and the biomanufacturing of recombinant proteins.

BACKGROUND OF THE INVENTION

The ability to rapidly isolate a product from an impure mixture has been essential to many achievements in the areas of process development (Bareither & Pollard, 2011) and process monitoring (Callis et al., 1987) in the pharmaceutical (Lopes et al., 2004) and biotechnology industries (Rathore et al., 2010). This rapid isolation enables accurate measurement of product-specific critical quality attributes, such as protein glycosylation (Zandian et al., 2009) and product variants, which are not otherwise detectable when in the presence of impurities. These attributes are of particular importance because of their potential effects on product efficacy, safety, and immunogenicity (Hossler et al., 2009).

Many strategies have been developed to circumvent the need for pre-assay product isolation, including light-based chemometrics (Lopes et al., 2004; Hirschfelf et al., 1984; Read et al., 2010), multi-variate analytical algorithms (Kourti et al., 2006), and LC/MS or MS/MS techniques (Kuribayashi et al., 2012; Wang et al., 2006). Although these techniques have met success in their respective applications, each provides an excellent demonstration of the trade-offs among sensitivity, throughput, and complexity. While light-based techniques are minimally invasive and data-rich, their utility relies primarily on correlative predictions of performance instead of direct measurement of a specific attribute (Teixeira et al., 2009). Light-based techniques also suffer from potential signal-to-noise issues, particularly in dilute or highly impure samples. Conversely, mass spectrometric techniques provide exquisite resolution, but are considerably expensive and not easily transferred into a quality control ("QC") environment. While many achievements have been made in the area of direct product quality measurement in impure mixtures, these techniques have been unable to circumvent the need for product purification.

Due to the commercial availability of Protein A and Protein G resins, rapid target isolation is the state of the art for much of the biotechnology industry, currently dominated by antibody. Fc-fusion, and antibody-like products (Chon et al., 2011; Kelley et al. 2007). In the non-monoclonal antibody industry (i.e., enzymes, growth factors, and hematological factors), no such affinity resins are commercially available. As a result, multi-step purifications are required to isolate target protein, which has significantly affected achievement in process development and process monitoring. For process development, the resource requirements associated with multi-step purifications severely limit the granularity by which key product quality attributes, such as glycosylation (Hossler et al., 2009), can be studied as a function of bioprocess conditions. As a result, only a small subset of bioprocess conditions, among different bioreactor harvest days or cell culture conditions, can be probed. For process monitoring, the need for multi-step purifications renders most key analytical measurements impertinent for feedback control of a bioprocess. In order to achieve the principles of the Process Analytical Technology (PAT) paradigm (Callis et al., 1987) for non-monoclonal antibody biotherapeutics, analytical measurements must be provided in a timely manner (Rathore et al., 2010). To do so, the purification bottleneck caused by the lack of Protein A-like affinity resins must be removed.

Custom antibody-based immunoaffinity resins have been developed to isolate non-antibodies from impure mixtures, most commonly recombinant cell culture milieux and bacterial cell lysates, including target molecules such as erythropoictin (Le Floch et al., 2004), epidermal growth factor receptor (Weber et al., 1984), oligonucleotide polymerases (Thompson et al., 1992; Burgess et al., 2002), and transcription factors (Thompson et al., 1994). While these examples have met their respective applications, they do not provide a general methodology for the successful implementation of such affinity constructs in product development or product monitoring applications.

There are a number of alternatives to antibody affinity ligands, including antibody fragments (Berry et al., 1991; Harmsen et al., 2007), aptamers (Walter et al., 2012; Romig et al., 1999), small peptides (Naik et al., 2011), and lectins (Wang et al., 2006; Yang et al., 2005). Although these alternative affinity ligands provide many potential benefits, including the ability to elute under milder conditions (Walter et al., 2012), increased stability (Harmsen et al., 2007; Naik et al., 2011), and comparatively lower cost (Naik et al., 2011), they have yet to find consistent use in industry because of the significant advantages associated with the use of antibodies as affinity ligands, including their universality, well-established procedures for both monoclonal clone selection and polyclonal production, and long track record in process and analytical development.

BRIEF SUMMARY OF TILE INVENTION

The disclosure provided herein describes a method for purifying a non-antibody protein (NAP) from a heterogeneous solution, the method comprising: (a) contacting the heterogeneous solution comprising the NAP with an affinity construct comprising a solid support coupled to an affinity ligand that binds the NAP, and (b) isolating the affinity-purified NAP from the heterogeneous solution, wherein the affinity-purified NAP comprises a critical quality attribute (CQA) that is predictive of the CQA of the NAP produced by a multi-step bioprocess.

In another aspect of the disclosure, a method is described herein for purifying a non-antibody protein from solution comprising the following steps: (a) a chromatography step wherein the solution is passed over an affinity construct comprising an affinity ligand-coupled solid support, wherein the affinity construct is associated with a bioprocess unit operation, and (b) isolating the non-antibody protein from solution.

In another aspect of the disclosure, a method is described herein for purifying a non-antibody protein (NAP) from a heterogeneous solution, the method comprising the following steps: contacting the heterogeneous solution comprising the NAP with an affinity construct comprising a solid support coupled to an affinity ligand that binds the NAP, wherein the affinity construct is capable of performing at least 50 chromatographic cycles; and isolating the affinity-purified NAP from the heterogeneous solution; wherein the affinity-purified NAP comprises a critical quality attribute (CQA) that is predictive of the CQA of the NAP produced by a multi-step bioprocess.

Other features and advantages of the invention will be apparent from the following disclosure, including the detailed description, drawings, examples, and claims.

DETAILED DESCRIPTION OF THE INVENTION

Figure 1:
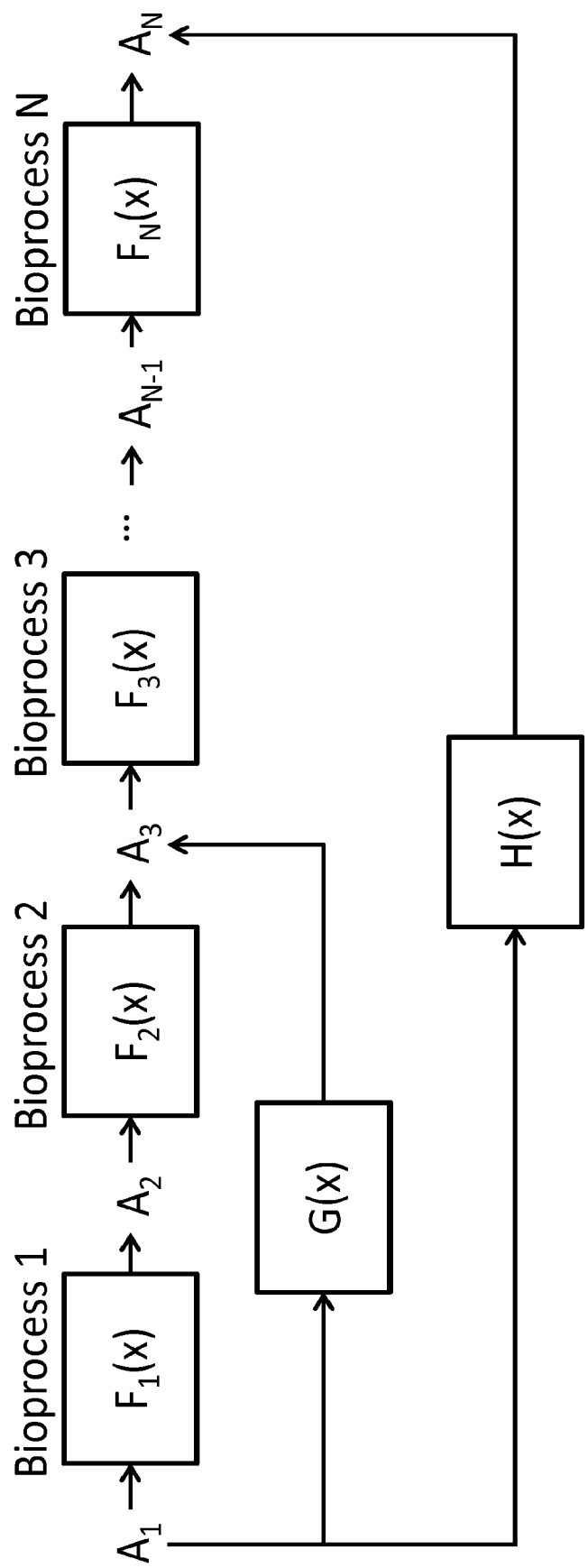
FIG. 1 shows a mathematical representation of the effect of a bioprocess on product quality and the predictive models developed using the single-step affinity technique to account for and study such effects.

The invention as disclosed herein encompasses a methodology that has been developed to purify non-antibody therapeutic proteins from cell culture or other impure mixtures in a single step. The methodology was developed initially for polyclonal antibodies raised against an enzyme biotherapeutic protein and successfully re-applied, with minimal modification, using a monoclonal antibody against a second enzyme biotherapeutic. The methodology includes procedures for generating and implementing the purification technique as well as an overall framework by which the procedure can be qualified and benchmarked against a traditional, multi-step purification process used to initially isolate a non-antibody biotherapeutic. This overall framework results in predictive model(s) that can be used to transform affinity eluate product quality data into that which would have been obtained after processing by a multi-step bioprocess. These predictive models, together with the affinity construct described herein, provide drug substance-equivalent product quality information while obviating the need to produce actual drug substance.

Antibody purification and coupling procedures were optimized as shown below, particularly with respect to static binding efficiency, to ensure maximal use of the antibody supply while also enabling the production of an analytical scale column. Column methods were developed to achieve single-step purification and elution conditions were designed to maximize recovery while minimizing adverse effects to product quality, such as increased aggregation. To qualify the affinity purification, harvest fluid lots were purified by the affinity column and two or four column process trains and direct product quality comparisons were performed. In the cases where product quality was not comparable for the two purification methods, such as specific activity and the relative abundance of certain glycans, predictive models were developed to account for the observed differences. These predictive models allow for the use of the anti-enzyme affinity columns in place of the multi-step process trains for the study of critical quality attributes of a biomolecule. Examples of these studies for several critical quality attributes are disclosed herein.

Overall, the general procedures and methodology developed during the Enzyme 1 proof-of-concept were re-applied throughout column and method development efforts for Enzyme 2. No single protocol or list of buffers will be universal for all antibody-antigen pairs and column and method development is required for each new molecule of study. Nonetheless, the single-step affinity methodology provides many potential benefits to a research and development organization studying non-monoclonal antibody biotherapeutics, including: (1) significantly reduced resource requirements for purification support of cell culture, (2) increased throughput and significantly shorter time to purified product, and (3) numerous opportunities for enhancing analytical development. Additionally, the methodology is an enabling component of any Process Analytical Technology (PAT) designed to provide on-time product quality-based decision-making for bioprocess control. Although most of these benefits have long been realized in the Mab industry due to the prevalence of Protein A and G resins, successful development and effective implementation of these anti-Enzyme antibody affinity technology will be similarly impactful for the non-Mab industry.

In the invention as disclosed herein, the extensive past achievement in immunoaffinity purification has been leveraged to develop single step, analytical scale affinity purifications for two different non-Mab biotherapeutics using both polyclonal and monoclonal antibody ligands. Eluates recovered by the single-step affinity techniques were demonstrated to be predictive of drug substance produced using a traditional, multi-step (non-affinity) purification train. By using the custom affinity media, target molecules were rapidly isolated from cell culture harvest in sufficient purity for all desired product quality analyses, significantly reducing development resource requirements, both in terms of purification operations and analytical testing of intermediates. Optimization was performed throughout the immunoaffinity column production and method development to maximize process economies to ensure efficient use of antibody supply, maximum target recovery, and minimal target protein degradation.

1. Theoretical Basis for the Model

The methods disclosed herein involve the development of predictive models. The theoretical basis for the predictive models derives from the fact that every step or bioprocess unit operation within a multi-step bioprocess changes (or has the potential to change) the product quality of the biomolecule in production. When a biomolecule (for example a non-antibody protein) is secreted from the production cell within the bioreactor, it is subject to a number of bioprocess unit operations further downstream of the reactor. Examples of such operations include clarification (centrifugation, filtration, precipitation, flocculation), chromatography (capture, intermediate, polishing), viral inactivation, and filtration processes. In addition to these well-established bioreactor unit operations, the biomolecule is subject to more subtle processes, which are primarily related to hold time in a certain condition. These hold times may occur at a process intermediate stage, such as in between two column chromatography operations, or even within a unit operation itself, such as the implicit hold time between the secretion of the biomolecule from the cell to the termination of the bioreactor or separation of the biomolecule from the bioreactor milieu. These hold time processes may also change the product quality of the biomolecule.

A mathematical transformation formalism can be used to more generally describe the manner by which bioprocess unit operations affect the product quality of a biomolecule in production. This formalism is depicted in FIG. 1. In a generic bioprocess, a biomolecule is secreted from the cell in a bioreactor having the product quality vector, $A_1$. This product quality vector includes all the measurable properties of interest of the biomolecule, which may or may not be different from that obtained at the end of the complete bioprocess. Bioprocess Step 1, which could be a clarification step as an example, may change the product quality of the processed biomolecule either due to selective enrichment or loss of particular isoforms, such as by charge interactions, or by a direct effect on the entire biomolecule population, such as by application of shear stress.

The effect of Bioprocess Step 1 on product quality can be represented as an operator function, $F_1(x)$, that acts on its input, in this case $A_1$, to yield a final biomolecule population represented by the product quality vector $A_2$ (FIG. 1). Each subsequent step in the bioprocess acts on the biomolecule with the corresponding operator function, $F_i(x)$. After N steps, the product quality vector has become $A_N$.

The exact definition of these operator functions is very difficult to determine for many steps within a multi-step non-antibody bioprocess due to the significant levels of impurities present at early and middle stages (typically anything before polishing chromatography) of the overall bioprocess. Because subsequent purification steps are required to isolate the biomolecule of interest, any changes to the biomolecule product quality vector caused by downstream steps of the process may convolute or obscure any product quality effects further upstream. It is for these reasons that an affinity purification technique together with appropriately designed direct comparison studies are required to develop predictive models that enable effective study determining the effect of many bioprocess unit operations on product quality.

One particular type of direct comparison study, such as those described herein, obtains cell culture harvest and purifies it by two techniques: (1) the single-step affinity purification described herein and (2) a multi-step downstream purification process. By comparing the product quality obtained by these two methodologies, a predictive model can be devised summarizing the effect of the non-affinity, multi-step purification process on the product quality of the biomolecule as produced by the bioreactor. This model is depicted as H(x) in FIG. 1 and can be described mathematically as follows:

$$A_N = H(A_1)$$

Where $A_1$ is the product quality vector for the biomolecule as obtained from the bioreactor and $A_N$ is the product quality vector at the end of the entire multi-step bioprocess, or, $$A_N = H(A_1) = F_N(F_{N-1}( \ldots (F_3(F_2(F_1(A_1)))))).$$

The precise form of the predictive model chosen for H(x) can be as simple or complex as justified by the direct comparison results and statistical power. One of ordinary skill in the art is capable of selection and, if necessary, adjustment of the precise form of the predictive model.

In other scenarios or embodiments, separate predictive models can be developed for a single bioprocess, i, to precisely determine the operator function, $F_i$. In additional scenarios or embodiments, separate predictive models can be developed for a group of bioprocess unit operations within a multi-step bioprocess. An example of this is G(x), which encompasses the product quality effects of Bioprocesses 1 and 2 (FIG. 1) and can be represented mathematically as:

$$A_3 = G(A_1) = F_2(F_1(A_1)).$$

The effect of the affinity purification on product quality must be well understood to account for any biases introduced by the affinity purification itself. Fortunately, this bias is readily studied since a purified biomolecule can be processed on the affinity technique and analyzed before and after processing to discern any differences attributable to the affinity technique. These differences can be accounted for in the development of the predictive models, such as G(x) and H(x), described above and depicted in FIG. 1.

Figure 2:
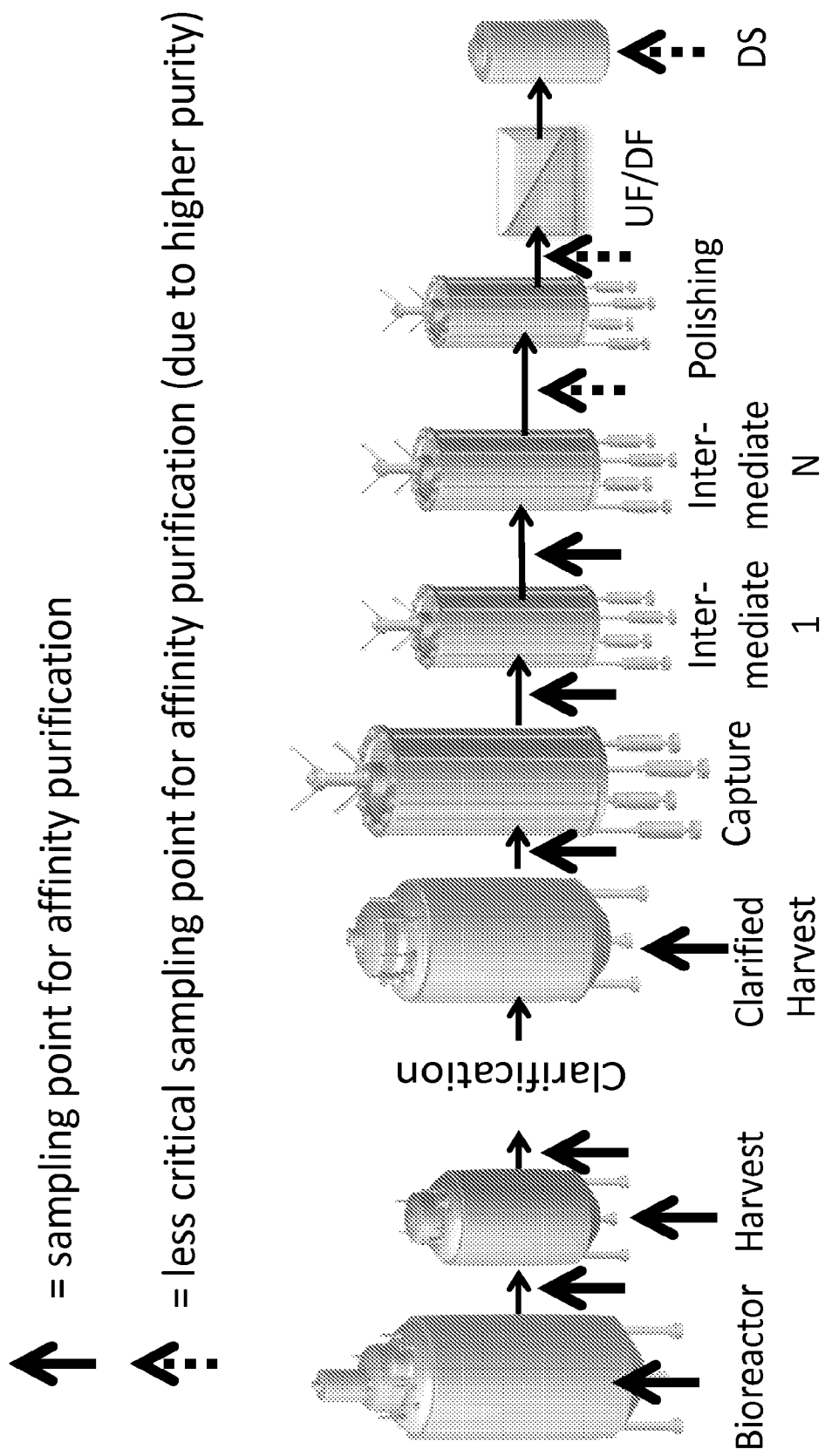
FIG. 2 shows a hypothetical bioprocess with potential sampling points for affinity purification indicated throughout, including points before, after, and within a particular bioprocess unit operation.

While the abstract mathematical formalism successfully encompasses any potential bioprocess, it is also useful to consider a hypothetical bioprocess and at which stage the affinity purification may be applied to analyze or further develop the bioprocess. In FIG. 2, potential sampling points at various stages of the bioprocess are indicated. These potential sampling points include, for example, before, after, and within a bioprocess unit operation (FIG. 2). These exemplary sampling points are not intended to be exhaustive or limiting, as other sampling points and paradigms are possible. One of ordinary skill in the art is capable of selecting appropriate sampling points and paradigms. FIG. 2 also indicates that affinity purification is less impactful at later stages within the overall bioprocess due to the increased purity of the biomolecule product, particularly at the polishing chromatography and terminal ultrafiltration/diafiltration (UF/DF) stages.

2. Applications of the Disclosed Methods

Specific applications of the affinity media are proposed to demonstrate the utility of the technique in process development applications typical within non-Mab biotechnology companies, such as support of cell culture clone selection and cell bank evaluation. The methods as disclosed herein also encompasses potential applications for the immunoaffinity resin in scale-down and/or commercial process monitoring and Process Analytical Technology (PAT).

Figure 3:
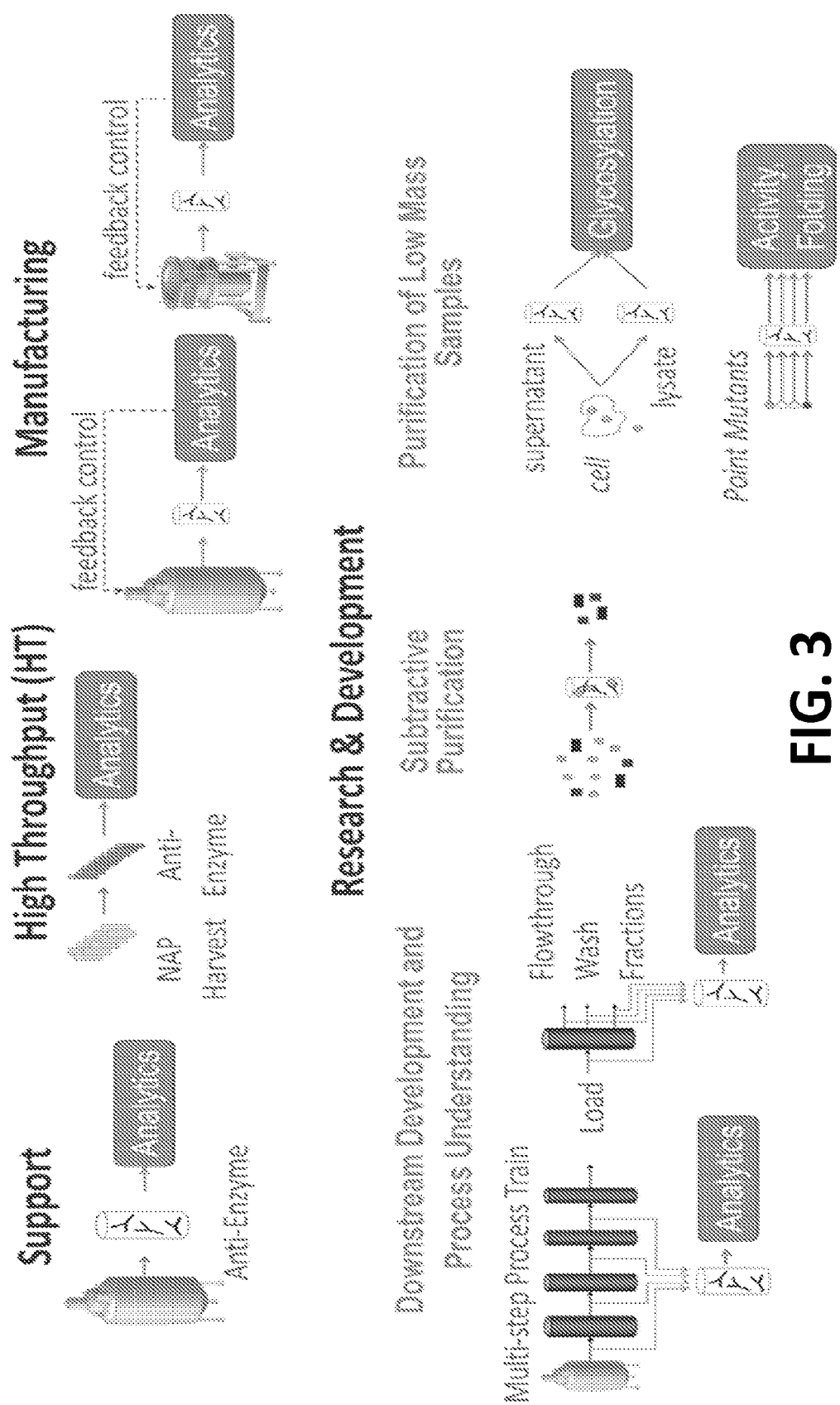
FIG. 3 shows a summary schematic of potential applications for the anti-Enzyme affinity columns disclosed herein. Note: Schematic drawings presented in FIG. 3 are not to scale.

The potential applications for anti-enzyme affinity columns are numerous. Some of these applications are depicted in FIG. 3. Non-limiting examples of such applications can be broadly categorized as support, high throughput (HT), manufacturing, or research and development activities. Non-limiting examples of cell culture support include evaluation of working cell banks and analysis of critical quality attributes during upstream development. Non-limiting examples of high-throughput applications include rapid/parallel processing, support of low mass and HT cell culture (CC), and direct integration with HT CC and HT analytics. Non-limiting examples of manufacturing applications include continual critical quality attribute analysis in bioreactors, product quantification, and periodic countercurrent chromatography (PCC) column switching. Non-limiting examples of research and development activities or applications are tracking product quality in multi-step processes, determining the effect of downstream steps on selected critical quality attributes during development, HCP isolation, identification of key impurities, impurity reference standard generation, mutant purification, and glycosylation analysis for cellular internalization.

In one embodiment, the method disclosed herein provides purification support to cell culture process development activities (FIG. 3). The direct comparison studies presented in the Examples confirm the capability of the use of these affinity columns in such a manner. The affinity columns produce affinity-purified NAPs that are predictive of the NAPs produced by multi-step purification processes or trains. The ability to isolate non-antibody proteins (NAPs) from harvest fluid, heterogeneous solutions, or other impure mixtures in a single step is a tremendous advantage relative to the multi-step purification trains. Specific benefits include: (1) reduced full time equivalent (FTE) requirements for executing purifications as well as intermediate analytics, (2) diminished timelines to obtain purified product, and (3) reduced material requirements in terms of target protein and buffers.

As an example, the resource requirements required to execute the direct comparison studies, which included side-by-side purification of identical load materials using either affinity or process train techniques, are summarized in Table 1. Surprisingly, the affinity column significantly reduces FTE, protein mass, and buffer requirements, while also significantly reducing purification timelines. The relative savings were considerably higher for the Enzyme 2 case due primarily to the low titer of Enzyme 2 in harvest and the correspondingly greater purification factor required to achieve the required purity (>98%).

TABLE 1

Resource requirements for the direct comparison study separated according to purification strategy.

| | Enzyme 1 | | Enzyme 2 | | |
|---|---|---|---|---|---|
| Property | Affinity | Process Train | Affinity | Process Train | Units |
| Column Steps | 1 | 2 | 1 | 4 | N/A |
| Full Time Equivalents | 1 | 2 | 1 | 2.5 | FTEs |
| Total Purification Time | 2 | 10 | 1.5 | 20 | Business Days |
| Initial Enzyme Mass Required | 2 | 20 | 2.5 | 1000 | mg |
| Total Buffer Volume | 5 | 50 | 3 | 200 | L |

A single affinity column operation required 3-6 hours (depending on load concentration): therefore the reduced time to purified material when using the affinity column is particularly surprising. Conversely, the process train purifications required significantly greater time due to the multiple column steps as well as the time to obtain intermediate concentration results (i.e., by activity testing). The single-step affinity purification, including its short cycle time, allows for considerably greater throughput, providing the opportunity for purification of a larger number of samples.

Current cell culture development tends to focus on monitoring bioreactor performance, with instrumentation capable of continuous or near-continuous measurement of bioreactor conditions, metabolites, and, titers (FIG. 3).

Specific measurements of product quality, particularly glycosylation, dimer content, and product variants, are typically performed sparingly during cell culture experimentation due to the inability to measure these properties in harvest and the significant resources required to purify a single harvest sample. The anti-enzyme affinity columns as disclosed herein enable monitoring of selected product quality attributes as a function of key cell culture parameters, such as perfusion harvest day, with granularity and throughput otherwise unavailable.

In further embodiments, the improved throughput can also allow for product quality analyses during design of experiment (DoE) studies that previously focused primarily (and oftentimes exclusively) on measurements of product titer as the experimental output. The affinity constructs disclosed herein provide for the analysis of many CQA and experimental outputs.

In additional embodiments, further throughput improvements can also be realized by adapting the anti-enzyme affinity resins with other high throughput purification platforms already frequently utilized in the industry. Robotic liquid handlers, such as the Tecan EVO and Hamilton Star systems, together with commercially available chromatographic media, such as Atoll columns or GE Predictor plates, have successfully performed multiple small-scale purifications in parallel (FIG. 3).

The resultant high throughput anti-enzyme affinity resins can be used to support low mass, high throughput cell culture development systems and can also be directly integrated with high throughput cell culture systems, high throughput analytics, or both (FIG. 3). The ability to significantly increase purification throughput is also associated with a significant increase in the number of samples available for analytical testing. Moreover, the types of tests that require such levels of product purity yielded by single-step affinity purifications, including glycosylation profile analysis and size exclusion chromatography (SEC), are often times the most resource-intensive.

For commercial and drug development purposes the affinity construct should be durable and capable for repeated efficient chromatographic cycling. In one embodiment, the affinity construct is capable of performing at least 50 chromatographic cycles. In another embodiment, the affinity construct is capable of performing at least 70 chromatographic cycles, at least 80 chromatographic cycles, at least 90 chromatographic cycles or at least 100 chromatographic cycles. In another embodiment, the affinity construct is capable of performing at between 50 and 100 chromatographic cycles, between 60 and 120 chromatographic cycles, or between 70 and 130 chromatographic cycles.

The anti-enzyme affinity resins, such as those disclosed herein, can also be helpful tools in downstream applications (FIG. 3). For example, column loads and eluates can be purified on the affinity resin and analyzed for selected CQAs to determine the effect of column chemistry or operational conditions on product quality. This type of study can be used to improve process understanding for commercial processes or help support process development efforts. The affinity technique would be most applicable for study of columns earlier in a process train where sample purity, even of eluates, is often well below 95% (see, e.g., FIG. 2).

The single-step affinity columns are also a key component in any process analytical technology (PAT) platform in which product isolation is required before analytical measurements can be performed. The precise integration of these columns to such a platform will depend on the frequency of bioreactor sampling and the type of analytical instrumentation (HPLC, liquid handler, etc.) to which the affinity purification is linked.

As disclosed herein, there are also a number of analytical applications for the affinity resins. Affinity chromatography and immunoprecipitation have classically been used for subtractive purification in which the main component (product) is specifically removed and the flow-through (or supernatant) is recovered and analyzed (FIG. 3). This technique is used for host cell protein impurity identification, which is otherwise extremely difficult due to signal saturation caused by the prevalence of non-impurities (product) in a sample. Subtractive purification can also be used to isolate process-specific enzymes, including proteases or glycosylases. Identification of such process-specific enzymes can provide support for assay development related to measurement of clipped or cleaved product variants.

In one aspect, another benefit of the anti-enzyme affinity resin is the ability to purify very small amounts of enzyme. While one to two milligrams were purified for the direct comparison studies discussed herein, significantly less material can be processed and recovered, either with smaller columns or by immunoprecipitation techniques due to the specificity of the affinity interaction. In contrast, process train purifications require loading within target ranges to ensure purification performance and use of packed columns with sufficient height to provide the required resolution. Together, these requirements make traditional, multi-step purifications very material intensive.

The ability to purify and study smaller mass samples opens up a considerable number of potential applications. Two non-limiting examples of such applications are depicted in FIG. 3. As shown in FIG. 3, using an in vitro cellular uptake assay, the distribution of glycoforms and glycans in the supernatant and cell lysate can be measured to draw inferences about cellular uptake mechanisms (i.e., receptor mediated endocytosis, pinocytosis, etc.).

Mutant purification is another exemplary application (FIG. 3). Point mutants, which are typically produced in very small amounts in low-producing cell lines, can be purified by the affinity column to enable study of the contribution of various amino acids to catalytic activity or structural integrity.

3. Definitions

As used herein, the word "a" before a noun represents one or more of the particular noun. For example, the phrase "a non-antibody protein" represents "one or more non-antibody proteins."

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The term "substantially free" means a composition (e.g., a liquid culture medium) that is at least or about 90% free (e.g., at least or about 95%, 96%, 97%, 98%, or at least or about 99% free, or about 100% free) of a specified substance.

The term "culturing" or "cell culturing" means the maintenance or proliferation of a cell under a controlled set of physical conditions.

The term "non-antibody protein", also referred to as "NAP", means a recombinant protein (e.g., an engineered protein, or enzyme) that is purified and/or isolated from a heterogeneous solution comprising the NAP target and other components that are not the NAP target. Examples of such components are contaminating proteins, lipids, and nucleic acids present in a liquid culture medium or from a host cell (e.g., from a mammalian, yeast, or bacterial host cell) and other biological contaminants (e.g., viral and bacterial contaminants). In certain embodiments, the NAP is produced using a multi-step bioprocess. The term "non-antibody protein" can refer to the protein product at any stage of a bioprocess, including before, during, or after a purification stage.

In certain embodiments, the non-antibody protein is a biotherapeutic protein. The biotherapeutic protein can be, e.g., an enzyme, hormone, hematological factor, growth factor, or immunological factor. In addition, a "non-antibody protein" as used herein is any protein that is unable to be bound through any one of the following immunoglobulin-specific affinity interactions: Protein A binding to the Fc-region, Protein G binding to the Fab-region, Protein G binding to the Fc-region, or Protein L binding to the immunoglobulin light chain.

In certain embodiments, the purified NAP can be formulated into a pharmaceutical agent or drug substance without a further substantial purification and/or decontamination step. In additional embodiments, the NAP is a commercial biologic and/or drug substance. In yet additional embodiments, the NAP is produced using a commercial process or manufacturing process.

Non-limiting examples of non-antibody proteins that can be produced by the methods provided herein include enzymes (e.g., a galactosidase (e.g., an alpha-galactosidase), alglucosidase alpha, imiglucerase, or acid sphingomyelinase), proteins (e.g., human erythropoietin, tumor necrosis factor (TNF), thyroid stimulating hormone (TSH), or an interferon alpha or beta), or immunogenic or antigenic proteins or protein fragments (e.g., proteins for use in a vaccine). Non-limiting examples of non-antibody proteins that can be produced by the present methods include: alglucosidase alfa, laronidase, abatacept, galsulfase, lutropin alfa, antihemophilic factor, agalsidase beta, interferon beta-1a, darbepoetin alfa, tenecteplase, etanercept, coagulation factor IX, follicle stimulating hormone, interferon beta-1a, imiglucerase, dornase alfa, epoetin alfa, Fabrazyme®, and alteplase.

A secreted, soluble non-antibody protein can be recovered from the liquid culture medium by removing or otherwise physically separating the liquid culture medium from the cells. A variety of different methods for removing liquid culture medium from cells are known in the art, including, for example, centrifugation, filtration, pipetting, and/or aspiration. The secreted non-antibody protein can then be recovered and further purified from the liquid culture medium using a variety of biochemical techniques including various types of chromatography (e.g., affinity chromatography, molecular sieve chromatography, cation exchange chromatography, or anion exchange chromatography) and/or filtration (e.g., molecular weight cut-off filtration).

As used herein, an "affinity construct" can be, e.g., a packed column or a well-mixed suspension. In another embodiment, the affinity construct can be, e.g., a chromatography membrane. In certain embodiments, these configurations can be studied, e.g., on the bench-top in small containers (such as microcentrifuge tubes), in a chromatography system (such as an Akta), or within a liquid handling system (such as Atoll columns on a Tecan EVO 150).

In some embodiments, the affinity construct comprises one or more process parameters. Examples of process parameters are those that have an impact on the successful completion of the purpose of the step and/or the product quality of the NAP formed at an intermediate step or subsequent step in the process. Certain process parameters can be optimized to directly impact a critical quality attribute of an intermediate, drug substance, or final product. In certain embodiments, the affinity construct comprises a parameter that is optimized to maximize the quality and/or purity of the affinity-purified NAP. In other embodiments, the affinity construct comprises a parameter that is optimized to maximize the coupling yield and/or ligand binding capacity of the affinity construct. In yet other embodiments, the optimized parameter is coupling chemistry, coupling buffer pH, coupling buffer ionic strength, coupling time, coupling temperature, and/or ligand density.

In one embodiment, the "affinity ligand" of the affinity ligand-coupled based solid support is a monoclonal antibody. In another embodiment, the ligand of the affinity ligand-coupled based solid support is a polyclonal antibody. In additional embodiments, the ligand of the affinity ligand-coupled based solid support is an aptamer, small peptide, or antibody fragment. Non-limiting examples of biologic drugs that are antibodies include: panitumumab, omalizumab, abagovomab, abciximab, actoxumab, adalimumab, adecatumumab, afclimomab, afutuzumab, alacizumab, alcmtuzumab, alirocumab, altumomab, amatuximab, anatumomab, apolizumab, atinumab, tocilizumab, basilizimab, bectumomab, belimumab, bevacizumab, biciromab, canakinumab, cetuximab, daclizumab, densumab, eculizumab, edrecolomab, efalizumab, efungumab, ertumaxomab, etaracizumab, etanercept, golimumab, infliximab, natalizumab, palivizumab, panitumumab, pertuzumab, ranibizumab, rituximab, tocilizumab, and trastuzumab. In another embodiment, the affinity ligand is an imiglucerase antibody, an agalsidase beta antibody, an alglucosidase alpha antibody, or an acid sphingomyelinase antibody. In certain embodiments, the affinity ligand is coupled to the solid support by formation of secondary amine, tertiary amine, amide, triazole, disulfide, or hydrazone bonds. As used herein, in certain embodiments the "solid support" is an agarose-based resin. In other embodiments, the solid support comprises non-agarose chromatography media, monoliths or nanoparticles. In certain embodiments, chromatography media can be, e.g., methacrylate, cellulose, or glass. In other specific embodiments, the nanoparticles are gold nanoparticles or magnetic nanoparticles.

The term "integrated process" means a process which is performed using structural elements that function cooperatively to achieve a specific result (e.g., the generation of a therapeutic protein drug substance from a liquid culture medium). In one embodiment, the affinity construct is integrated with the bioprocess.

The term "at-line" means that a sample is permanently removed from the production process but is analyzed in a time-frame in close proximity to the time in which it was removed, thereby, providing real-time or near-real time information which may be used to automatically control or change in-process conditions. "At-line" analysis may be performed in an automated or semi-automated fashion. In one embodiment, the affinity construct is integrated in an at-line mode with the bioprocess.

The term "in-line" means that a sample is obtained by direct sampling from a process stream and analyzed with a device directly connected or integrated with the process. In-line analyses are advantageous because they can usually be performed at significantly higher frequency intervals (including continuously or discontinuously) compared to off-line and at-line analytical methods. In one embodiment, the affinity construct is integrated in an in-line mode with the bioprocess.

In yet another embodiment, the affinity construct is integrated in an offline mode with the bioprocess. The term "offline" means that a sample is removed from the production process and analyzed independently of the progression of the process. For example, a sample is taken out of a bioreactor to be analyzed using an analytical device.

The term "continuous process" means a process that continuously achieves or produces a result (e.g., a process which continuously produces a therapeutic protein drug substance from a liquid culture medium). For example, in certain exemplary biological manufacturing systems described herein, a therapeutic protein drug substance is continuously produced while the systems are in operation (accounting of course for an initial lag period while the non-antibody protein travels through the system to the exit port).

The term "semi-continuous process" means a process that to a generally continuous process for purifying a target molecule, where input of the fluid material in any single process step or the output is discontinuous or intermittent. For example, the input in a process step (e.g., a bind and elute chromatography step) may be loaded continuously; however, the output may be collected intermittently, where the other process steps in the purification process are continuous. Accordingly, in some embodiments, the processes described herein are "semi-continuous", in that they include at least one unit operation which is operated in an intermittent matter, whereas the other unit operations in the process or system may be operated in a continuous manner.

An "immunoglobulin" may be a subclass of IgG (e.g., IgG1, IgG2, IgG3, or IgG4). The immunoglobulin may be an antibody fragment, e.g., a Fab fragment, a F(ab')$_2$ fragment, or an a scFv fragment. The immunoglobulin may also be a bi-specific antibody or a tri-specific antibody, or a dimer, trimer, or multimer antibody, or a diabody, an Affibody®, or a Nanobody®. Non-limiting examples of immunoglobulins are described herein and additional examples of immunoglobulins are known in the art.

The term "protein fragment" or "polypeptide fragment" means a portion of a polypeptide sequence that is at least or about 4 amino acids, at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length. A recombinant protein fragment can be produced using any of the processes described herein.

The term "engineered protein" means a polypeptide that is not naturally encoded by an endogenous nucleic acid present within an organism (e.g., a mammal). Examples of engineered proteins include enzymes (e.g., with one or more amino acid substitutions, deletions, insertions, or additions that result in an increase in stability and/or catalytic activity of the engineered enzyme), fusion proteins, antibodies (e.g., divalent antibodies, trivalent antibodies, or a diabody), and antigen-binding proteins that contain at least one recombinant scaffolding sequence.

The term "glycoform" refers to isoforms of a protein that differ only with respect to the number or type of attached glycans. Glycoproteins often exist as a number of different glycoforms, with alterations in the attached glycans.

The term "glycan" refers to the saccharides and oligosaccharides that are linked enzymatically to proteins to create glycoproteins.

The term "recover" or "recovering" means a step performed to partially purify or isolate (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight) a non-antibody protein from one or more other components present in a liquid culture medium or a diluted liquid culture medium (e.g., culture medium proteins or one or more other components (e.g., DNA, RNA, or other proteins) present in or secreted from a mammalian cell). Typically, capturing is performed using a resin that binds a non-antibody protein (e.g., through the use of affinity chromatography). Non-limiting methods for capturing a non-antibody protein from a liquid culture medium or diluted liquid culture medium are described herein and others are known in the art. A non-antibody protein can be recovered from a liquid culture medium using a chromatography column or chromatographic membrane (e.g., any of the chromatography columns or chromatographic membranes described herein).

The term "purifying" means a step performed to isolate a non-antibody protein from one or more other components present in a fluid containing a non-antibody protein (e.g., liquid culture medium proteins or one or more other components (e.g., DNA, RNA, or other proteins) present in or secreted from a mammalian cell). For example, purifying can be performed after an initial capturing step. Purifying can be performed using a resin that binds a non-antibody protein (e.g., through the use of affinity chromatography, anion or cation exchange chromatography, or molecular sieve chromatography). A non-antibody protein can be polished from a fluid containing the protein using a chromatography column or chromatographic membrane (e.g., any of the chromatography columns or chromatographic membranes described herein).

The term "eluate" is a term of art and means a fluid that is emitted from a chromatography column or chromatographic membrane that contains a detectable amount of a non-antibody protein.

The term "filtering" means the removal of at least part of (e.g., at least 80%, 90%, 95%, 96%, 97%, 98%, or 99%) undesired biological contaminants (e.g., a mammalian cell, bacteria, yeast cells, viruses, or mycobacteria) and/or particulate matter (e.g., precipitated proteins) from a liquid (e.g., a liquid culture medium or fluid present in any of the systems or processes described herein).

The term "secreted protein" or "secreted recombinant protein" means a protein (e.g., a recombinant protein) that originally contained at least one secretion signal sequence when it is translated within a mammalian cell, and through, at least in part, enzymatic cleavage of the secretion signal sequence in the mammalian cell, is secreted at least partially into the extracellular space (e.g., a liquid culture medium). Skilled practitioners will appreciate that a "secreted" protein need not dissociate entirely from the cell to be considered a secreted protein.

The term "perfusion bioreactor" means a bioreactor containing a plurality of cells in a first liquid culture medium, wherein the culturing of the cells present in the bioreactor includes periodic or continuous removal of the first liquid culture medium and at the same time or shortly thereafter adding substantially the same volume of a second liquid culture medium to the bioreactor. In some examples, there is an incremental change (e.g., increase or decrease) in the volume of the first liquid culture medium removed and added over incremental periods (e.g., an about 24-hour period, a period of between about 1 minute and about 24-hours, or a period of greater than 24 hours) during the culturing period (e.g., the culture medium refeed rate on a daily basis). The fraction of media removed and replaced each day can vary depending on the particular cells being cultured, the initial seeding density, and the cell density at a particular time. "RV" or "reactor volume" means the volume of the culture medium present at the beginning of the culturing process (e.g., the total volume of the culture medium present after seeding).

The term "feed-batch bioreactor" is a term of art and means a bioreactor containing a plurality of cells in a first liquid culture medium, wherein the culturing of the cells present in the bioreactor includes the periodic or continuous addition of a second liquid culture medium to the first liquid culture medium without substantial or significant removal of the first liquid culture medium or second liquid culture medium from the cell culture. The second liquid culture medium can be the same as the first liquid culture medium. In some examples of feed-batch culture, the second liquid culture medium is a concentrated form of the first liquid culture medium. In some examples of feed-batch culture, the second liquid culture medium is added as a dry powder.

The term "bioprocess unit operation", as used herein, generally refers to any process applied to a non-antibody protein (NAP) according to the disclosed methods. In certain embodiments, the bioprocess unit operation is a functional step that can be performed in a process of manufacturing a therapeutic protein drug substance from a liquid culture medium. Non-limiting examples of bioprocess unit operations include filtering (e.g., removal of contaminant bacteria, yeast viruses, or mycobacteria, and/or particular matter from a fluid containing a non-antibody protein), capturing, epitope tag removal, purifying, holding or storing, polishing, viral inactivating, adjusting the ionic concentration and/or pH of a fluid containing the non-antibody protein, and removing unwanted salts. In certain embodiments, the bioprocess unit operation is a bioreactor process, seed train, capture chromatography, intermediate chromatography, filtration, centrifugation, precipitation, flocculation, UV irradiation, and/or viral inactivation. In other embodiments, the bioprocess unit operation occurs within a bioreactor or chromatography apparatus. In one embodiment, the bioprocess unit operation facilitates at least one of seed train and inoculation, bioreactor production or purification steps having low product purity eluates.

In some embodiments, the term "monitoring" as used in the phrase "monitoring and controlling" refers to the ability to measure specific process parameters or process outputs such as pH, dissolved oxygen, media components, bioprocess unit operations, flow rate and CQAs at some point in the process or for the duration of the process. In some embodiments, the term "controlling" as used in the phrase "monitoring and controlling" refers to the ability to change process parameters process outputs such as pH, dissolved oxygen, media components, bioprocess unit operations, flow rate and CQAs in response to observations made by monitoring those specific parameters.

In some embodiments, the term "bioprocess unit operation" refers to a single functional step within a process. In other embodiments, the bioprocess unit operation comprises multiple functional steps within a multi-step bioprocess. Examples of bioprocess unit operations comprising multiple functional steps are represented as G(x) or H(x) in FIG. 1.

In one aspect of the disclosure, described herein is a method of monitoring or controlling a bioprocess unit operation within a multi-step bioprocess for producing a NAP. In certain embodiments, the method of monitoring or controlling a bioprocess unit operation within a multi-step bioprocess for producing a NAP comprises the following steps: a) purifying the affinity-purified NAP from solution, b) determining a critical quality attribute (CQA) of the affinity-purified NAP, c) comparing the CQA of the affinity-purified NAP to the CQA of the NAP produced by the bioprocess unit operation within a multi-step bioprocess, d) calculating a difference between the CQA of the affinity-purified NAP and the NAP produced by the bioprocess unit operation within a multi-step bioprocess, and e) monitoring or controlling the bioprocess unit operation based on the calculated difference in CQAs.

In another aspect of the disclosure, described herein is a method of monitoring or controlling a bioprocess unit operation within a multi-step bioprocess for producing a NAP comprises the following steps: a) purifying the affinity-purified NAP from solution, b) determining a critical quality attribute (CQA) of the affinity-purified NAP, c) transforming the CQA of the affinity-purified NAP using a predetermined predictive model, wherein the predictive model is specific for one or more of the bioprocess unit operations within the multi-step bioprocess, and d) monitoring or controlling the bioprocess unit operation based on the predicted CQAs.

In another aspect of the disclosure, described herein is A method of developing a bioprocess for a NAP, the method comprising: a) processing the NAP using a bioprocess unit operation within the multi-step bioprocess, b) purifying the affinity-purified NAP from solution according to the method of claim 1, c) determining a critical quality attribute (CQA) of the NAP produced using the bioprocess unit operation, d) determining the CQA of the affinity-purified NAP, e) comparing the CQA of the affinity-purified NAP to the CQA of the NAP produced using the multi-step bioprocess, f) calculating a difference between the CQA of the affinity-purified NAP and the CQA of the NAP produced using the bioprocess unit operation, and g) developing the bioprocess by modifying the bioprocess unit operation based on the calculated difference in CQAs.

In yet another aspect of the disclosure, described herein is a method of developing a bioprocess for a NAP, the method comprising: a) processing the NAP using a bioprocess unit operation within the bioprocess, b) purifying the affinity-purified NAP from solution according to the method of claim 1, c) determining the CQA of the affinity-purified NAP, d) transforming the CQA of the affinity-purified NAP using a predetermined predictive model, wherein the predictive model is specific for one or more of the bioprocess unit operations within the multi-step bioprocess, and e) developing the multi-step bioprocess by modifying the bioprocess unit operation based on the predicted CQAs.

As used herein, the term "critical quality attribute", also referred to as "CQA", means a physical, chemical, biological, or microbiological property or characteristic that should be within an appropriate limit, range, or distribution to ensure the desired product quality. Non-limiting examples of CQAs include product purity, potency, charged isoform profile, post-translational modifications, oxidation, reductions, deamidation, adduct formation, clipped forms, enzymatic cleavage, specific activity, peptide map, dimer content, product aggregation, site specific glycosylation, total glycans, and/or glycosylation profile. The selection of appropriate CQAs and appropriate assays for specific applications of the disclosed methods are within the capabilities of one of ordinary skill in the art.

A critical quality attribute can be determined from a NAP sampled at many stages within a multi-step bioprocess. In another aspect of the disclosure, In one embodiment, the NAP is sampled immediately upstream of a particular bioprocess unit operation. In another embodiment, the NAP is sampled immediately downstream of the particular bioprocess unit operation. In another embodiment, the NAP is sampled both upstream and downstream of a particular bioprocess unit operation. In yet another embodiment, the NAP is sampled within a particular bioprocess unit operation at one or more timepoints.

In one aspect of the disclosure, the CQA of the NAP is determined at one or more timepoints within the multi-step bioprocess.

In one aspect of the disclosure, described herein is a method of predicting a critical quality attribute (CQA) of a non-antibody protein (NAP) produced by a bioprocess unit operation within a multi-step bioprocess. In one embodiment, the method comprises the following steps: a) purifying the affinity-purified NAP from solution according to the method of claim 1, b) determining the CQA of the affinity-purified NAP, c) transforming the CQA of the affinity-purified NAP using a predetermined predictive model, wherein the predictive model is specific for one or more of the bioprocess unit operations within the multi-step bioprocess, and d) predicting the CQA of the NAP produced by the bioprocess unit operation within a multi-step bioprocess based on the transformed CQA of the affinity-purified NAP.

In certain embodiments, the transformed CQA of affinity-purified NAP is substantially equivalent to the CQA of the NAP produced by a bioprocess unit operation within the multi-step bioprocess.

In certain embodiments, a CQA of a non-antibody protein is determined by measurement. In some such embodiments, a CQA is measured using a high-throughput and/or rapid analytical technique. In certain embodiments, a CQA is measured using an analytical technique comprising the following non-limiting examples: high-performance liquid chromatography (HPLC), differential refractometry, fluorescence, ultra-performance liquid chromatography (UPLC), multi-angle laser light scattering analysis (MALLS), mass spectroscopy, tandem mass spectroscopy, isoelectric focusing, and/or differential scanning calorimetry. In yet other embodiments, the high-throughput and/or rapid analytical technique is performed by a robot. In further embodiments, the robot is a liquid-handling robot.

In a certain embodiment, the affinity-purified NAP is evaluated by glycosylation profile analysis. As used herein. "glycosylation profile" means any method by which the glycosylation of a NAP is measured, including measurements of total content of individual glycans, relative quantitation of individual glycostructures, or absolute quantitation of individual glycostructures. Exemplary methods that can be used to perform glycosylation profile analysis are known in the art.

4. Chromatography

The processes described herein include the use of a chromatography column in a single-step purification process. The chromatography column that can be used for the disclosed method can have a resin volume of, e.g., at least about 50 µL, at least about 75 µL, at least about 100 µL, at least about 500 µL, at least about 1 mL, at least about 2 mL, at least about 5 mL, at least about 10 mL, at least about 15 mL, at least about 20 mL, at least about 25 mL, at least about 30 mL, at least about 35 mL, at least about 40 mL, at least about 45 mL, at least about 50 mL, at least about 55 mL, at least about 60 mL, at least about 65 mL, at least about 70 mL, at least about 75 mL, at least about 80 mL, at least about 85 mL, at least about 90 mL, at least about 95 mL, or at least about 100 mL. The chromatography column can have a resin volume of between about 2 mL to about 100 mL, between about 2 mL and about 90 mL, between about 2 mL and about 80 mL, between about 2 mL and about 70 mL, between about 2 mL and about 60 mL, between about 2 mL and about 50 mL, between about 5 mL and about 50 mL, between about 2 mL and about 45 mL, between about 5 mL and about 45 mL, between about 2 mL and about 40 mL, between about 5 mL and about 40 mL, between about 2 mL and about 35 mL, between about 5 mL and about 35 mL, between about 2 mL and about 30 mL, between about 5 mL and about 30 mL, between about 2 mL and about 25 mL, between about 5 mL and about 25 mL, between about 15 mL and about 60 mL, between about 10 mL and about 60 mL, between about 10 mL and about 50 mL, and between about 15 mL and about 50 mL. The flow rate used for the chromatography column in a single-step purification process can be, e.g., between about 0.2 ml/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, between about 1.0 mL/minute and about 15.0 mL/minute).

The chromatographic membrane that can be present in a single step purification method can have a bed volume of, e.g., between about 1 mL to about 500 mL (e.g., between about 1 mL to about 475 mL, between about 1 mL to about 450 mL, between about 1 mL to about 425 mL, between about 1 mL to about 400 mL, between about 1 mL to about 375 mL, between about 1 mL to about 350 mL, between about 1 mL to about 325 mL, between about 1 mL to about 300 mL, between about 1 mL to about 275 mL, between about 1 mL to about 250 mL, between about 1 mL to about 225 mL, between about 1 mL to about 200 mL, between about 1 mL to about 175 mL, between about 1 mL to about 150 mL, between about 1 mL to about 125 mL, between about 1 mL to about 100 mL, between about 2 mL to about 100 mL, between about 5 mL to about 100 mL, between about 1 mL to about 80 mL, between about 2 mL to about 80 mL, between about 5 mL to about 80 mL, between about 1 mL to about 60 mL, between about 2 mL to about 60 mL, between about 5 mL to about 60 mL, between about 1 mL to about 40 mL, between about 2 mL to about 40 mL, between about 5 mL to about 40 mL, between about 1 mL to about 30 mL, between about 2 mL to about 30 mL, between about 5 mL to about 30 mL, between about 1 mL and about 25 mL, between about 2 mL and about 25 mL, between about 1 mL and about 20 mL, between about 2 mL and about 20 mL, between about 1 mL and about 15 mL, between about 2 mL and about 15 mL, between about 1 mL and about 10 mL, or between about 2 mL and about 10 mL.

One or more (e.g., three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) different types of buffer can be employed during the use of the single-step purification method in any of the processes described herein. As is known in the art, the one or more types of butter used in the in the processes described herein will depend on the resin present in the chromatography column or the chromatographic membrane of the chromatography column, the non-antibody protein, and unit operation (e.g., any of the exemplary unit operations described herein) performed by the specific chromatography column or chromatography membrane of the single-step purification method. The volume and type of buffer employed during the use of the chromatography column in any of the processes described herein can also be determined by one skilled in the art (e.g., as discussed in more detail below). For example, the volume and type(s) of buffer employed during the use of the chromatography column in any of the processes described herein can be chosen in order to optimize one or more of the following non-antibody protein product: the overall yield of non-antibody protein, the activity of the non-antibody protein, the level of purity of the non-antibody protein, and the removal of biological contaminants from a fluid containing the non-antibody protein (e.g., absence of active viruses, mycobacteria, yeast, bacteria, or mammalian cells).

The one or more unit operations that can be performed in the presently described processes include, for example, capturing the non-antibody protein, inactivating viruses present in a fluid containing the non-antibody protein, purifying the non-antibody protein, holding a fluid containing the non-antibody protein, filtering or removing particulate material and/or cells from a fluid containing the non-antibody protein, and adjusting the ionic concentration and/or pH of a fluid containing the non-antibody protein.

The unit operation of recovering can be performed using the single-step purification disclosed herein, that contains a chromatography column or chromatography resin, e.g., that utilizes a recovery mechanism. Non-limiting examples of recovery mechanisms include a protein A-binding recovery mechanism, an antibody- or antibody fragment-binding recovery mechanism, a substrate-binding recovery mechanism, an aptamer-binding recovery mechanism, a tag-binding recovery mechanism (e.g., poly-His tag-based recovery mechanism), and a cofactor-binding recovery mechanism. Capturing can also be performed using a resin that can be used to perform cation exchange or anion exchange chromatography, or molecular sieve chromatography. Non-limiting resins that can be used to recover a non-antibody protein are described herein. Additional examples of resins that can be used to recover a non-antibody protein are known in the art.

The unit operation of purifying a non-antibody protein can be performed using a chromatography column or chromatographic membrane that contains a resin, e.g., that utilizes a recovery system. Non-limiting examples of recovery mechanisms include a protein A-binding recovery mechanism, an antibody- or antibody fragment-binding recovery mechanism, a substrate-binding recovery mechanism, an aptamer-binding recovery mechanism, a tag-binding recovery mechanism (e.g., poly-His tag-based recovery mechanism), and a cofactor-binding recovery mechanism. Purifying can also be performed using a resin that can be used to perform cation exchange or anion exchange chromatography, or molecular sieve chromatography. Non-limiting resins that can be used to purify a non-antibody protein are described herein. Additional examples of resins that can be used to purify a non-antibody protein are known in the art.

The unit operation of holding a fluid containing the non-antibody protein can be performed using at least one reservoir (e.g., a break tank). For example, the reservoir that can be used to achieve this unit operation can have a volume of between about 1 mL to about 1 L (e.g., between about 1 mL to about 800 mL, between about 1 mL to about 600 mL, between about 1 mL to about 500 mL, between about 1 mL to about 400 mL, between about 1 mL to about 350 mL, between about 1 mL to about 300 mL, between about 10 mL and about 250 mL, between about 10 mL and about 200 mL, between about 10 mL and about 150 mL, and between about 10 mL to about 100 mL). The reservoir (e.g., break tank) can hold the fluid containing the non-antibody protein for at least 10 minutes (e.g., at least 20 minutes, at least 30 minutes, at least 1 hour, at least 2 hours, at least 4 hours, or at least 6 hours). The reservoir can be used to both hold and refrigerate (e.g., at a temperature of less than 25° C., less than 15° C., or less than 10° C.) the fluid containing the non-antibody protein. The reservoir can have any shape, including a circular cylinder, an oval cylinder, or an approximately rectangular sealed and nonpermeable bag.

The unit operations of filtering a fluid containing the non-antibody protein can be performed using a filter, or a chromatography column or chromatographic membrane that contains a molecule sieve resin. As is known in the art, a wide variety of submicron filters (e.g., a filter with a pore size of less than 1 µm, less than 0.5 µm, less than 0.3 µm, about 0.2 µm, less than 0.2 µm, less than 100 nm, less than 80 nm, less than 60 nm, less than 40 nm, less than 20 nm, or less than 10 nm) are available in the art that are capable of removing any precipitated material and/or cells (e.g., precipitated, unfolded protein; precipitated, unwanted host cell proteins; precipitated lipids; bacteria; yeast cells; fungal cells; mycobacteria; and/or mammalian cells). Filters having a pore size of about 0.2 µm or less than 0.2 µm are known to effectively remove bacteria from the fluid containing the non-antibody protein. As is known in the art, a chromatography column or a chromatographic membrane containing a molecular sieve resin can also be used to perform the unit operation of filtering a fluid containing a non-antibody protein.

The unit operations of adjusting the ionic concentration and/or pH of a fluid containing the non-antibody protein can be performed using a buffer adjustment reservoir (e.g., an in-line buffer adjustment reservoir) that adds a new buffer solution into a fluid that contains the non-antibody protein before the fluid containing the non-antibody protein is fed into the chromatography column. As can be appreciated in the art, the in-line buffer adjustment reservoir can be any size (e.g., greater than 100 mL) and can contain any buffered solution (e.g., a buffered solution that has one or more of: an increased or decreased pH as compared to the fluid containing the non-antibody protein, a an increased or decreased ionic (e.g., salt) concentration compared to the fluid containing the non-antibody protein, and/or an increased or decreased concentration of an agent that competes with the non-antibody protein for binding to resin present in the chromatographic column or chromatographic membrane).

5. Recovering the Non-Antibody Protein

The present processes include a step of recovering a non-antibody protein. As can be appreciated in the art, the liquid culture medium containing the non-antibody protein can be continuously fed onto the chromatography column using a variety of different means. For example, the liquid culture medium can be actively pumped into the chromatography column or the liquid culture medium can be fed into chromatography column using gravitational force. The liquid culture medium can be stored in a reservoir (e.g., a holding tank) before it is fed into the chromatography column or the liquid culture medium can be actively pumped from a bioreactor containing a culture of cells (e.g., cells that secrete the non-antibody protein into the culture medium) into the chromatography column.

The liquid culture medium can be fed (loaded) into the chromatography column at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, between about 1.0 mL/minute and about 15.0 mL/minute). The liquid culture medium containing the non-antibody protein can be derived from any of the exemplary sources described herein or known in the art.

Some examples further include the optional step of filtering the liquid culture medium before it is fed onto the chromatography column. Any of the exemplary means of filtering a liquid culture medium or a fluid containing the non-antibody protein described herein, or any filtration means known in the art, can be used to filter the liquid culture medium containing the non-antibody protein before it is fed into the chromatography column.

In the methods described herein, the capturing of the non-antibody protein from the liquid culture medium is performed using a chromatography column. As can be appreciated in the art, in order to achieve the recovery of the non-antibody protein, the chromatographic column or chromatographic membrane must contain a resin that utilizes a recovering mechanism (e.g., any of the exemplary recovery mechanisms described herein). For example, if the non-antibody protein is an antibody or an antibody fragment, the recovering system can be a protein A-binding recovering mechanism or an antigen-binding recovering mechanism (where the recovering antigen is specifically recognized by the non-antibody antibody or antibody fragment). If the non-antibody protein is an enzyme, the recovering mechanism can use an antibody or antibody fragment that specifically binds to the enzyme to recovery the non-antibody enzyme, a substrate of the enzyme to recovery the non-antibody enzyme, a cofactor of the enzyme to recovery the non-antibody enzyme, or, if the non-antibody enzyme contains a tag, a protein, metal chelate, or antibody (or antibody fragment) that specifically binds to the tag present in the non-antibody enzyme. Non-limiting resins that can be used to recovery a non-antibody protein are described herein and additional resins that can be used to recovery a non-antibody protein are known in the art. One non-limiting example of resin that utilizes a protein A-binding recovery mechanism is MabSelect Sure resin (GE Healthcare, Piscataway, N.J.).

Exemplary non-limiting sizes and shapes of the chromatography column or chromatographic membrane that can be used to recovery the non-antibody protein are described herein. The liquid culture medium fed (loaded) into the chromatography column can contain, e.g., between about 0.05 mg/mL to about 100 mg/mL non-antibody protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, or between about 0.5 mg/mL to about 10 mg/mL non-antibody protein). The mean time required for the non-antibody protein to bind to the resin used to perform the unit operation of recovery can be, e.g., between about 5 seconds to about 10 minutes (e.g., between about 10 seconds to about 8 minutes, between about 10 seconds to about 7 minutes, between about 10 seconds to about 6 minutes, between about 10 seconds to about 5 minutes, between about 30 seconds to about 5 minutes, between about 1 minute to about 5 minutes, between about 10 seconds to about 4 minutes, between about 30 seconds to about 4 minutes, or between about 1 minute to about 4 minutes).

As can be appreciated in the art, in order to recover the non-antibody protein using the chromatography column or chromatographic membrane, one must perform the sequential chromatographic steps of loading, washing, eluting, and regenerating the chromatography column or chromatography membrane. Any of the exemplary flow rates, buffer volumes, and/or lengths of time allotted for each sequential chromatographic step described herein can be used in the one or more of these different sequential chromatographic steps (e.g., one or more of the sequential chromatographic steps of loading, washing, eluting, and regenerating the chromatography column or chromatography membrane that are used for capturing the non-antibody protein). Non-limiting flow rates, buffer volumes, and/or lengths of time allotted for each sequential chromatographic step that can be used for recovery chromatographic column or chromatographic membrane are provided below. In addition, exemplary buffers elution buffers that can be used are described below.

The chromatographic column or chromatographic membrane containing a resin that can perform the unit operation of capturing (e.g., any of exemplary resins that can be used for capturing described herein) can be loaded with the liquid culture medium containing a non-antibody protein using any of loading flow rates (feed rates) described above. In some examples, a single chromatographic column or single chromatographic membrane containing a resin that is capable of performing the unit operation of capturing is loaded in, e.g., between about 10 minutes to about 90 minutes (e.g., between about 15 minutes and about 90 minutes, between about 20 minutes and 80 minutes, between about 30 minutes and 80 minutes, between about 40 minutes and about 80 minutes, between about 50 minutes and about 80 minutes, and between about 60 minutes and 80 minutes).

Following the loading of the non-antibody protein onto the chromatographic column or chromatographic membrane that contains a resin that is capable of performing the unit operation of recovery, the chromatographic column or chromatographic membrane is washed with at least one washing buffer. As can be appreciated in the art, the at least one (e.g., two, three, or four) washing buffer is meant to elute all proteins that are not the non-antibody protein from the chromatography column or chromatographic membrane, while not disturbing the interaction of the non-antibody protein with the resin.

The wash buffer can be passed through the chromatography column or chromatographic membrane at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, between about 1.0 mL/minute and about 15.0 mL/minute). The volume of wash buffer used (e.g., combined total volume of wash buffer used when more than one wash buffer is used) can be, e.g., between about 1× column volume (CV) to about 15×CV (e.g., between about 1×CV to about 14×CV, about 1×CV to about 13×CV, about 1×CV to about 12×CV, about 1×CV to about 11×CV, about 2×CV to about 1×CV, about 3×CV to about 11×CV, about 4×CV to about 11×CV, about 5×CV to about 11×CV, or about 5×CV to about 10×CV). The total time of the washing can be, e.g., between about 2 minutes to about 3 hours (e.g., between about 2 minutes to about 2.5 hours, between about 2 minutes to about 2.0 hours, between about 5 minutes to about 1.5 hours, between about 10 minutes to about 1.5 hours, between about 10 minutes to about 1.25 hours, between about 20 minutes to about 1.25 hours, or between about 30 minutes to about 1 hour).

Following the washing of the chromatographic column or chromatographic membrane that contains a resin that is capable of performing the unit operation of recovery, the non-antibody protein is eluted from the chromatographic column or chromatographic membrane by passing an elution buffer through the chromatographic column or chromatographic membrane that contains a resin that is capable of performing the unit operation of capturing. The elution buffer can be passed through the chromatography column or chromatographic membrane that contains a resin that is capable of performing the unit operation of recovery at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 1.0 mL/minute and about 15.0 mL/minute). The volume of elution buffer used to elute the non-antibody protein from each of the chromatographic column or chromatographic membrane that contains a resin that is capable of performing the unit operation of purifying can be, e.g., between about 1× column volume (CV) to about 15×CV (e.g., between about 1×CV to about 14×CV, about 1×CV to about 13×CV, about 1×CV to about 12×CV, about 1×CV to about 1×CV, about 2×CV to about 11×CV, about 3×CV to about 1×CV, about 4×CV to about 1×CV, about 5×CV to about 1×CV, or about 5×CV to about 10×CV). The total time of the eluting can be, e.g., between about 2 minutes to about 3 hours (e.g., between about 2 minutes to about 2.5 hours, between about 2 minutes to about 2.0 hours, between about 2 minutes to about 1.5 hours, between about 2 minutes to about 1.5 hours, between about 2 minutes to about 1.25 hours, between about 2 minutes to about 1.25 hours, between about 2 minutes to about 1 hour, between about 2 minutes and about 40 minutes, between about 10 minutes and about 40 minutes, between about 20 minutes and about 40 minutes). Non-limiting examples of elution buffers that can be used in these methods will depend on the recovery mechanism and/or the non-antibody protein. For example, an elution buffer can contain a different concentration of salt (e.g., increased salt concentration), a different pH (e.g., an increased or decreased salt concentration), or a molecule that will compete with the non-antibody protein for binding to the resin that is capable of performing the unit operation of capturing. Examples of such elution buffers for each exemplary recovery mechanism described herein are well known in the art.

Following the elution of the non-antibody protein from the chromatographic column or chromatographic membrane that contains a resin that is capable of performing the unit operation of recovery, and before the next volume of liquid culture medium can be loaded onto the chromatographic column or chromatographic membrane, the chromatography column or chromatographic membrane must be equilibrated using an regeneration buffer. The regeneration buffer can be passed through the chromatography column or chromatographic membrane that contains a resin that is capable of performing the unit operation of recovery at a flow rate of, e.g., between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 5.0 mL/minute to about 15.0 ml/minute, or between about 1.0 mL/minute and about 15.0 mL/minute). The volume of regeneration buffer used to equilibrate the chromatography column or chromatographic membrane that contains a resin that is capable of performing the unit operation of recovery can be, e.g., between about 1× column volume (CV) to about 15×CV (e.g., between about 1×CV to about 14×CV, about 1×CV to about 13×CV, about 1×CV to about 12×CV, about 1×CV to about 11×CV, about 2×CV to about 11×CV, about 3×CV to about 11×CV, about 2×CV to about 5×CV, about 4×CV to about 11×CV, about 5×CV to about 11×CV, or about 5×CV to about 10×CV).

In some of the processes described herein, the single-step purification process contains a reservoir that inactivates the viruses present in a fluid containing the non-antibody protein. Non-limiting examples of reservoirs that can be used to perform the unit operation of inactivation of viruses present in a fluid containing the non-antibody protein are described herein.

Some processes described herein can further include a step of adjusting the ionic concentration and/or pH of the eluate from the chromatography column. As described herein, the ionic concentration and/or pH of the eluate can be adjusted by adding a buffer to the eluate (e.g., through the use of an in-line buffer adjustment reservoir). The buffer can be added to the eluate at a flow rate of, e.g., between about 0.1 mL/minute to about 15 mL/minute (e.g., between about 0.1 mL/minute to about 12.5 mL/minute, between about 0.1 mL/minute to about 10.0 mL/minute, between about 0.1 mL/minute to about 8.0 mL/minute, between about 0.1 mL/minute to about 6 mL/minute, between about 0.1 mL/minute to 4 mL/minute, or between about 0.5 mL/minute to about 5 mL/minute).

6. Purifying the Non-Antibody Protein

The processes described herein include a step of purifying the non-antibody protein using a chromatography column or chromatographic membrane that can be used to perform the unit operation of purifying a non-antibody protein.

The chromatography column or chromatographic membrane that can be used to perform the unit operation of purifying the non-antibody protein can contain a resin that utilizes a recovery mechanism (e.g., any of the recovery mechanisms described herein or known in the art), or a resin that can be used to perform anion exchange, cation exchange, or molecular sieve chromatography. The size, shape, and volume of the chromatography column or chromatography membrane that can be used to perform the unit of operation of purifying the non-antibody protein can be any of combination of the exemplary sizes, shapes, and volumes of chromatography columns or chromatographic membranes described herein. As can be appreciated by one skilled in the art, the step of purifying a non-antibody protein can, e.g., include the steps of loading, washing, eluting, and equilibrating one chromatography column or chromatographic membrane used to perform the unit of operation of purifying the non-antibody protein. Typically, the elution buffer coming out of a chromatography column or chromatographic membrane used to perform the unit operation of purifying contains the non-antibody protein.

For example, the size of the chromatography column or chromatographic membrane that can be used to perform the unit operation of purifying the non-antibody protein can have a volume of, e.g., between about 2.0 mL to about 200 mL (e.g., between about 2.0 mL to about 180 mL, between about 2.0 mL to about 160 mL, between about 2.0 mL to about 140 mL, between about 2.0 mL, to about 120 mL, between about 2.0 mL, to about 100 mL, between about 2.0 mL to about 80 mL, between about 2.0 mL to about 60 mL, between about 2.0 mL to about 40 mL, between about 5.0 mL to about 40 mL, between about 2.0 mL to about 30 mL, between about 5.0 mL to about 30 mL, or between about 2.0 mL to about 25 mL). The flow rate of the fluid containing the non-antibody protein as it is loaded onto the chromatography column or chromatographic that can be used to perform the unit operation of purifying the non-antibody protein can be, e.g., between about 0.1 mL/minute to about 25 mL/minute (e.g., between about 0.1 mL/minute to about 12.5 mL/minute, between about 0.1 mL/minute to about 10.0 mL/minute, between about 0.1 mL/minute to about 8.0 mL/minute, between about 0.1 mL/minute to about 6 mL/minute, between about 0.1 mL/minute to 4 mL/minute, between about 0.1 mL/minute to about 3 mL/minute, between about 0.1 mL/minute to about 2 mL/minute, or about 0.2 mL/minute to about 4 mL/minute). The concentration of the non-antibody protein in the fluid loaded onto the one chromatography column or chromatographic membrane that can be used to perform the unit operation of purifying the non-antibody protein can be, e.g., between about 0.05 mg/mL to about 100 mg/mL non-antibody protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, or between about 0.5 mg/mL to about 10 mg/mL non-antibody protein). The resin in the chromatography column or chromatographic membrane used to perform the unit operation of purifying can be a resin that can be used to perform anion exchange or cation exchange chromatography. The resin in the chromatography column or chromatographic membrane that is used to perform the unit operation of purifying can be a cationic exchange resin (e.g., Capto-S resin, GE Healthcare Life Sciences, Piscataway, N.J.).

Following the loading of the non-antibody protein onto the chromatographic column or chromatographic membrane that can be used to perform the unit operation of purifying the non-antibody protein, the chromatographic column or chromatographic membrane is washed with at least one washing buffer. As can be appreciated in the art, the at least one (e.g., two, three, or four) washing buffer is meant to elute all proteins that are not the non-antibody protein from the chromatography column or chromatographic membrane, while not disturbing the interaction of the non-antibody protein with the resin or otherwise eluting the non-antibody protein.

The wash buffer can be passed through the chromatography column or chromatographic membrane at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL minute and about 14 mL/minute, between about 1.0 mL/minute and about 25.0 mL/minute, between about 1.0 mL/minute and about 15.0 mL/minute). The volume of wash buffer used (e.g., combined total volume of wash buffer used when more than one wash buffer is used) can be, e.g., between about 1× column volume (CV) to about 15×CV (e.g., between about 1×CV to about 14×CV, about 1×CV to about 13×CV, about 1×CV to about 12×CV, about 1×CV to about 1×CV, about 2×CV to about 1 i×CV, about 3×CV to about 11×CV, about 4×CV to about 11×CV, about 2.5×CV to about 5.0×CV, about 5×CV to about 11×CV, or about 5×CV to about 10×CV). The total time of the washing can be, e.g., between about 2 minutes to about 3 hours (e.g., between about 2 minutes to about 2.5 hours, between about 2 minutes to about 2.0 hours, between about 5 minutes to about 1.5 hours, between about 10 minutes to about 1.5 hours, between about 10 minutes to about 1.25 hours, between about 20 minutes to about 1.25 hours, between about 30 minutes to about 1 hour, between about 2 minutes and 10 minutes, between about 2 minutes and 15 minutes, or between about 2 minutes and 30 minutes).

Following the washing of the chromatographic column or chromatographic membrane that can be used to perform the unit operation of purifying the non-antibody protein, the non-antibody protein is eluted from the chromatographic column or chromatographic membrane by passing an elution buffer through the chromatographic column or chromatographic membrane that can be used to perform the unit operation of purifying the non-antibody protein. The elution buffer can be passed through the one chromatography column or chromatographic membrane that can be used to perform the unit operation of purifying the non-antibody protein at a flow rate of between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 1.0 mL/minute and about 15.0 mL/minute). The volume of elution buffer used to elute the non-antibody protein from the chromatographic column or chromatographic membrane that can be used to perform the unit operation of purifying the non-antibody protein can be, e.g., between about 1×column volume (CV) to about 25×CV (e.g., between about 1×CV to about 20×CV, between about 15×CV and about 25×CV, between about 1×CV to about 14×CV, about 1×CV to about 13×CV, about 1×CV to about 12×CV, about 1×CV to about 11×CV, about 2×CV to about 11×CV, about 3×CV to about 11×CV, about 4×CV to about 11×CV, about 5×CV to about 11×CV, or about 5×CV to about 10×CV). The total time of the eluting can be, e.g., between about 2 minutes to about 3 hours (e.g., between about 2 minutes to about 2.5 hours, between about 2 minutes to about 2.0 hours, between about 2 minutes to about 1.5 hours, between about 2 minutes to about 1.5 hours, between about 2 minutes to about 1.25 hours, between about 2 minutes to about 1.25 hours, between about 2 minutes to about 1 hour, between about 2 minutes and about 40 minutes, between about 10 minutes and about 40 minutes, between about 20 minutes and about 40 minutes, or between about 30 minutes and 1.0 hour). Non-limiting examples of elution buffers that can be used in these methods will depend on the resin and/or the non-antibody protein. For example, an elution buffer can contain a different concentration of salt (e.g., increased salt concentration), a different pH (e.g., an increased or decreased salt concentration), or a molecule that will compete with the non-antibody protein for binding to the resin. Examples of such elution buffers for each of the exemplary recovery mechanisms described herein are well known in the art.

Following the elution of the non-antibody protein from the chromatographic column or chromatographic membrane that can be used to perform the unit operation of purifying the non-antibody protein, and before the next volume of fluid containing a non-antibody protein can be loaded onto the chromatographic column or chromatographic membrane, the chromatography column or chromatographic membrane must be equilibrated using an regeneration buffer. The regeneration buffer can be passed through the chromatography column or chromatographic membrane that can be used to perform the unit operation of purifying the non-antibody protein at a flow rate of, e.g., between about 0.2 mL/minute to about 25 mL/minute (e.g., between about 0.2 mL/minute to about 20 mL/minute, between about 0.5 mL/minute to about 20 mL/minute, between about 0.2 mL/minute to about 15 mL/minute, between about 0.5 mL/minute to about 15 mL/minute, between about 0.5 mL/minute to about 10 mL/minute, between about 0.5 mL/minute and about 6.0 mL/minute, between about 1.0 mL/minute and about 5.0 mg/minute, between about 0.5 mL minute and about 14 mL/minute, between about 1.0 mL/minute and about 25.0 mL/minute, between about 5.0 mL/minute to about 15.0 mL/minute, or between about 1.0 mL/minute and about 15.0 mL/minute). The volume of regeneration buffer used to equilibrate the chromatography column or chromatographic membrane that contains a resin that can be used to perform the unit operation of purifying the non-antibody protein can be, e.g., between about 1× column volume (CV) to about 15×CV (e.g., between about 1×CV to about 14×CV, between about 1×CV to about 13×CV, between about 1×CV to about 12×CV, between about 1×CV to about 11×CV, between about 2×CV to about 11×CV, between about 3×CV to about 11×CV, between about 2×CV to about 5×CV, between about 2.5×CV to about 7.5×CV, between about 4×CV to about 11×CV, between about 5×CV to about 11×CV, or between about 5×CV to about 10×CV). The concentration of non-antibody protein in the eluate of the chromatography column or chromatographic membrane that can be used to perform the unit operation of purifying the non-antibody protein can be, e.g., between about 0.05 mg/mL to about 100 mg/mL non-antibody protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 2.5 mg/mL and about 7.5 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, or between about 0.5 mg/mL to about 10 mg/mL non-antibody protein).

7. Culturing Methods

Some of the processes described herein further include a step of culturing cells (that secrete a non-antibody protein in a bioreactor (e.g., a perfusion or feed-batch bioreactor) that contains a liquid culture medium, wherein a volume of the liquid culture medium that is substantially free of cells is continuously or periodically removed from the perfusion bioreactor and fed into the chromatography column. The bioreactor can have a volume of, e.g., between about 1 L to about 10,000 L (e.g., between about 1 L to about 50 L, between about 50 L to about 500 L, between about 500 L to about 1000 L, between 500 L to about 5000 L, between about 500 L to about 10.000 L, between about 5000 L to about 10,000 L, between about 1 L and about 10,000 L, between about IL and about 8,000 L, between about 1 L and about 6,000 L, between about 1 L and about 5,000 L, between about 100 L and about 5,000 L, between about 10 L and about 100 L, between about 10 L and about 4,000 L, between about 10 L and about 3,000 L, between about 10 L and about 2,000 L, or between about 10 L and about 1,000 L). The amount of liquid culture medium present in a bioreactor can be, e.g., between about between about 0.5 L to about 5,000 L (e.g., between about 0.5 L to about 25 L, between about 25 L to about 250 L, between about 250 L to about 500 L, between 250 L to about 2500 L, between about 250 L to about 5,000 L, between about 2500 L to about 5,000 L, between about 0.5 L and about 5,000 L, between about 0.5 L and about 4,000 L, between about 0.5 L and about 3,000 L, between about 0.5 L and about 2,500 L, between about 50 L and about 2,500 L, between about 5 L and about 50 L, between about 5 L and about 2,000 L, between about 5 L and about 1,500 L, between about 5 L and about 1,000 L, or between about 5 L and about 500 L). Culturing cells can be performed, e.g., using a batch-feed bioreactor or a perfusion bioreactor. Non-limiting examples and different aspects of culturing cells are described below and can be used in any combination.

8. Cells

The cells that are cultured in some of the processes described herein can be bacteria (e.g., gram negative bacteria), yeast (e.g., *Saccharomyces cerevisiae, Pichia pastoris, Hansenula polymorpha, Kluvveromyces lactis, Schizosaccharomyces pombe, Yarrowia lipolytica,* or *Arxula adeninivorans*), or mammalian cells. The mammalian cell can be a cell that grows in suspension or an adherent cell. Non-limiting examples of mammalian cells that can be cultured in any of the processes described herein include: Chinese hamster ovary (CHO) cells (e.g., CHO DG44 cells or CHO-K Is cells), Sp2.0, myeloma cells (e.g., NS/0), B-cells, hybridoma cells, T-cells, human embryonic kidney (HEK) cells (e.g., HEK 293E and HEK 293F), African green monkey kidney epithelial cells (Vero) cells, and Madin-Darby Canine (Cocker Spaniel) kidney epithelial cells (MDCK) cells. In some examples where an adherent cell is cultured, the culture can also contain a plurality of microcarriers (e.g., microcarriers that contain one or more pores). Additional mammalian cells that can be cultured in any of the processes described herein are known in the art.

The mammalian cell can contain a recombinant nucleic acid (e.g., a nucleic acid stably integrated in the mammalian cell's genome) that encodes a non-antibody protein. Non-limiting examples of recombinant nucleic acids that encode exemplary non-antibody proteins are described below, as are non-antibody proteins that can be produced using the methods described herein. In some instances, the mammalian cell that is cultured in a bioreactor (e.g., any of the bioreactors described herein) was derived from a larger culture.

A nucleic acid encoding a non-antibody protein can be introduced into a mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid that encodes a non-antibody protein is not stably integrated into a chromosome of the mammalian cell (transient transfection), while in others the nucleic acid is integrated. Alternatively or in addition, the nucleic acid encoding a non-antibody protein can be present in a plasmid and/or in a mammalian artificial chromosome (e.g., a human artificial chromosome). Alternatively or in addition, the nucleic acid can be introduced into the cell using a viral vector (e.g., a lentivirus, retrovirus, or adenovirus vector). The nucleic acid can be operably linked to a promoter sequence (e.g., a strong promoter, such as a β-actin promoter and CMV promoter, or an inducible promoter). A vector containing the nucleic acid can, if desired, also contain a selectable marker (e.g., a gene that confers hygromycin, puromycin, or neomycin resistance to the mammalian cell).

In some instances, the non-antibody protein is a secreted protein and is released by the mammalian cell into the extracellular medium (e.g., the first and/or second liquid culture medium). For example, a nucleic acid sequence encoding a soluble non-antibody protein can contain a sequence that encodes a secretion signal peptide at the N- or C-terminus of the non-antibody protein, which is cleaved by an enzyme present in the mammalian cell, and subsequently released into the extracellular medium (e.g., the first and/or second liquid culture medium).

9. Culture Media

Liquid culture media are known in the art. The liquid culture media (e.g., a first and/or second tissue culture medium) can be supplemented with a mammalian serum (e.g., fetal calf serum and bovine serum), and/or a growth hormone or growth factor (e.g., insulin, transferrin, and epidermal growth factor). Alternatively or in addition, the liquid culture media (e.g., a first and/or second liquid culture medium) can be a chemically-defined liquid culture medium, an animal-derived component free liquid culture medium, a serum-free liquid culture medium, or a serum-containing liquid culture medium. Non-limiting examples of chemically-defined liquid culture media, animal-derived component free liquid culture media, serum-free liquid culture media, and serum-containing liquid culture media are commercially available.

A liquid culture medium typically contains an energy source (e.g., a carbohydrate, such as glucose), essential amino acids (e.g., the basic set of twenty amino acids plus cysteine), vitamins and/or other organic compounds required at low concentrations, free fatty acids, and/or trace elements. The liquid culture media (e.g., a first and/or second liquid culture medium) can, if desired, be supplemented with, e.g., a mammalian hormone or growth factor (e.g., insulin, transferrin, or epidermal growth factor), salts and buffers (e.g., calcium, magnesium, and phosphate salts), nucleosides and bases (e.g., adenosine, thymidine, and hypoxanthine), protein and tissue hydrolysates, and/or any combination of these additives.

A wide variety of different liquid culture media that can be used to culture cells in any of the methods described herein are known in the art. Medium components that also may be useful in the present processes include, but are not limited to, chemically-defined (CD) hydrolysates, e.g., CD peptone, CD polypeptides (two or more amino acids), and CD growth factors. Additional examples of liquid tissue culture medium and medium components are known in the art.

Skilled practitioners will appreciate that the first liquid culture medium and the second liquid culture medium described herein can be the same type of media or different media.

10. Additional Features of Exemplary Bioreactors

The interior surface of any of the bioreactors described herein may have at least one coating (e.g., at least one coating of gelatin, collagen, poly-L-ornithine, polystyrene, and laminin), and as is known in the art, one or more ports for the sparging of $O_2$, $CO_2$, and $N_2$ into the liquid culture medium, and a stir mechanism for agitating the liquid culture medium. The bioreactor can incubate the cell culture in a controlled humidified atmosphere (e.g., at a humidity of greater than 20%, 30%, 40%, 50%, 60%, 70%, 75%, 80%, 85%, 90%, or 95%, or a humidity of 100%). The bioreactor can also be equipped with a mechanical device that is capable of removing a volume of liquid culture medium from the bioreactor and optionally, a filter within the mechanical device that removes the cells from the liquid culture medium during the process of transfer of the liquid culture medium out of the bioreactor (e.g., an ATF system).

11. Temperature

The step of culturing of mammalian cells can be performed at a temperature of about 31° C. to about 40° C. Skilled practitioners will appreciate that the temperature can be changed at specific time point(s) in during the culturing step, e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days, or more after the initial seeding of the bioreactor with the cell. For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.). For example, the temperature can be shifted downwards (e.g., a change of up to or about 0.1, 0.2, 0.3, 0.4, 0.5, 0.6, 0.7, 0.8.0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.).

12. $CO_2$

The culturing step described herein can further include exposing the liquid culture medium in the bioreactor to an atmosphere containing at most or about 15% $CO_2$ (e.g., at most or about 14% $CO_2$, 12% $CO_2$, 10% $CO_2$, 8% $CO_2$, 6% $CO_2$, 5% $CO_2$, 4% $CO_2$, 3% $CO_2$, 2% $CO_2$, or at most or about 1% $CO_2$).

13. Perfusion Bioreactor

The culturing step described herein can be performed using a perfusion bioreactor. Culturing a cell in a perfusion bioreactor includes the removal from the bioreactor of a first volume of a first liquid culture medium (e.g., containing any concentration of cells, e.g., a first volume of a first liquid culture medium that is substantially free of cells), and adding to the first liquid culture medium a second volume of a second liquid culture medium. Removal and adding can be performed simultaneously or sequentially, or a combination of the two. Further, removal and adding can be performed continuously (e.g., at a rate that removes and replaces a volume of between 0.1% to 800% (e.g., between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, and between 4% and 30%) of the volume of the bioreactor or the first liquid culture medium volume over any given time period (e.g., over a 24-hour period, over an incremental time period of about 1 hour to about 24 hours, or over an incremental time period of greater than 24 hours) or periodically (e.g., once every third day, once every other day, once a day, twice a day, three times a day, four times a day, or five times a day), or any combination thereof. Where performed periodically, the volume that is removed or replaced (e.g., within about a 24-hour period, within an incremental time period of about 1 hour to about 24 hours, or within an incremental time period of greater than 24 hours) can be, e.g., between 0.1% to 800% (e.g., between 1% and 700%, between 1% and 600%, between 1% and 500%, between 1% and 400%, between 1% and 300%, between 1% and 200%, between 1% and 100%, between 100% and 200%, between 5% and 150%, between 10% and 50%, between 15% and 40%, between 8% and 800%, and between 4% and 30%) of the volume of the bioreactor or the first liquid culture medium volume. The first volume of the first liquid culture medium removed and the second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the first volume of the first liquid culture medium is removed (volume/unit of time) and the rate at which the second volume of the second liquid culture medium is added (volume/unit of time) can be varied. The rate at which the first volume of the first liquid culture medium is removed (volume/unit of time) and the rate at which the second volume of the second liquid culture medium is added (volume/unit of time) can be about the same or can be different.

Alternatively, the volume removed and added can change (e.g., gradually increase) over each 24-hour period (or alternatively, an incremental time period of between 1 hour and about 24 hours or an incremental time period of greater than 24 hours) during the culturing period. For example the volume of the first liquid culture medium removed and the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the bioreactor volume or the first liquid culture medium volume to about 25% to about 150% of the bioreactor volume or the first liquid culture medium volume.

Skilled practitioners will appreciate that the first liquid culture medium and the second liquid culture medium can be the same type of media. In other instances, the first liquid culture medium and the second liquid culture medium can be different.

The first volume of the first liquid culture medium can be removed, e.g., by a mechanical system that can remove the first volume of the first liquid culture medium from the bioreactor (e.g., the first volume of the first liquid culture medium that is substantially free of cells from the bioreactor). Alternatively or in addition, the first volume of the first liquid culture medium can be removed by seeping or gravity flow of the first volume of the first liquid culture medium through a sterile membrane with a molecular weight cut-off that excludes the cell. The second volume of the second liquid culture medium can be added to the first liquid culture medium in an automated fashion, e.g., by perfusion pump.

In some instances, removing the first volume of the first liquid culture medium (e.g., a first volume of the first liquid culture medium that is substantially free of mammalian cells) and adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the bioreactor with a mammalian cell.

14. Feed-Batch Bioreactor

The culturing step described herein can be performed using a feed-batch bioreactor. Culturing a cell in a feed-batch bioreactor includes, over the majority of the culturing period, the addition (e.g., periodic or continuous addition) to the first liquid culture medium of a second volume of a second liquid culture medium. The adding of the second liquid culture medium can be performed continuously (e.g., at a rate that adds a volume of between 0.1% to 300% (e.g., between 1% and 250%, between 1% and 100%, between 100% and 200%, between 5% and 150%, between 10% and 50%, between 15% and 40%, between 8% and 80%, and between 4% and 30%) of the volume of the bioreactor or the first liquid culture medium volume over any given time period (e.g., over a 24-hour period, over an incremental time period of about 1 hour to about 24 hours, or over an incremental time period of greater than 24 hours) or periodically (e.g., once every third day, once every other day, once a day, twice a day, three times a day, four times a day, or five times a day), or any combination thereof. Where performed periodically, the volume that is added (e.g., within about a 24-hour period, within an incremental time period of about 1 hour to about 24 hours, or within an incremental time period of greater than 24 hours) can be, e.g., between 0.1% to 300% (e.g., between 1% and 200%, between 1% and 100%, between 100% and 200%, between 5% and 150%, between 10% and 50%, between 15% and 40%, between 8% and 80%, and between 4% and 30%) of the volume of the bioreactor or the first liquid culture medium volume. The second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the second volume of the second liquid culture medium is added (volume/unit of time) can be varied over the entire or part of the culturing period. For example, the volume of the second liquid culture medium added can change (e.g., gradually increase) over each 24-hour period (or alternatively, an incremental time period of between 1 hour and about 24 hours or an incremental time period of greater than 24 hours) during the culturing period. For example the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the bioreactor volume or the first liquid culture medium volume to about 25% to about 150% of the bioreactor volume or the first liquid culture medium volume. The rate at which the second volume of the second liquid culture medium is added (volume/unit of time) can be about the same over the entire or part of the culturing period.

Skilled practitioners will appreciate that the first liquid culture medium and the second liquid culture medium can be the same type of media. In other instances, the first liquid culture medium and the second liquid culture medium can be different. The volume of the second liquid culture medium can be added to the first liquid culture medium in an automated fashion, e.g., by perfusion pump.

In some instances, adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the bioreactor with a mammalian cell. The cell culture medium can be harvested at the end of culture period and used in any of the processes described herein. The cell culture medium can be harvested at one or more time points during the culturing period and used in any of the processes described herein.

Skilled practitioners will appreciate that any of the various culture parameters (e.g., containers, volumes, rates or frequencies of replacing culture volumes, agitation frequencies, temperatures, media, and $CO_2$ concentrations) can be used in any combination in to perform these methods. Further, any of the mammalian cells described herein or known in the art can be used to produce a recombinant protein.

The processes described herein can yield an increased amount of biotherapeutic protein in a single-step. For example, the processes described herein can yield greater than about 100 μg, greater than about 500 μg, greater than about 1 mg, greater than about 2 mg, greater than about 3 mg, greater than about 4 mg, greater than about 5 mg, greater than about 6 mg, greater than about 7 mg, greater than about 8 mg, greater than about 9 mg, up to 10 mg of protein.

The processes described herein can result in an increased percentage of recovery of the non-antibody protein (e.g., increased percentage of yield of the non-antibody protein present in the liquid culture medium in the therapeutic protein drug substance). For example, the present processes can result in a percentage yield of non-antibody protein of greater than about 70%, greater than about 80%, greater than about 82%, greater than about 84%, greater than about 86%, greater than about 88%, greater than about 90%, greater than about 92%, greater than about 94%, greater than about 96%, or greater than about 98%. The present processes can result in a percentage yield of between about 80% to about 90%, between about 82% to about 90%, between about 84% to about 90/o %, between about 84% to about 88%, between about 84% to about 94%, between about 82% to about 92%, or between about 85% to about 95%.

The concentration of non-antibody protein present in the therapeutic protein drug substance can be greater than about 1.0 mg/mL, greater than about 1.5 mg/mL, greater than about 2.0 mg/mL, greater than about 2.5 mg/mL, greater than about 3.0 mg/mL, greater than about 3.5 mg/mL, greater than about 4.0 mg/mL, greater than about 4.5 mg/mL, greater than about 5.0 mg/mL, greater than about 5.5 mg/mL, greater than about 6.0 mg/mL, greater than about 6.5 mg/mL, greater than about 7.0 mg/mL, greater than about 7.5 mg/mL, greater than about 8.0 mg/mL, greater than about 8.5 mg/mL, greater than about 9.0 mg/mL, greater than about 10.0 mg/mL, greater than about 12.5 mg/mL, or greater than about 15.0 mg/mL.

15. Other Embodiments of the Disclosure

In additional embodiments, disclosed herein is a method for purifying a non-antibody protein from solution comprising: a chromatography step wherein the solution is passed over an affinity construct comprising an affinity ligand-coupled solid support, wherein the affinity construct is associated with a bioprocess unit operation, and isolating the non-antibody protein from solution. In another embodiment, the steps of the method are performed by a high throughput, liquid handling robot. In one embodiment, the method additionally comprises the step of glycosylation profile analysis.

In one embodiment, the non-antibody protein is a biotherapeutic protein. In another embodiment, the affinity ligand is coupled to the solid support by formation of secondary amine, tertiary amine, amide, triazole, disulfide, or hydrazone bonds. In another embodiment, the ligand of the affinity ligand-coupled based solid support is a monoclonal antibody.

In another embodiment, the ligand of the affinity ligand-coupled based solid support is a polyclonal antibody. In another embodiment, the affinity ligand is an imiglucerase antibody, an agalsidase beta antibody, an alglucosidase alpha antibody or an acid sphingomyelinase antibody. In another embodiment, the ligand of the affinity ligand-coupled based solid support is an aptamer, small peptide, or antibody fragment. In another embodiment, the solid support is an agarose-based resin.

In another embodiment, the affinity construct is a packed column. In another embodiment, the affinity construct is a well-mixed suspension. In another embodiment, the affinity construct is a chromatography membrane. In another embodiment, the affinity construct is directly integrated with the bioprocess unit operation. In another embodiment, the affinity construct is integrated in an at-line mode with the bioprocess unit operation. In another embodiment, the affinity construct is integrated in an offline mode with the bioprocess unit operation.

In yet another embodiment, the solid support comprises non-agarose chromatography media, monoliths, or nanoparticles. In certain embodiments the nanoparticles are gold nanoparticles or magnetic nanoparticles.

In another embodiment, the non-antibody biotherapeutic protein is an enzyme, hormone, hematological factor, growth factor, or immunological factor. In another embodiment, the bioprocess unit operation is a bioreactor or capture chromatography apparatus.

In an additional embodiments, the method is used to monitor performance of the bioprocess unit operation function. In certain embodiments, the bioprocess unit operation facilitates least one of seed train and inoculation, bioreactor production or purification steps having low product purity eluates. In other certain embodiments a high-throughput and rapid analytical technique is used to monitor performance of the bioprocess unit function. In other certain embodiments, the analytical technique is at least one of high-performance liquid chromatography (HPLC), differential refractometry, fluorescence, ultra-performance liquid chromatography (UPLC), or multi-angle laser light scattering analysis (MALLS).

The Examples that follow are illustrative of specific embodiments of the invention, and various uses thereof. They are set forth for explanatory purposes only, and should not be construed as limiting the scope of the invention in any way.

EXAMPLES

Materials

Toyopearl AF-Tresyl-650 resin was obtained from Tosoh Bioscience (King of Prussia, Pa.) and AminoLink® Plus, CarboLink™, and SulfoLink® immobilization kits were obtained from Thermo Fisher Scientific (Rockford, Ill.). BakerBond speM disposable columns were obtained from Avantor Performance Materials (Center Valley, Pa.). Sodium cyanoborohydride was purchased from Thermo Fisher Scientific while all other chemicals were obtained from either Avantor or Sigma-Aldrich (St. Louis. Mo.).

Antibody Production and Purification

For Enzyme 1, two adult, female Nubian goats were immunized with Enzyme 1 emulsified in Complete Freund's adjuvant for the first injection and in Incomplete Freund's adjuvant for all subsequent injections. Antiserum was collected over a period of one year before the terminal bleed and collection. The experiments described herein were completed during the polyclonal production and were, therefore, not performed using material from the entire serum pool.

Antiserum was centrifuged for 30 minutes at 10,000 g and filtered using a 0.22 μm polyethersulfone (PES) vacuum filters (Corning, Tewksbury, Mass.) to remove lipids and other insoluble materials. All chromatography steps were performed using an AKTA Purifier (GE Healthcare, Piscataway, N.J.). The antiserum was diluted 1:1 (v/v) with equilibration buffer (20 mM phosphate, pH 7) and loaded onto a column packed with Protein G Sepharose 4 Fast Flow (GE Healthcare). The column was washed with equilibration buffer and a high salt buffer (Wash 2: 20 mM phosphate, 1M NaCl, pH 7) before elution with 0.1M glycine-HCl, pH 2.7. The eluate was neutralized with a 1M Tris, pH 9.0 buffer immediately upon completion of elution.

A second affinity purification step isolated the Enzyme 1-specific antibodies from the Protein G eluate antibody mixture. The neutralized Protein G eluate was loaded onto a column having immobilized Enzyme 1 and washed with Equilibration and Wash 2 buffers. The Enzyme 1-specific polyclonal antibodies were eluted with 20 mM citrate, 500 mM arginine-HCl, pH 2.7 and neutralized with a 1M Tris, pH 8.0 buffer.

Finally, the antibodies were exchanged into coupling buffer and concentrated to approximately 5 mg/mL using Amicon Ultra-15 10 kDa centrifugal filter units (EMD Millipore, Billerica, Mass.). The coupling buffer varied depending on the chosen coupling technique.

For Enzyme 2, several monoclonal antibody clones were generated in-house from murine hybridomas and transfected into Chinese hamster ovary cells to enable recombinant production in a bioreactor. The cell culture fluid recovered from the bioreactors was purified using Protein G Sepharose, buffer exchanged, and concentrated as described for Enzyme 1. The second affinity purification was omitted.

Coupling Procedures

ToyoPearl AF-Tresyl-650M

The free ligand, either an enzyme or antibody, was buffer exchanged into a selected coupling buffer. Dry Toyopearl Tresyl (1-3 g) resin was thoroughly wetted and washed three times with coupling buffer. For each wash, the resin slurry was well mixed by gentle rotation, centrifuged for 10 min at 2000 g, followed by decanting of the supernatant. After decanting, a solution containing free ligand (1-10 mg/mL) was added to the resin to yield a 50% slurry. Coupling proceeded at room temperature with gentle end-over-end mixing.

Small, typically 100 μL samples were obtained immediately after initiating the coupling and periodically thereafter. Samples were immediately spun down using a microcentrifuge and the absorbance at 280 nm was measured in the supernatant to calculate percent coupling according to the following equation:

$$\% \text{ Coupling} = \frac{A_{initial} - A_{sample}}{A_{initial}}(100\%) \quad (1)$$

where $A_i$ is the absorbance measured at 280 nm. To terminate the reaction, the slurry was centrifuged and the supernatant recovered before three washes with coupling buffer. The unreacted functional groups were capped by incubation with blocking buffer (1M Tris, pH 8.0) for 2 hours at room temperature under end-over-end mixing. The coupled, blocked resin was washed with Wash 2 buffer. All supernatants were collected to complete the mass balance and confirm the percent coupling calculation.

AminoLink® Plus

Coupling was performed with slight modifications to the vendor protocol. Briefly, ligand was exchanged into coupling buffer, typically 100 mM phosphate, 150 mM NaCl, pH 7.2. The ligand solution (1-5 mg/mL) was combined with AminoLink® Plus resin and sodium cyanoborohydride to achieve a 75% slurry and final NaCNBH$_3$ concentration of 50 mM in BakerBond drip columns. The reaction proceeded at room temperature and samples were obtained to monitor percent coupling as described above. The coupling was quenched for 30 min using 1M Tris-HCL, pH 7.4 buffer and NaCNBH$_3$. Finally, the resin was washed with Wash 2 buffer and absorbance measurements were performed on all fractions to complete the mass balance. All resin wash steps were performed by gravity flow (and not centrifugation).

CarboLink™ and SulfoLink®

Coupling was performed strictly according to the vendor protocol.

Binding Capacity Testing

Static binding capacity was measured in batch mode on the bench-top using BakerBond disposable drip columns. All flow was achieved by gravity. The test resin was equilibrated with 5 resin volumes of equilibration buffer. Immediately after the buffer exited the column, purified Enzyme 1 or 2 (3-6 mg/mL, in Equilibration buffer) was added to achieve a 50% slurry. Approximately 150% of the total resin capacity (by mass) was added to ensure saturation. Binding proceeded for 30 min with end-over-end mixing at 8° C. (due to the lability of Enzymes 1 and 2). After incubation, the resin was washed with six resin volumes of Wash 2 buffer followed by six volumes of elution buffer (20 mM citrate, 500 mM arginine-HCl, pH 2.7). The column was re-equilibrated with five volumes of equilibration buffer and stored in 0.05% sodium azide. Absorbance at 280 nm was measured for all fractions, including the post-incubation flow-through.

The static binding ratio, $\varphi_S$, was calculated according to:

$$\varphi_S = \frac{m_{Ag}^{bound}}{m_{Ab}^{coupled}} = \frac{m_{Ag}^{load} - m_{Ag}^{flowthrough}}{m_{Ab}^{coupled}}$$

Dynamic binding capacity was also tested for packed columns by performing frontal loading experiments at multiple residence times. Purified Enzyme 1 or 2 was diluted in Equilibration buffer to a concentration comparable to that in cell culture harvest fluid for each respective enzyme. Flow-through fractions were collected, concentrated, and assayed for enzymatic activity (see assay section below) as confirmation. A safety factor of 15% was applied to determine loading for column purifications in order to minimize the risk of product breakthrough.

Cell Culture

Biotherapeutic proteins were produced recombinantly in Chinese Hamster Ovary (CHO) cells using perfusion bioreactors.

Single-Step Affinity Column Method

The final column method for Enzymes 1 and 2 is presented in Table 2.

TABLE 2

Affinity column method for Enzyme 1 and 2 production runs.

| Column Step | Column Volumes | Linear Velocity (cm/hr) | Enzyme 1 Buffer | Enzyme 2 Buffer |
| --- | --- | --- | --- | --- |
| Equilibration | 3 | 125 | 20 mM phosphate, pH 7.0 | |
| Pre-Clean** | 3 | 100 | 20 mM citrate, 500 mM arginine-HCl, pH 2.7 | 20 mM citrate, pH 2.7 |
| Equilibration | 3 | 125 | 20 mM phosphate, pH 7.0 | |
| Load | * | 5.5 min residence time** | N/A | |
| Wash 1 | 8 | Same as Load | 20 mM phosphate, pH 7.0 | |
| Wash 2 | 3 | 125 | 20 mM phosphate, 1M NaCl, pH 7.0 | |
| Re-Equilibration | 2 | 125 | 100 mM phosphate, pH 7.0 | |
| Elution** | 3.5 | 100 | 20 mM citrate, 500 mM arginine-HCl, pH 2.7 | 10 mM citrate, pH 3.0 |
| Re-equilibration | 2 | 125 | 100 mM phosphate, pH 7.0 | |
| Storage | 2.5 | 125 | 20 mM phosphate, 0.05% sodium azide pH 7.0 | |

* Step volume dependent on concentration of Enzyme in the load.
**Pre-clean buffer, elution buffer, and loading residence time were determined individually for Enzymes 1 and 2.

The theoretical maximum binding ratio, $\varphi_{max}$, was calculated according to:

$$\varphi_{max} = \frac{M_{Ag}}{M_{Ab}} N$$

Where $M_i$ is the molecular weight of species i and N is the number of antigen molecules that can be bound per antibody (N=2). In order to compare binding efficiency across multiple antigen-antibody pairs, the theoretical antigen binding efficiency, $\eta_{Ag}$, was calculated according to:

$$\eta_{Ag} = \frac{\varphi_S}{\varphi_{max}} (100\%)$$

Unless otherwise specified, all elutions dripped directly into bottles pre-titrated with neutralization buffer. The final neutralization buffers were 1M Tris, pH 8.0 and 150 mM phosphate, pH 6.75 for Enzymes 1 and 2, respectively. Elution bottles were continuously mixed using a rocker shaker to ensure rapid, gentle neutralization of the eluting product. During column method development certain parameters, such as residence time, elution buffer, and neutralization buffer, were varied to determine their effect on process performance (recovery, carryover) and product quality. Pre-cleaning buffers were chosen to ensure <1% run-to-run carryover according to area under the curve (AUC) absorbance measurements on the AKTA.

Purification Scheme for the Traditional, Multi-Step Purifications

Direct comparison study samples were also purified using a traditional, multi-step purification train. These trains included a mixture of ion exchange, hydrophobic interaction, and pseudo-affinity chromatography steps, as well as normal and tangential flow filtration operations commonly encountered in non-Mab purification schemes.

Assays

ELISA

A 96-well plate was coated with Enzyme 1 followed by incubation with samples containing anti-Enzyme 1 polyclonal antibodies in serial dilution. After washing, anti-goat detection antibodies linked to horseradish peroxidase were added to each well followed by incubation with the substrate, tetramethylbenzidine (TMB). Reaction was terminated by addition of 1N HCl and analysis was performed using a VersaMax™ ELISA microplate reader (Molecular Devices. Sunnyvale, Calif.).

Enzyme Product Quality Analysis

Enzymatic activity, concentration by reverse phase (rp)-HPLC, and aggregation by SEC-HPLC were performed as previously described Warikoo et al., (2012) *Biotech & Bioeng.*, 109:3018-3029, and Godawat, et al., (2012) *Biotechnol.*, 7:1496-1508.

Briefly, the enzymatic activity was determined by measuring the hydrolysis rate of the appropriate synthetic substrate linked to a nitrophenol-containing group. Protein concentration was determined either by measuring absorbance at 280 nm using a Nanodrop™ 1000 (Thermo Fisher Scientific) or by rp-HPLC using a POROS R2/H 2.1×30 mM column (Applied Biosystems. Carlsbad, Calif.). Specific activity was expressed as pNP (units)/mg protein. The aggregation (SEC-HPLC) assay used a TSK-GEL, G3000SWXL, 7.8 mM×30 cm, 5 µm column (Tosoh Bioscience, King of Prussia, Pa.). Enzyme 1 purity was measured by rp-HPLC using a YMC Octyl 2 mm×100 mM, 5 µm column (Waters, Milford, Mass.) while Enzyme 2 purity was assessed qualitatively silver-stained by SDS-PAGE.

Glycosylation Analysis

Glycosylation profiles were measured using procedures adapted from those previously described in Du, et al., (2005) *Am J Hum Genet.*, 77(6):1061-1074. N-linked oligosaccharides were released from the Enzyme by PNGaseF and dialyzed against sodium phosphate buffer. The dialysate was vacuum dried, reconstituted, and labeled with anthranilic acid (AA labeling). The labeled oligosaccharides were separated on an (TSKgel Amide-80, Tosoh Biosciences) HPLC column on an Agilent 1100 series HPLC (Santa Clara, Calif.). The HPLC software was used to quantitate the peak area of selected glycan peaks relative to the total peak area.

Example 1. Purification of Anti-Enzyme 1 Antibody

Anti-Enzyme 1 polyclonal antibody was purified from antiserum using two chromatography steps: Protein G capture followed by a second affinity step using a column with Enzyme 1 immobilized on Tosoh Tresyl resin. Multiple elution conditions, including variations in pH and mobile phase modifiers, were screened before finalizing the column method (Table 3). All buffers were adjusted to the final pH using either 2N HCl or 50% NaOH. Minimal recovery (<50%) was observed for all elution conditions tested except for pH 2.7, 500 mM arginine-HCl (80%). The strong elution condition required to recover a significant portion of the polyclonal antibodies from the Enzyme 1 column was unexpected and indicated very strong avidity. Complete recovery (>98%) of antibody was observed using the regeneration buffer as the elution condition.

ELISA measurements were performed on selected Enzyme 1 column eluates to determine whether the elution conditions affected the ability of the antibody to bind antigen (Table 3). The 500 mM arginine-HCl eluate was assumed to be 100% pure Enzyme 1-specific antibody and was used as the reference standard for the ELISA. All measurements were normalized according to initial sample mass concentration.

Overall, there were minimal differences observed among the samples tested. The slight decrease in signal for the thiocyanate buffer was outside typical assay variability, indicating some loss of function under this elution condition. Finally, the low relative signal for antibodies recovered in the regeneration buffer indicated functional disruptions caused by the strongly denaturing regeneration buffer (3M guanidine-HCl). The low relative signal could not be due to non-specific impurities, since only very high avidity Enzyme 1-specific antibodies remain on the column after elution.

TABLE 3

Summary of elution screening results in which Enzyme 1-specific antibody recovery was determined for various elution buffers.

| Buffer | pH | Mobile Phase Modifier | Recovery by A280 (%) | ELISA* (% signal relative to control) |
|---|---|---|---|---|
| 20 mM citrate | 2.7 | None | 0 | n.t. |
| | | 1M NaCl | 3 | n.t. |
| | | 200 mM arginine-HCl | 48 | 100 |
| | | 500 mM arginine-HCl | 80 | 100 |
| 20 mM citrate | 4.0 | 500 mM arginine-HCl | 32 | 90 |
| 20 mM phosphate | 7.0 | 1M ammonium thiocyanate | 50 | 80 |
| 10 mM bicine | 8.5 | 50% ethylene glycol | 3 | n.t. |
| 100 mM glycine | 10.5 | None | 0 | n.t. |
| N/A | | 3M guanidine-HCL | >98 | 15 |

*Antibody functionality (binding) was determined by ELISA (n.t. indicates not tested).

Selection of the final elution condition depended on a number of competing factors. Increasing the denaturant concentration while decreasing pH improved recovery, thereby maximizing use of the antibody supply. However, the overall avidity of the antibodies recovered is directly related to the selected elution buffer. While antibodies recovered under increasingly denaturing conditions may still bind antigen. Considering the relative lability of enzymes when compared to antibodies, further decreases in pH or addition of additional denaturants was not studied. The 20 mM citrate, 500 mM arginine-HCl, pH 2.7 was selected as the elution buffer for the Enzyme 1 column method.

Production purifications were performed using the finalized Enzyme 1 column method and target enrichment was confirmed by ELISA measurements of samples from the Protein G and Enzyme 1 column operations. As before, the Enzyme 1 column eluate was used to generate the standard curve and absorbance measurements at 280 nm were used to adjust for differences in mass content across samples. The resulting % of signal relative to control data provided an approximate indicator of Enzyme 1-specific antibodies in a sample as a percentage of the total mass. The step-wise increases in this value indicated enrichment of Enzyme 1-specific antibodies over the two-step process. A very low signal relative to control was measured for the Enzyme 1 column flow-through, indicating nearly complete binding of Enzyme 1-specific antibodies. Purification was also successfully performed by omitting the Protein G step; however, this strategy was not pursued in order to minimize exposure of the Enzyme 1 column to serum components. Performing the Protein G step, although slightly more time-consuming, increased the lifetime of the relatively costly Enzyme 1 column.

TABLE 4

ELISA analysis of samples from the two-step isolation of anti-Enzyme 1 polyclonal antibodies from goat serum.

| Column Operation | Sample Type | ELISA (% Signal Relative to Control) |
|---|---|---|
| Protein G | Load | 1.1 |
| | Eluate | 8.0 |
| Enzyme 1 | Flow-through | 1.1 |
| | Elution | 100 |
| | Regeneration | 15 |

The antibody purification data also provided opportunity to assess the polyclonal production in goats. Specifically, the Protein G eluate, which should have captured nearly all of the antibodies present in the serum, indicated that 8.0% of the antibodies in serum were specific to Enzyme 1. Additionally, the ELISA concentration of the Protein G load, which was serum diluted 1:1, indicated an Enzyme 1-specific antibody concentration in serum of 0.80 mg/mL. Overall, these results were consistent with expectations for polyclonal production in goats for which antigen-specific polyclonal levels are typically between 0.1-2.0 mg/mL serum comprising 1-10% of the total antibodies present in the serum.

Example 2. Antibody Coupling and Binding Capacity Optimization

1. Enzyme 1

A screening study was performed to maximize the coupling reaction yield as well as the binding capacity of the anti-Enzyme 1 polyclonal antibody affinity resin. Several variables known to affect coupling yield and binding capacity were studied, including coupling chemistry, coupling buffer (pH and ionic strength), temperature, and ligand density. Coupling yield and static binding capacity were measured and calculated as described in the binding capacity testing section above. As indicated, multiple buffer conditions were studied for the Tosoh Tresyl couplings, while the manufacturer recommended buffers were used exclusively for AminoLink® (pH 7.2), CarboLink™, and SulfoLink® resins. The measured coupling yields were high, generally 70% or greater, while the binding efficiencies were between 2 and 14%. A wide range of binding efficiencies have been reported in the literature for similar affinity constructs, ranging from as little as 0.1% to nearly 100% efficiency. Because it is extremely difficult to predict, a priori, expected binding efficiency as a function of fundamental parameters such as dissociation constant, $K_D$, or selected coupling conditions, screening and optimization experiments as summarized in Table 5 are often required to define reasonable binding capacity expectations.

TABLE 5

Summary of coupling yield and binding efficiency.

| Coupling Resin | | Temp (° C.) | Final Ligand Density (mg Pab/mL resin) | Time (hr) | Yield (%) | $\eta_{Ag}$ Binding Efficiency (%) (Mean ± S.D.) | # of Repeats |
|---|---|---|---|---|---|---|---|
| AminoLink® | | 21 | 5.0 ± 0.1 | 15 ± 1 | >99 | 4 ± 1 | 5 |
| | | 1 | 3.8 ± 0.3 | 2.5 ± 0.5 | 75 ± 5 | 14 ± 2 | 3 |
| | | | 3.8 | 5.5 | 75 | 13 | 1 |
| | | | 2.5* | 6 | 50 | 5 | 1 |
| Tresyl | 100 mM phosphate, 0.5M NaCl, pH 7 | 21 | 0.4 | 16 | 78 | 4 | 1 |
| | | | 7.0 | 16 | 67 | 4 | 1 |
| | 100 mM phosphate, 0.5M NaCl, pH 7.5 | 1 | 5.0 ± 0.2 | 16 ± 1 | 95 ± 5 | 3 ± 1 | 3 |
| | 1M phosphate, pH 8.0 | 1 | 5.0 | 18 | 70 | 2 | 1 |
| CarboLink™ | | 21 | 2.6 | 19 | 70 | 4 | 2 |
| SulfoLink® | | 21 | 0.6 | 0.75 | 15 | n.t. | 2 |

*Resin slurry and ligand solution concentrations were decreased fourfold by dilution with coupling buffer (cyanoborohydride concentration was maintained at 50 mM).

Overall, the coupling time and, correspondingly, the coupling yield were found to have the greatest impact on binding efficiency. This improved binding efficiency at decreased coupling yields was observed for multiple replicates, at both room temperature and 8° C. Interestingly, dilution of the coupling slurry not only decreased the coupling rate as expected, but also led to a dramatic decrease in binding efficiency.

There are a number of potential mechanisms by which binding efficiencies of less than 100% can be realized, including steric hindrance caused by (1) ligand over-crowding, (2) mis-orientation of the ligand binding domains (i.e., the antibody is pointed inward), and (3) disruption of the ligand binding domain caused by multipoint attachments between ligand and activated functional groups on the resin.

Data generated during the screening study provided information by which the effect of these potential mechanisms on binding efficiency could be assessed. The variations in ligand density addressed potential over-crowding. Specifically, ligand density was varied from 2.5-5.0 mg/mL on AminoLink® resin and 0.4-7.0 mg/mL on Tosoh Tresyl resin. In these experiments, no statistically significant correlation between ligand density and binding efficiency was observed.

Ligand mis-orientation is a problem inherent to amine-based coupling chemistries, in which linkages between ligand and resin occur randomly according to the availability of free amines on the antibody surface. Results for two alternative coupling chemistries, CarboLink and Sulfo-Link®, in which coupling is designed to orient the antibody in the outward direction, were unable to significantly improve binding efficiency. Similarly low binding efficiency (4%) was observed for the CarboLink™ coupling, while insufficient coupling yield (15%) was obtained for the SulfoLink® chemistry. Optimization of the CarboLink™ coupling conditions, particularly the carbohydrate oxidation step, could potentially improve binding efficiency.

Figure 4:
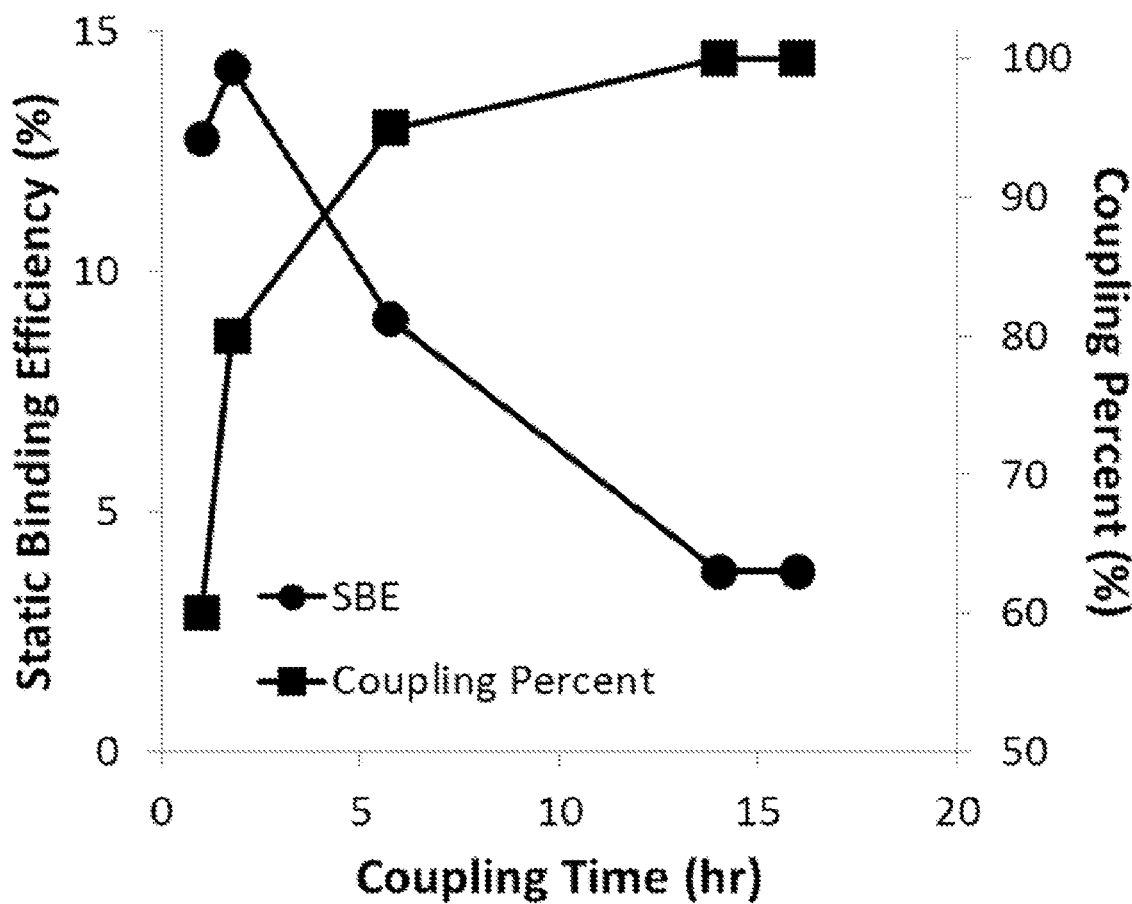
FIG. 4 shows static binding efficiency (SBE) and coupling percent as a function of coupling time for Enzyme 1 coupled to AminoLink® Plus with 5 mg Ab/mL of resin present in the initial coupling slurry.

The binding efficiencies achieved for AminoLink® Plus were sufficient such that further work on alternative chemistries was not pursued. To further study the effect of coupling time (and yield) on binding efficiency, parallel coupling reactions were performed and terminated at various time points. The static binding capacity was measured for each affinity resin and the corresponding binding efficiency was calculated (FIG. 4).

As shown, the coupling percent was a strong function of coupling time, increasing very rapidly in the first two hours before beginning to level off between the 2 and 6 hr timepoints. Coupling proceeded to completion before 14 hours. The static binding efficiency was also strongly dependent on coupling time and percent, reaching a maximum at 2 hours of coupling and decreasing dramatically for longer coupling periods. This result was consistent with the third proposed mechanism for decreased binding efficiency, in which extended coupling times increase the likelihood of potentially detrimental multi-point attachments. Based on this finding, coupling yield was monitored during all subsequent experiments and coupling was terminated when measurements indicated a significant decline in the coupling rate.

To finalize the selection of the coupling chemistry, the stability of the polyclonal antibodies in the recommended coupling buffers was determined for the two amine chemistries studied. Antibodies were buffer exchanged into each respective coupling buffer, incubated at room temperature overnight, and assayed for binding avidity by ELISA (Table 5). No change was observed for antibodies incubated in the AminoLink Plus pH 7.2 conditions (including the cyanoborohydride reductant), while significant precipitation occurred while exchanging the antibodies into the coupling buffer for the elevated pH AminoLink® Plus procedure. Loss of signal was observed for antibodies exposed to the two Tosoh Tresyl coupling buffers studied.

These results clearly indicated that the anti-Enzyme 1 polyclonal antibody stability was significantly affected by elevated pH and conductivity and that the gentlest coupling conditions, those associated with the AminoLink® Plus pH 7.2 protocol, would be the most conducive to maximizing binding efficiency.

TABLE 6

ELISA measurements of anti-Enzyme 1 polyclonal antibodies exposed to coupling buffers, temperatures, and any additives required by the coupling procedure.

| Coupling Chemistry | Coupling Buffer | pH | Coupling Chemistry Additive | ELISA (% Signal Relative to Control) |
|---|---|---|---|---|
| AminoLink ® Plus | 100 mM phosphate, 150 mM NaCl | 7.2 | Sodium cyanoborohydride | 120 |
| | 100 mM citrate, 50 mM carbonate | 10.0 | N/A | n.t.* |
| Tosoh Tresyl | 100 mM phosphate, 500 mM NaCl | 7.5 | None | 65 |
| | 1M potassium phosphate | 8.0 | None | 15 |

*Not tested (n.t.) due to significant precipitation observed during buffer exchange.

2. Enzyme 2

The procedures developed during the Enzyme 1 studies were re-applied to a second antibody-antigen pair. Four monoclonal antibody clones against a second therapeutic biomolecule, Enzyme 2, were available internally. The various clones were coupled to AminoLink®: resin and the resultant affinity resins were assayed for static binding efficiency (Table 7). Overall, the static binding efficiencies were considerably higher for Enzyme 2 than for Enzyme 1. The relative size of Enzyme 2, which has a molecular weight >30% lower than Enzyme 1, was one potential source for the observed difference, although other factors may also have contributed. Clones A and B had the highest static efficiency when coupled to resin and Clone A was pursued for further study due to its availability in inventory. Finally, the highest binding efficiency was measured for the Clone A affinity resin coupled for 3 hr instead of 5 hr, which was consistent with the results for Enzyme 1 (FIG. 4). This result was an additional indication that reducing the opportunity for multi-point attachments of the ligand to the functionalized resin is important for maximizing binding efficiency.

TABLE 7

Enzyme 2 coupling experiments for four anti-Enzyme 2 monoclonal antibody clones using AminoLink ® Plus resin with 4 mg Ab/mL resin present in the initial coupling slurry.

| Clone | Coupling Time (hr) | Coupling Percent (%) | Static Binding Efficiency (%) |
|---|---|---|---|
| A | 5 | 62 | 31 |
| A | 3 | 65 | 48 |
| B | 5 | 54 | 30 |
| C | 5 | 63 | 21 |
| D | 5 | 50 | 2 |

The coupling method optimization significantly improved the binding efficiency. These improvements provided a number of surprising benefits, including efficient use of the antibody supply as well as minimization of the column size (and correspondingly, the elution volume) required to yield purified enzyme. Avoiding these inefficiencies enabled the production of analytical scale affinity columns for use in single-step purifications (Table 8). In all cases, the amount of mass generated in a single column operation was sufficient to supply a wide range of product quality testing, including assays measuring activity, concentration, purity, aggregation, glycosylation profile, and binding. Two anti-Enzyme 1 columns (in which resin was packed into columns having a diameter of 0.66 cm) were produced from two different serum bleeds, one from each goat, to enable study of potential column-to-column variability as a function of production bleed (total dynamic binding capacity was calculated assuming a 15% safety factor to minimize Enzyme flow-through).

TABLE 8

Properties of the anti-Enzyme 1 and 2 affinity columns.

| Property | Enzyme 1 Column 1 | Enzyme 1 Column 2 | Enzyme 2 Column | Units |
|---|---|---|---|---|
| Column Volume | 5 | 6.6 | 3.4 | mL |
| Ligand Density | 3.8 | 3.2 | 2.8 | mg Ab/mL |
| Static Binding Efficiency | 14 | 15 | 48 | % |
| Dynamic Binding Capacity | 0.5 | 0.3 | 0.8 | mg Enzyme/mL |
| Total Dynamic Binding Capacity | 1.8 | 1.7 | 2.4 | mg Enzyme |

3. Development of Anti-Enzyme Column Methods

Having produced the analytical scale columns for Enzymes 1 and 2, the next step was the development of the anti-enzyme column methods. Whereas immobilized Enzyme 1 could be repeatedly exposed to the harsh elution condition (pH 2.7, 500 mM arginine-HCl) required to dissociate the anti-Enzyme 1 polyclonal antibodies during purification, the stability of enzymes to similarly harsh conditions while in the mobile phase was significant unknown during the method development. The selection of elution conditions, therefore, was subject to two competing constraints: maximization of recovery while minimizing deleterious effects to the eluting enzyme. Maximizing recovery minimized the chances that significant sub-populations of Enzyme 1 and 2 could be segregated by the affinity purification. Aggregation as measured by SEC and specific activity were the primary tool used to measure these potential adverse effects.

For Enzyme 1, the conditions for the Enzyme 1 column method were used as the starting point for the development of the anti-Enzyme 1 column method. Recoveries by A280 and activity were found to be approximately 60 and 80% for the two elution buffers studied, pH 2.7 and pH 2.7 with 500 mM arginine-HCl, respectively. Both elution buffers contained 20 mM citrate (sufficient neutralization buffer (M Tris, pH 8.0) was added to achieve a final pH of 7.0). A number of neutralization techniques were studied to minimize the exposure of Enzyme 1 to the denaturing conditions (Table 9). Significant loss in specific activity and increase in aggregate levels were observed when Enzyme 1 was allowed to remain in the elution buffer for an extended period. Neutralization during or immediately after elution minimized activity losses and aggregate formation. Placement of a pre-titrated elution bottle on a rocker shaker provided an automated titration. Separate experiments demonstrated titrated eluates could remain shaken for at least three days without any effect. Interestingly, mixing of the eluate and neutralization buffer with a stir bar on a stir plate led to significant turbidity, a likely indication of elevated shear sensitivity of Enzyme 1 in the presence of 500 mM arginine.

TABLE 9

Various strategies studied to neutralize Enzyme 1 eluting from the anti-Enzyme 1 affinity column.

| Mixing Initiation Time | Mixing Method | Specific Activity (% of control) | SEC-Aggregation (%) |
|---|---|---|---|
| During elution | Shaken by hand | 99 | 0.3 |
| 5 min post-elution | | 92 | 0.4 |
| 60 min post-elution | | 83 | 5.0 |
| 240 min post-elution | | 56 | 40 |
| During elution | Rocker shaker | 99 | 0.4 |
| During elution | Stirring bar | n.t.* | |

*n.t. indicates not tested. Sample was extremely turbid.

For Enzyme 2, no previous column method development data were available as a starting point because the anti-Enzyme 2 monoclonal antibodies were purified in a single-step by Protein G. As a result, a wide range of elution buffers were screened to determine the final anti-Enzyme 2 column method (Table 10). As for Enzyme 1, the goal of studying these conditions was to maximize recovery while minimizing any effects to specific activity and aggregation. For all Enzyme 2 column operations, the eluates were titrated using neutralization buffer specifically designed for Enzyme 2. Overall, the recoveries achieved for the anti-Enzyme 2 affinity column were lower than for Enzyme 1, typically around 70%. Addition of 150 mM NaCl increased recovery, but also led to significant aggregation and loss of specific activity. For this reason, higher salt concentrations were not pursued. A number of mobile phase modifiers were also studied, including arginine, glycine, and methionine, for their potential to stabilize the Enzyme 2 structure at low pH. Addition of these modifiers actually led to decreased specific activity and increased aggregation, while having minimal effect on recovery. It is important to note that, significant amounts of HCl were required in order to achieve the desired pH in the presence of these modifiers and that the added chloride ions would likely affect Enzyme 2 aggregation in a similar manner as did the sodium chloride. Therefore, it is difficult to uncouple the contributions of the mobile phase modifier and the increased conductivity to the observed results.

TABLE 10

Elution conditions studied for the anti-Enzyme 2 affinity column method development.

| Citrate Concentration (mM) | pH | Mobile Phase Modifier | A280 Recovery (%) | Specific Activity** (% of control) | SEC-Aggregation** (%) |
|---|---|---|---|---|---|
| 20 | 2.7 | None | 72 | 89 | 1.2 |
| | 3.0 | None | 75 | 92 | 1.8 |
| | 2.7 | 150 mM NaCl | 80 | 53 | 46 |
| | 3.0 | 50 mM arginine-HCl | 70 | 81 | 9.7 |
| | 3.0 | 100 mM glycine-HCl | 73 | 89 | 3.7 |
| 10 | 3.0 | None | 71 | 89 | 0.9 |
| 5 | 3.0 | None | 63 | 83 | 0.5 |
| 5 | 3.3 | None | 54 | 92 | 0.3 |

* n.t. indicates not tested. Significant foaming observed for this eluate.
**The specific activity of the load was 100% of control, while the aggregation level of the load was 0.3%.

A strong trend in both recovery and structural integrity was observed in experiments varying citrate concentration. Although aggregation decreased as citrate concentration decreased, so too did recovery. Increasing the elution buffer pH to 3.3 further decreased the aggregation, however the recovery was reduced even further to 54%. Based on the results of the elution screening study and the clear trade-off between maximizing recovery and minimizing aggregation, the 10 mM citrate, pH 3.0 elution buffer was selected for the column method.

Example 3. Affinity Column Performance in Direct Comparison with Multi-Step Process Train Purification for Enzyme 1

To test the applicability of the antibody affinity columns, identical starting materials were purified using both the anti-Enzyme affinity column and the multi-step scale-down purification train to enable direct comparisons of the resulting purified materials. Two classes of load materials were studied: (1) drug substance, and (2) clarified harvest fluid for both Enzymes 1 and 2. Drug substance was used as a load to determine whether any product quality attribute, such as glycosylation profile, was changed by the affinity column operation.

1. Enzyme 1 Direct Comparison Study

For Enzyme 1, ten lots of harvest material were available for study. These lots were obtained from a large design of experiments (DoE) clone and media selection study. The individual lots were selected to cover a wide range of values for critical quality attributes, such as key glycans or product-related impurities. For the affinity purifications, the ten lots were divided into two groups of five. Harvest lots 1-5 were purified using anti-Enzyme column 1, while lots 6-10 were purified on column 2.

2. Purity and Specific Activity

Figure 5:
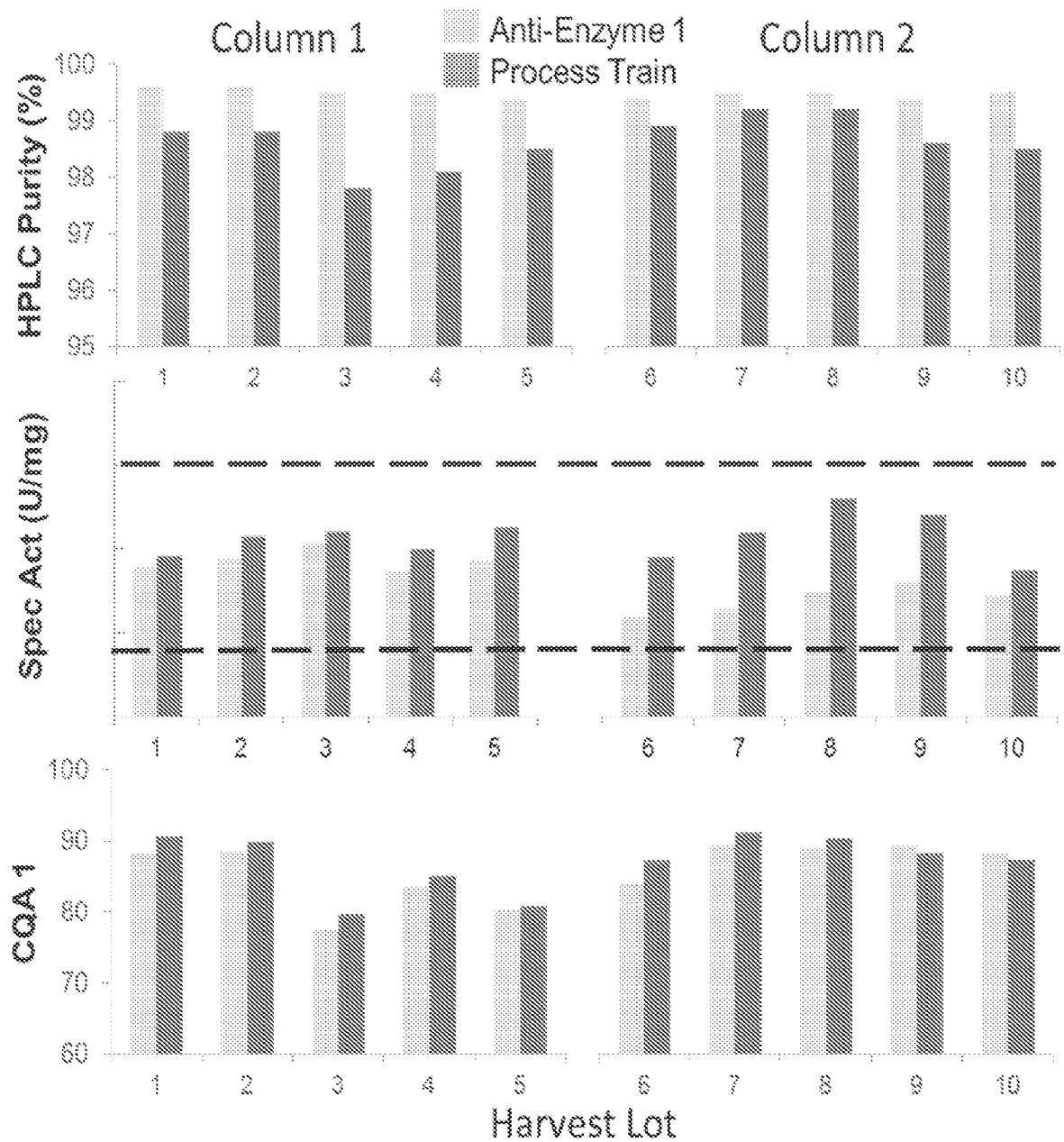
FIG. 5 shows results of a direct comparison study for Enzyme 1 purified from ten separate lots of clarified harvest using either the anti-Enzyme 1 affinity column (light grey) or two-step traditional process train (dark grey). Dashed lines indicate release specification range, where applicable.

Over the ten purifications of Enzyme 1, the average recovery over the affinity column was 78.0%±1.7% (mean±S.E.), while the average recovery for the ultrafiltration/diafiltration (UF/DF) step was 88.5%+2.0%. These two step recoveries combined for an average overall recovery of 69%. The results for the direct comparison study of Enzyme 1 purified from ten separate lots of clarified harvest using either the anti-Enzyme 1 affinity column (light bar) or two step traditional process train (dark bar) is shown in FIG. 5. For the multi-step, traditional purification, only two column steps were required to achieve purities sufficient for most product quality analyses. This two-step train included one hydrophobic interaction chromatography (HIC) step and one ion exchange (IEX) step. The overall process recovery for the process train, including the UF/DF, was approximately 70%.

The purity as measured by reverse phase-HPLC was ≥99.5% for all anti-Enzyme 1 affinity column eluates (FIG. 5). This purity was achieved in a single-step from clarified harvest load material and was sufficient for all product-specific assays. The affinity eluate purity was higher than that achieved by the two-step process train. The specific activity results were similar for the anti-Enzyme 1 column and process train, although the eluates from the second column preparation had slightly lower specific activities. Nonetheless, all recovered material was within the release specification for specific activity, which was itself, an interesting and surprising finding considering the exceedingly strong conditions (pH 2.7, 500 mM arginine-HCl) required to dissociate Enzyme 1 from the immobilized polyclonal antibodies.

3. Critical Quality Attributes (COAs)

The results for CQA 1, an indicator of a product-specific impurities, were comparable to one another whether the harvest load was purified by the affinity column or the process train (FIG. 5). The SEC-aggregation results for the anti-Enzyme 1 affinity eluates ranged between 0.3 and 0.8%, while the process train drug substance aggregation levels included several LOQ (limit of quantification=0.2%) results and a maximum aggregation level of 0.6%. No statistical correlation was found between the two data sets. The aggregation results indicated slightly higher aggregate levels for the affinity column eluates.

4. Glycosylation Profiles

As the ten harvest lots were selected to cover a wide range of glycosylation profiles expected for Enzyme 1, glycoprofiles were measured and directly compared for Enzyme 1 purified by either the affinity or process train techniques. The glycosylation profile assay quantitates the relative abundance of twelve selected glycostructures.

Figure 6:
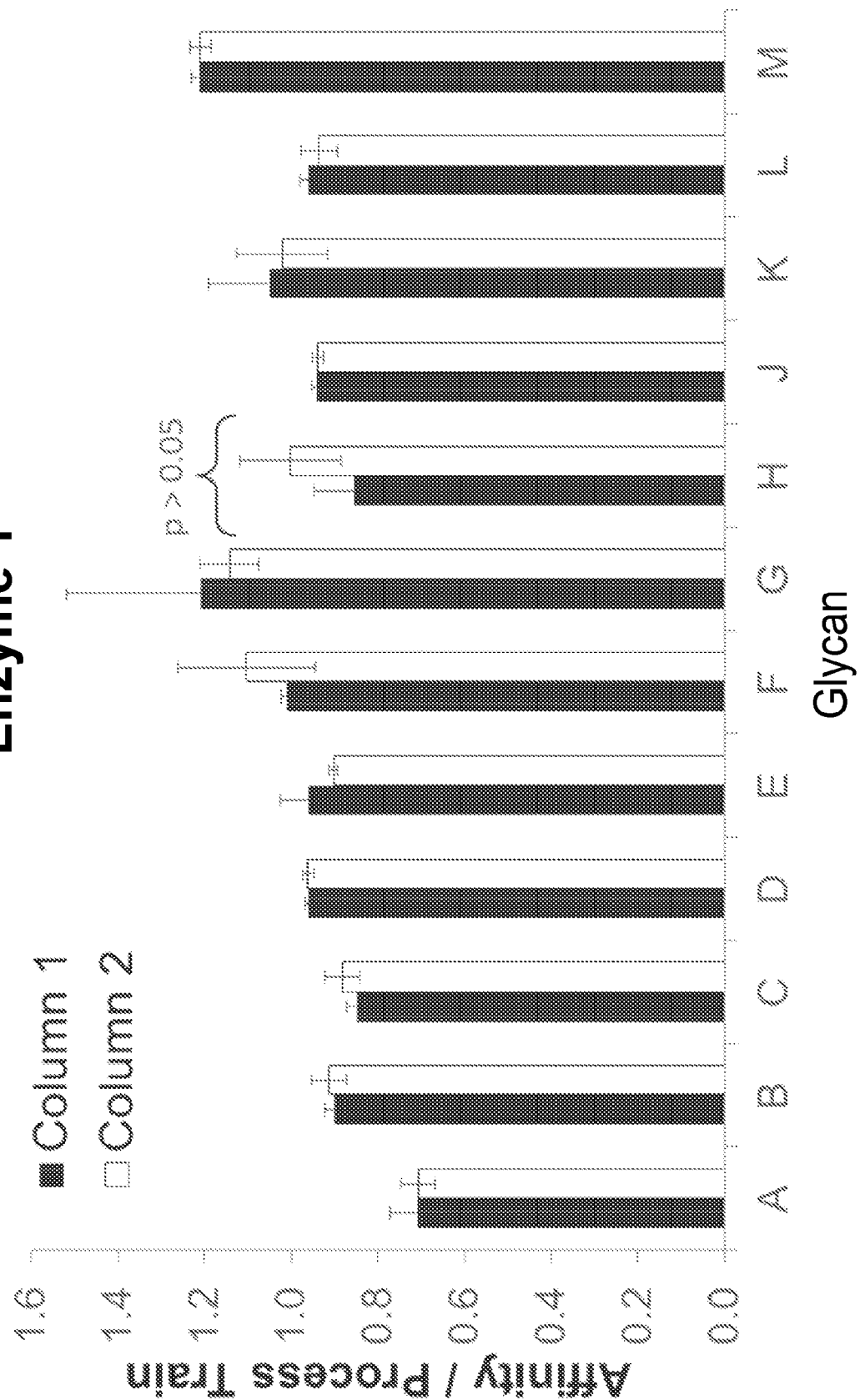
FIG. 6 shows glycosylation profiling data for the Enzyme 1 direct comparison study. Anti-enzyme 1 column eluate data (affinity) were divided by process train data for each glycan. Results were separated for the two anti-Enzyme 1 columns used in the study to demonstrate column-to-column consistency. Data are presented as mean±standard deviation. Results for two affinity column lots are statistically indistinguishable, except for glycan H (p=0.11).

Direct comparisons of individual glycostructures revealed some that were comparable for the two purification techniques, while others that were significantly different in terms of relative abundances. To quantify these differences, a ratio was calculated by dividing the result for the anti-Enzyme 1 affinity eluate by that for the process train for each of the 12 individual glycostructures, and the results are shown in FIG. 6. A ratio equal to one would indicate comparability, while a ratio greater than one would indicate greater relative abundance of a glycoform and glycan present in the affinity eluate than in the process train drug substance. The average ratio and standard deviation for each glycostructure were grouped according to the anti-Enzyme 1 affinity column lot used in the respective purification.

The calculated ratios revealed that some glycans were present in significantly lesser abundance in the affinity eluate (A and C), greater abundance (M) or comparable abundance (D, E, K, for example) relative to the process train drug substance (FIG. 6). There was also excellent consistency for each glycostructure ratio between the two anti-Enzyme 1 affinity column lots used in the study. All ratios, except those for glycan H, were statistically indistinguishable from one another according to Student's t-tests. The observed column-to-column difference for glycan H is likely due to experimental noise. When combining the data sets for the two columns, the overall variability observed for each glycostructure ratio was quite low—the standard deviation was ≤0.11 for all glycans except G and ≤0.05 for seven of the quantitated glycans (FIG. 6). This consistency indicated that the ratios could be used to develop a reliable, predictive model. This model could be used to predict glycosylation results for multi-step process train drug substance using only the single-step anti-Enzyme 1 affinity technique.

Example 4. Affinity Column Performance in Direct Comparison with Multi-Step Process Train Purification for Enzyme 2

1. Enzyme 2 Direct Comparison Study

A similar product quality comparison was also executed for Enzyme 2 using the Mab affinity column. As before, two categories of materials were studied on the affinity column: (1) Enzyme 2 drug substance, and (2) Enzyme 2 clarified harvest fluid. The drug substance samples were processed on the anti-Enzyme 2 affinity column and the pre- and post-column product quality measurements were compared to one another to determine any effect of the affinity step.

For the harvest fluid samples, individual slices from a single bioreactor campaign were purified either in a single-step using the affinity column or in a four step, traditional purification process train, which included HIC, ion exchange, and pseudo-affinity steps. The resultant affinity column eluates and process train drug substances were compared directly to one another. Two drug substance lots and three harvest slices were studied in this Enzyme 2 direct comparison study.

samples (1% versus 0.2%, respectively). This increase occurred for both drug substance and harvest slice loads, again indicating that the increase was due to the affinity column process. This small increase was not anticipated to have an impact on any other product quality analyses.

Interestingly, the percent-dimer measured in the affinity eluates and process train drug substances were similar for the two purification strategies, suggesting that the affinity column operation did not affect the proportion of dimers.

TABLE 11

Specific activity and SEC % aggregate and dimer results for Enzyme 2 direct product quality comparison.

| Load Type | | Activity Recovery (%) | | Specific Activity (% of control) | | SEC-Aggregate (%) | | SEC-Dimer (%) | |
|---|---|---|---|---|---|---|---|---|---|
| | | Affinity | Process Train | Affinity | Process Train | Affinity | Process Train | Affinity | Process Train |
| Drug Substance* | D1 | 58 | N/A | 81 | 100 | 0.9 | 0.1 | 4.4 | 6.0 |
| | D2 | 66 | N/A | 96 | 100 | 0.5 | 0.3 | 4.8 | 5.0 |
| | D3 | N/A | N/A | | | | | | |
| Harvest Slice | H1 | 61 | 33 | 87 | 100 | n.t. | 0.2 | n.t. | 3.1 |
| | H2 | 54 | 50 | 87 | 100 | 1.2 | 0.2 | 3.3 | 3.2 |
| | H3 | 46 | 49 | | | 1.1 | | 3.8 | |

*For drug substance load type, process train data were measured before affinity column processing.
n.t. indicates not tested.

2. Purity and Specific Activity

As described above for Enzyme 1, activity and concentration measurements were performed to determine specific activity (Table 11).

Overall, the specific activity results were consistently lower for the affinity column eluate irrespective of the load type. This suggested that the affinity column process led to a decrease in the specific activity of the recovered Enzyme 2, a result similar to that observed for Enzyme 1. While it would be preferable to avoid such a decrease, if the magnitude of the decrease remains consistent over an increasingly large number of replicates, then the difference can be modeled accordingly.

In terms of process performance, the step recovery on the affinity column operation ranged from 46-66% according to activity testing (Table 11). Activity testing was preferred to A280 or HPLC quantification methods due to its ability to most accurately measure Enzyme 2 concentration in harvest. These recoveries were slightly lower than expected based on elution screening data (Table 10); however, the majority of the discrepancy between the results and expectations was due to losses in specific activity. For example, for the drug substance loads, the mass recoveries were 72 and 69% when accounting for the 19 and 4% loss in specific activity for drug substance loads 1 and 2, respectively.

Purity testing was performed by silver-stained SDS-PAGE. Anti-Enzyme 2 column eluates were of qualitatively similar purity to process train drug substances, although some faint, very high molecular weight species bands were present in the affinity eluates. These bands were likely produced by exposure to the low pH elution and were consistent with the SEC-aggregation results.

3. Aggregates and Dimers

The aggregate and dimer levels of Enzyme 2 were determined within a single SEC-HPLC method (Table 1). The level of aggregate by SEC was slightly higher for the affinity column eluates compared to the Enzyme 2 drug substance

4. Glycosylation profiles

Figure 7:
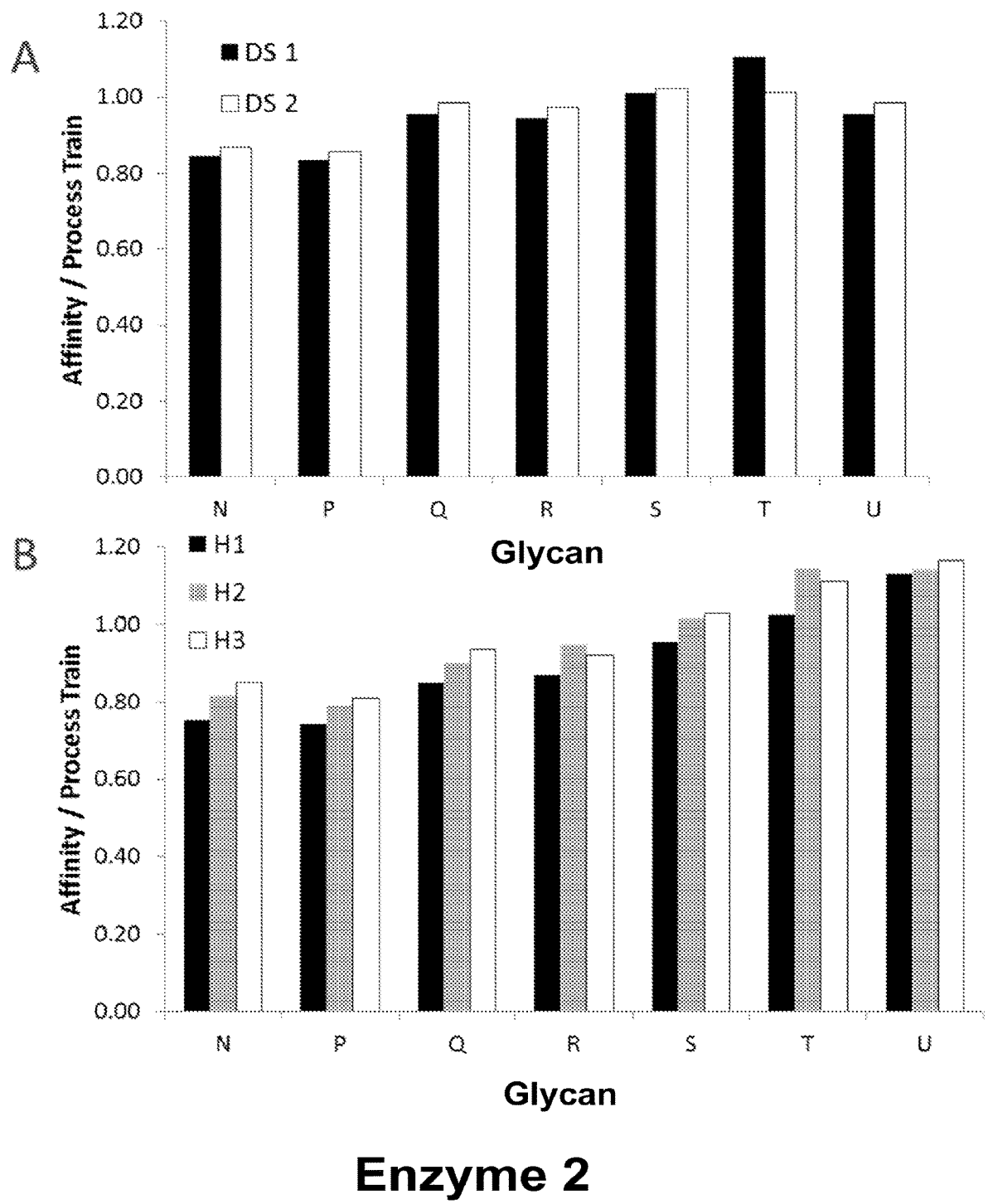
FIG. 7 shows glycosylation profiling data for the Enzyme 2 direct comparison study. Anti-enzyme 2 column eluate data (affinity) were divided by process train data for each glycan for either (A) drug substance or (B) harvest slice load materials.

Glycosylation profiles were also determined for the Enzyme 2 samples using the same method as for Enzyme 1. For the two drug substance loads (DS1 and DS2), the glycoprofile was measured both before and after processing on the anti-Enzyme 2 affinity column and, as before, the ratio of the affinity and process train results for each quantified glycan was calculated (FIG. 7A). The ratios were close to one for 6 of the glycans (Q-V) indicating that the relative abundances of these glycans were unchanged by the affinity column operation. The ratios for glycans N and P were slightly lower than one, indicating some potential loss of those glycans on the anti-Enzyme 2 column. Overall, the ratios were consistent between the two lots studied, though additional replicates would be necessary to further inform a model accounting for these differences.

Importantly, the results for the drug substance load material proved that the selected monoclonal antibody clone captured Enzyme 2 sub-populations with all of the quantified glycans. Whereas the use of polyclonal antibodies for the anti-Enzyme 1 column minimized the chance that entire glycans would be segregated due to the epitopic heterogeneity of the ligands, use of a monoclonal antibody was likely associated with additional risk of missing particular Enzyme 2 sub-populations depending on the location of the epitope on the target molecule. The results presented in FIG. 4A proved that the selected monoclonal antibody was suitable for continued study.

For the harvest slice loads, glycosylation comparisons were made between the affinity column eluate and corresponding multi-step, process train drug substances (FIG. 7B). The ratios varied between 0.75 and 1.15 and were consistent across the harvest slice lots studied. The ratios were lowest for glycans N and P (0.78 and 0.77, respectively). The results from the drug substance load experiments suggested that losses over the affinity column may account for much of the differences observed between the affinity eluate and process train drug substance for these two glycans. Because the ratios for remaining glycans were close to 1.0 in the drug substance load experiments (FIG. 4A), any deviations from 1.0 for the harvest slice results (FIG. 4B) can be attributed to segregation or enrichment of certain glycans by the process train. Relatedly, glycans T and U were, on average, present in 10% greater abundance in the affinity column eluate than in the process train drug substance. This result suggested potential loss of these glycans during the multi-step process. If such a trend persisted with increased replicates, further analyses of individual steps within the process train could be performed to pinpoint the segregating step(s). The affinity column would be most useful for purifying eluates early in the train to enable glycosylation analysis.

In addition to assessing the performance of the affinity column relative to the process train, the harvest loads studied also enabled analysis of harvest slices obtained at different stages of a single perfusion bioreactor campaign. The ability to perform such granular analyses is important due to the potential for non-steady state behavior.

Figure 8:
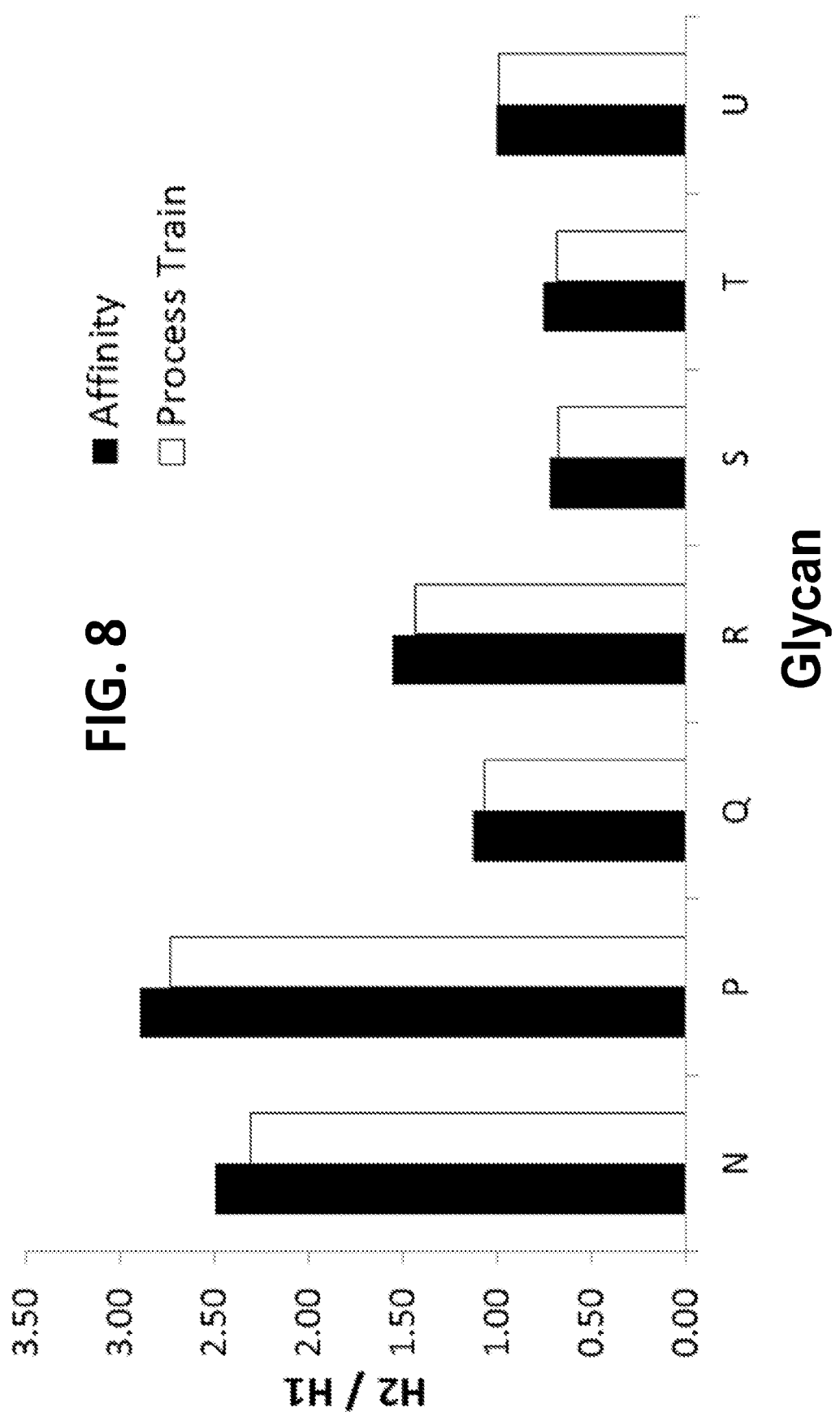
FIG. 8 shows ratio of glycosylation profile results for harvest slices H2 and H1 arranged according to purification strategy, either Anti-Enzyme 2 affinity (dark bars) or process train (light bars).

To quantify this behavior, the glycan results were normalized by the slice H1 data and presented separately for each purification strategy (FIG. 8). The glycosylation profiles were significantly different between harvest slices H1 and H2, increasing by a factor of 2-3 for glycans N and P, while decreasing over 30% for glycans S, T, and U. Most importantly, the magnitude of these harvest slice-dependent differences was highly consistent between the affinity and process train purification strategies.

This result demonstrated that the affinity column could capture the harvest day variability in a single-step process, instead of requiring the four step Enzyme 2 process train.

Example 5: Comparison of Affinity-Purified Products and Products Produced at Different Stages of a Multi-Step Bioprocess Six Enzyme 3 harvest lots and three different lots of Enzyme 3 drug substance samples were studied for direct comparison. Pre- and post-column product quality was evaluated for the drug substance loads to determine any changes in CQAs during the affinity column operation. By studying harvest and drug substance loads, the source of any observed differences during the direct comparisons could be properly ascribed to biases introduced by either the affinity column, multi-step process train, or both operations.

1. Purity and Specific Activity

The purification process indicators for Enzyme 3 were recovery and purity. Column recoveries were slightly lower than the 70% obtained during initial method development, ranging between 60-70%, but were still considered acceptable. For clarified cell culture harvest loads, purity testing by silver-stained SDS-PAGE indicated qualitatively comparable purity for the two purification techniques (data not shown). Specific activity, aggregation, dimer content, peptide mapping, and N-linked glycosylation profile were the critical quality attributes evaluated during the direct comparison study.

Figure 9:
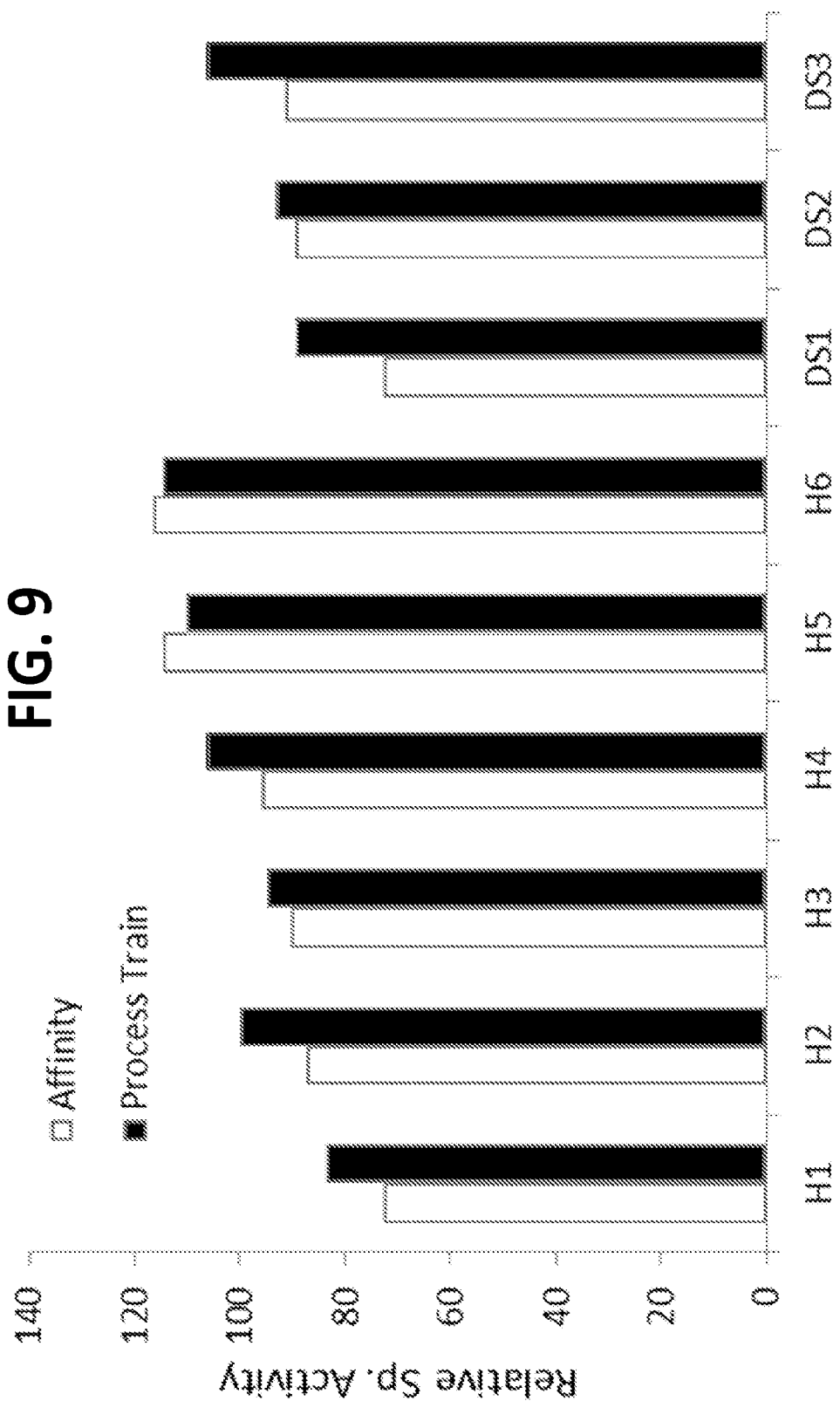
FIG. 9 shows a direct comparison of specific activity of Enzyme 3 product purified either using the affinity techniques or the multi-step process train. All specific activity data were normalized to the drug substance historical average.

Specific activity was determined for the affinity and process train purified Enzyme 3 (FIG. 9). The affinity purified specific activity was 94%±7% (mean±S.D) of that for the process train across the 6 harvest lots. The specific activity decrease was also observed for drug substance loads (88%±7% of drug substance load), suggesting that the slight decrease was most likely due to partial Enzyme 3 inactivation by the low pH affinity column elution condition.

2. Aggregation and Dimers

Figure 10:
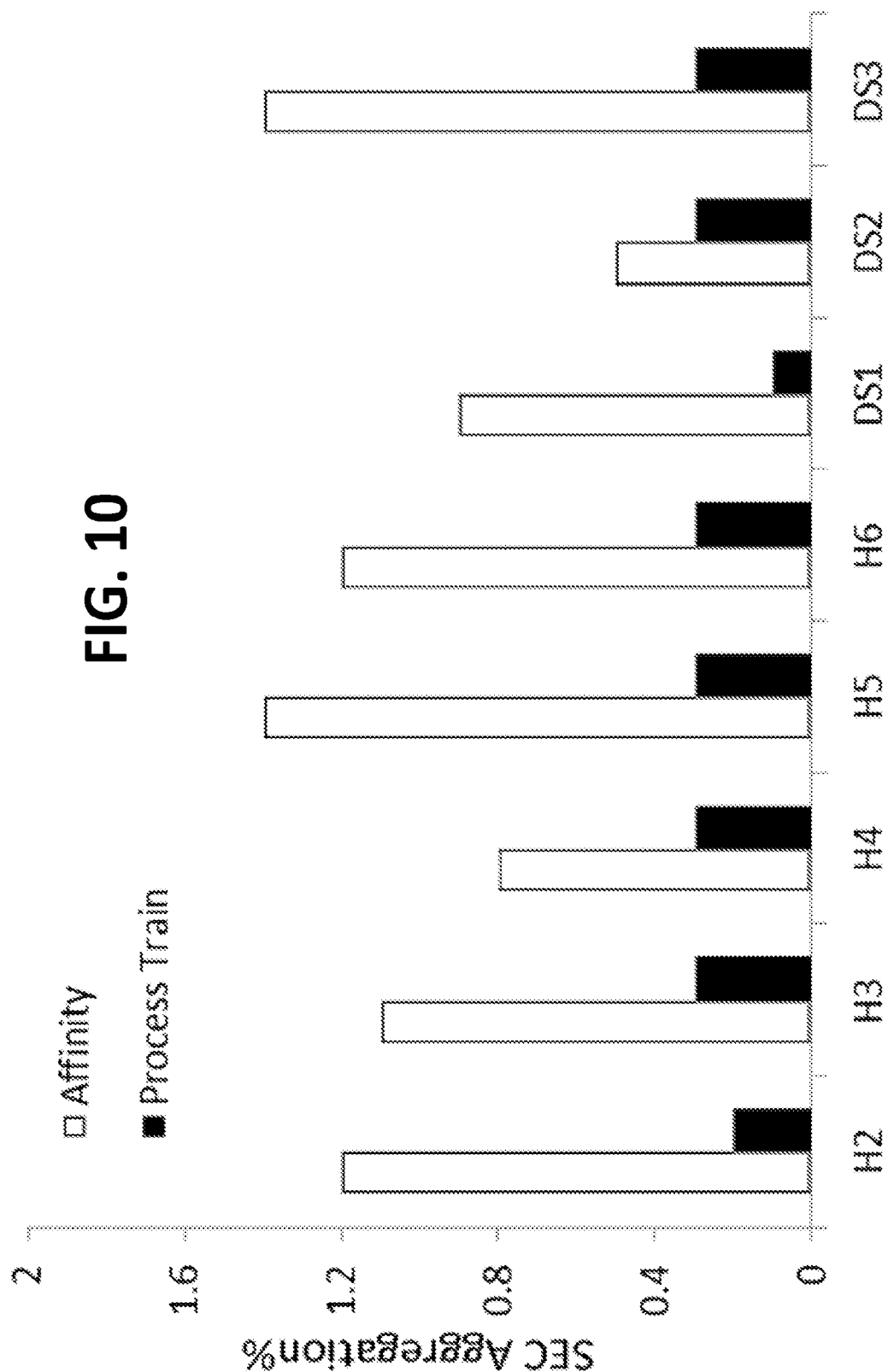
FIG. 10 shows a direct comparison of SEC-aggregation of Enzyme 3 product purified either using the affinity techniques or the multi-step process train.

The aggregation determined by SEC was also slightly higher for the affinity column eluates (0.5-1.4% versus 0.1-0.3%, respectively) (FIG. 10). This aggregation level remains well below any level that would interfere with CQA measurement. These slightly higher aggregate levels are likely due to the low pH elution conditions in the anti-Enzyme 3 process.

Figure 11:
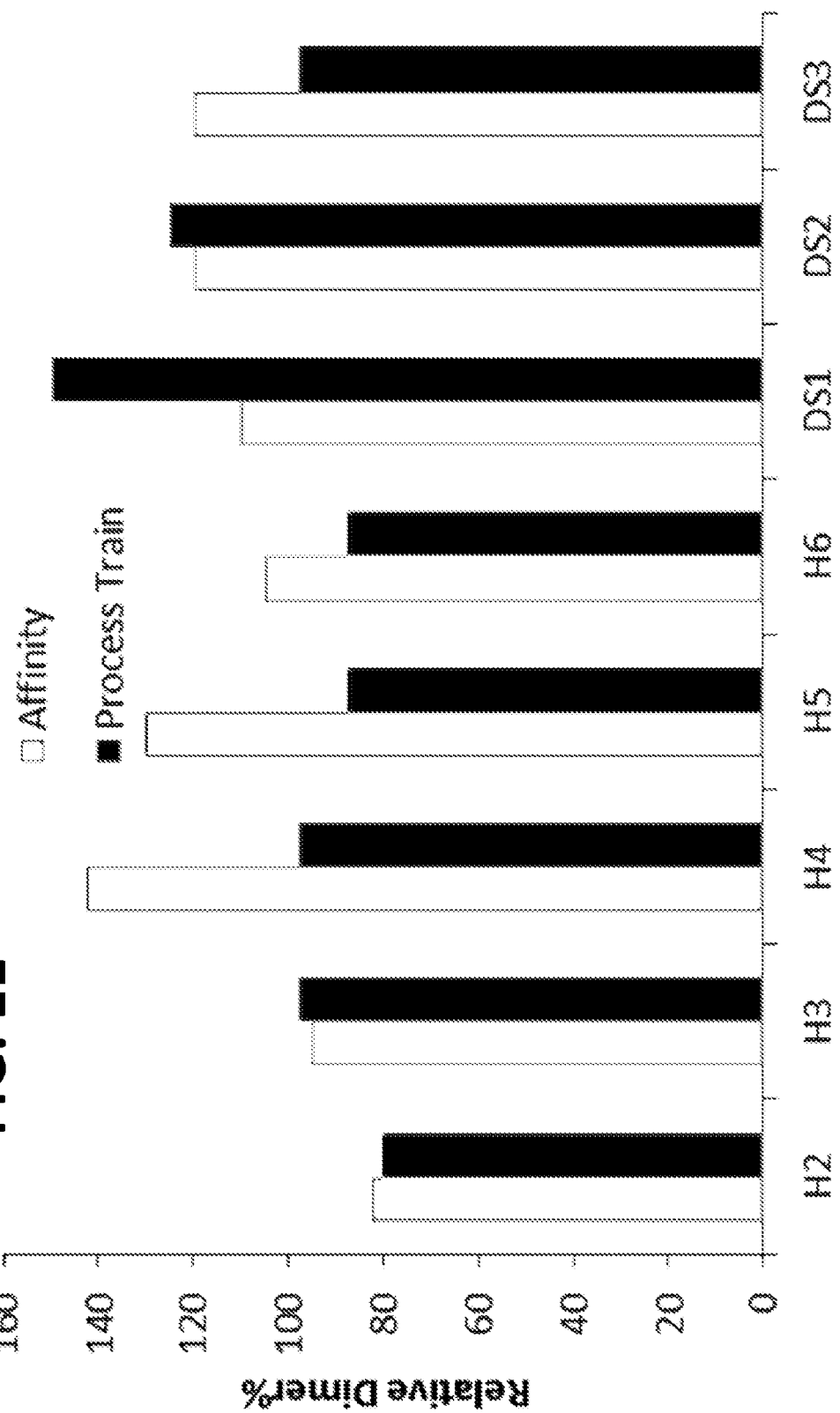
FIG. 11 shows a direct comparison of SEC-dimers found in Enzyme 3 product purified either using the affinity techniques or the multi-step process train. All dimer data were normalized to the drug substance historical average.

SEC-dimer results were compared to those of the process train drug substance (FIG. 11). Although no clear trend is visible it is clear that the affinity column is able to capture dimer from different slices of harvest material.

3. Glycosylation Profiles

Direct comparisons of N-glycan species (glycostructures), were performed for Enzyme 3 obtained from the two purification methods by AA labeling assay. These comparisons revealed significant but consistent differences in the relative abundances of some N-glycans. To quantify these differences, ratio model formalism was selected for simplicity. A ratio was calculated for each glycan dividing the result (relative peak area) for the affinity eluate by that for the process train. A ratio of one would indicate a comparable result for the two purifications, while a ratio greater than one indicates greater relative abundance of that particular glycan in the affinity eluate.

Figure 12:
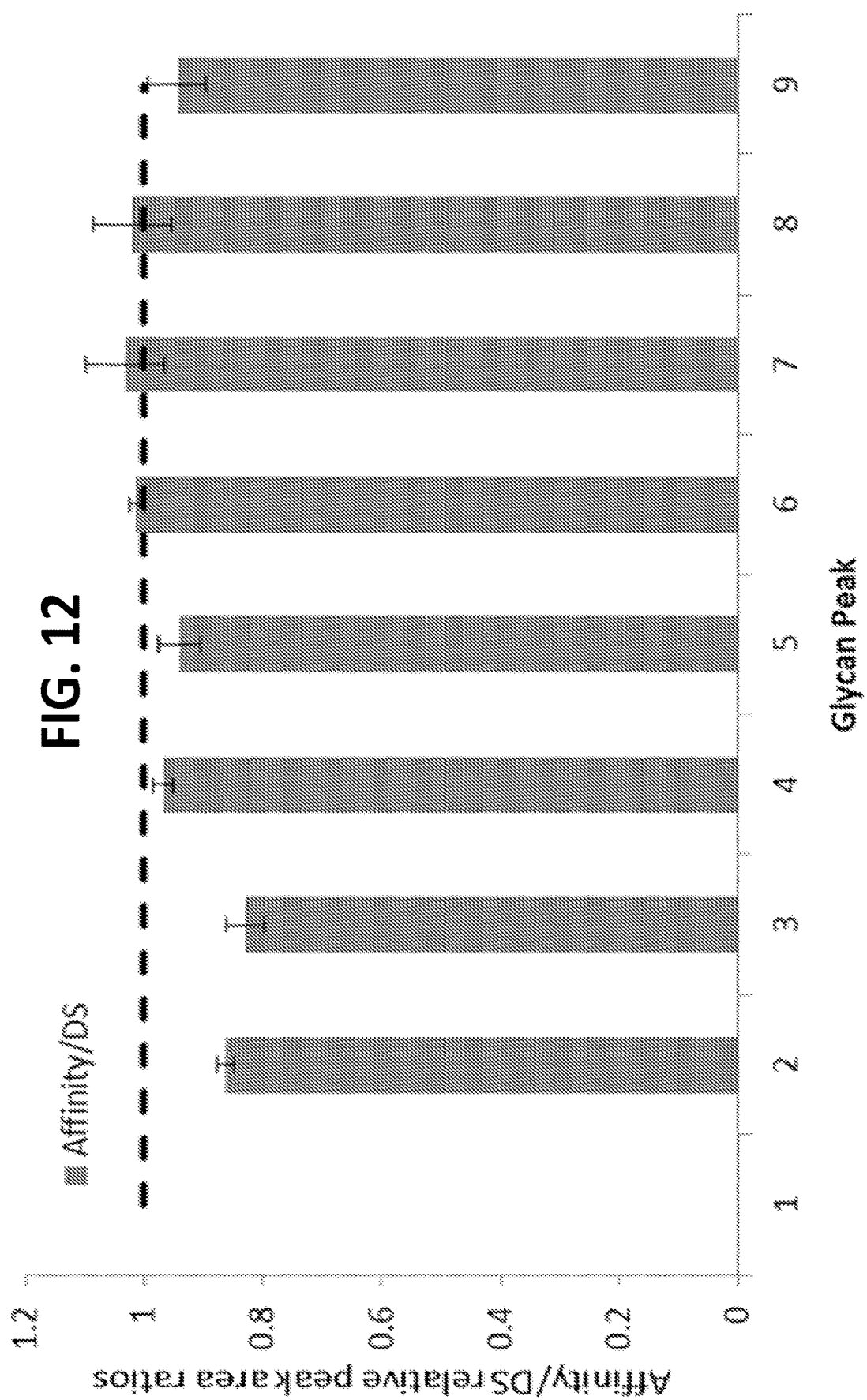
FIG. 12 shows a comparison of the glycosylation profiles of Enzyme 3 drug substance loads as measured both before and after processing using affinity techniques. Data is presented as a ratio calculated for each glycan dividing the result (relative peak area) for the affinity eluate by that for the corresponding drug substance load.

Glycosylation profiles were measured for drug substance loads both before and after processing on the affinity column and a ratio of the results was calculated for selected glycostructures (FIG. 12). The ratios were close to one for 6 of the N-glycans (peaks 4-9) indicating no change in relative abundances during affinity column processing. The ratios for glycans peak 2 and 3 were slightly lower than one, indicating potential loss on the affinity column. The ratios were consistent between the three drug substance lots. Interestingly, glycans peak 2 and 3 are the only two neutral glycans quantitated in the AA labeling assay, differing in structure only by the presence or absence of a fucose residue. Importantly, the results proved that the selected monoclonal antibody clone captured all quantified Enzyme 3 glycostructures and, for all but two glycans, in the same relative abundance as was measured in the load. The ratio standard deviations were s 0.07 for all glycans indicating robust method reproducibility.

Figure 13:
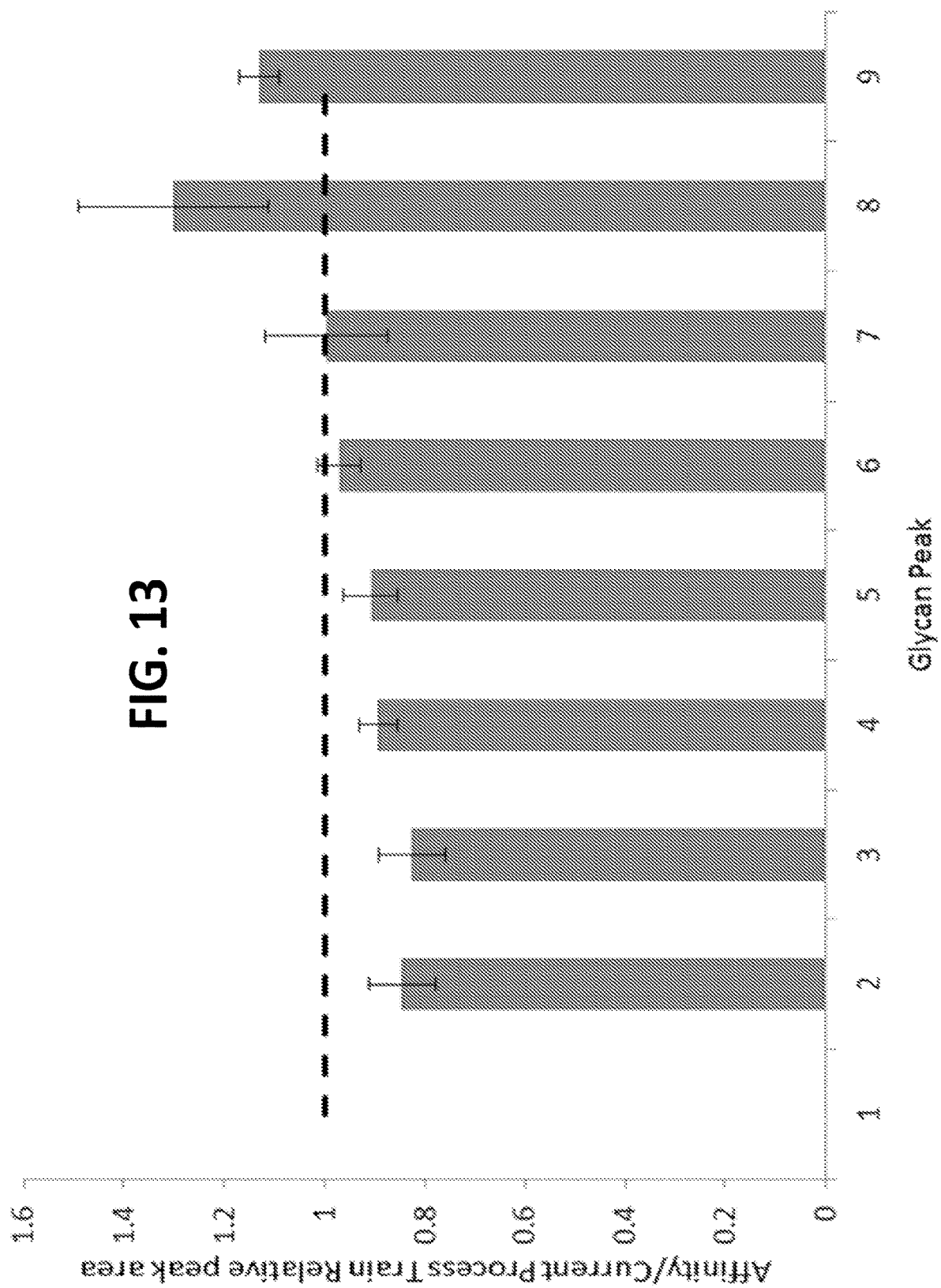
FIG. 13 shows a comparison of the glycosylation profiles of Enzyme 3 harvest loads purified using affinity techniques. Data is presented as a ratio calculated for each glycan dividing the result (relative peak area) for the affinity eluate by that for the multi-step purified enzyme product.

For the cell culture harvest loads, glycosylation comparisons were made between the affinity column and multi-step process train techniques (FIG. 13). The ratios varied between about 0.75 and just above 1.0, and were consistent across the six harvest lots studied (SD≤0.12). (FIG. 13). The ratios were lowest for glycans peak 2 and 3 (0.85 and 0.83, respectively); however, the results from the drug substance load experiments suggested that losses over the affinity column may account for much of the observed difference between the affinity and process train results for these particular glycostructures. Conversely, because the ratios for remaining glycostructures were close to 1.0 in the drug substance load experiments (FIG. 12), any deviations from 1 for the harvest load results (FIG. 13) were likely attributable to segregation or enrichment by the process train. For example, peak 9, on average, is present in 10% greater abundance in the affinity eluates, suggesting potential losses of this glycostructure during the multi-step process: whereas similar peak 6 ratio for harvest and DS loads indicates that the peak 6 glycan is unaffected by either purifications.

4. Development of Predictive Models

Mathematical predictive models were developed to account for the observed product quality differences between the two purification techniques. For example, although there was a slight decrease in specific activity, the extent of inactivation was relatively consistent as indicated by the low standard deviation (7%), which is a requirement to build a reliable and predictive model. A linear ratio transformation, such as simply dividing affinity purified specific activities by 0.94, could be used to transform affinity eluate data to that which have been obtained by the multi-step process train (see FIG. 1 and description above). As a result, the anti-Enzyme 3 affinity column can be used in place of a multi-step process train to analyze Enzyme 3 specific activity in cell culture harvest.

Specific activity for a drug substance, such as a non-antibody protein like Enzyme 3, can be predicted from affinity specific activity using the following relation:

$$DS \text{ specific } acitivity = \frac{\text{Affinity Specific Activity}}{0.94 \pm 0.07}$$

A predictive model was developed for Enzyme 3 dimer content. Although the high standard deviation (24%) prevents the model from detecting some differences between affinity eluate and process train Enzyme 3 drug substance. Dimer content in the drug substance can be predicted from affinity dimer % using the following relation:

$$DS \text{ Dimer } \% = \frac{\text{Affinity Dimer } \%}{1.23 \pm 0.24}$$

A similar strategy was also applied to develop predictive models for individual Enzyme 3 glycostructures. For example, the ratio for glycan peak 9, 1.13±0.04, can be used to transform an affinity column result (by dividing by 1.13) to provide the glycan peak 9 result that would have been obtained by execution of the multi-step process train. The transformation ratios for each Enzyme 3 glycostructure were determined by combining the data for all six lots tested (FIG. 13). The standard deviation of the applied ratios was low (between 0.04 and 0.12 for all but one glycan).

It should also be noted that the starting material used to execute the direct comparison study and to build the models was specifically selected to encompass a range of anticipated Enzyme 3 product quality, including glycosylation.

By applying these predictive models, the affinity column can provide drug substance-equivalent product quality data without the multi-step process train.

$$DS \text{ Peak } \% = \frac{\text{Affinity Peak } \%}{X peak}$$

Overall, the Enzyme 3 predictive models showed nearly complete agreement between the product quality of the affinity and process train purified materials.

Example 6. Monitoring Product Quality Throughout a Multi-Step Purification Process One of the most impactful features of the single-step affinity methodology is that it provides the ability to monitor product quality throughout the duration of a bioprocess.

In this example, the single-step affinity column methodology as disclosed was used to purify drug substance Enzyme 4, a biotherapeutic enzyme. Purification of Enzyme 4 was conducted using a bioreactor process that was sampled at different days across the harvest period. Critical quality attributes (CQA) designated CQA 1, CQA2, and CQA3 were measured as a function of the harvest duration. Without the single-step affinity column, this level of granularity would not have been attained due to the significant downstream resources required to execute multi-step purification processes for all required time points. Moreover, because only a single purification step is required, the sample volumes necessary to execute the downstream process were minimal, which led to (1) minimal disruption of the bioreactor process due to over-sampling, and (2) maximum time-based resolution (snapshots) of product quality since large harvest pools were not required.

Figure 14:
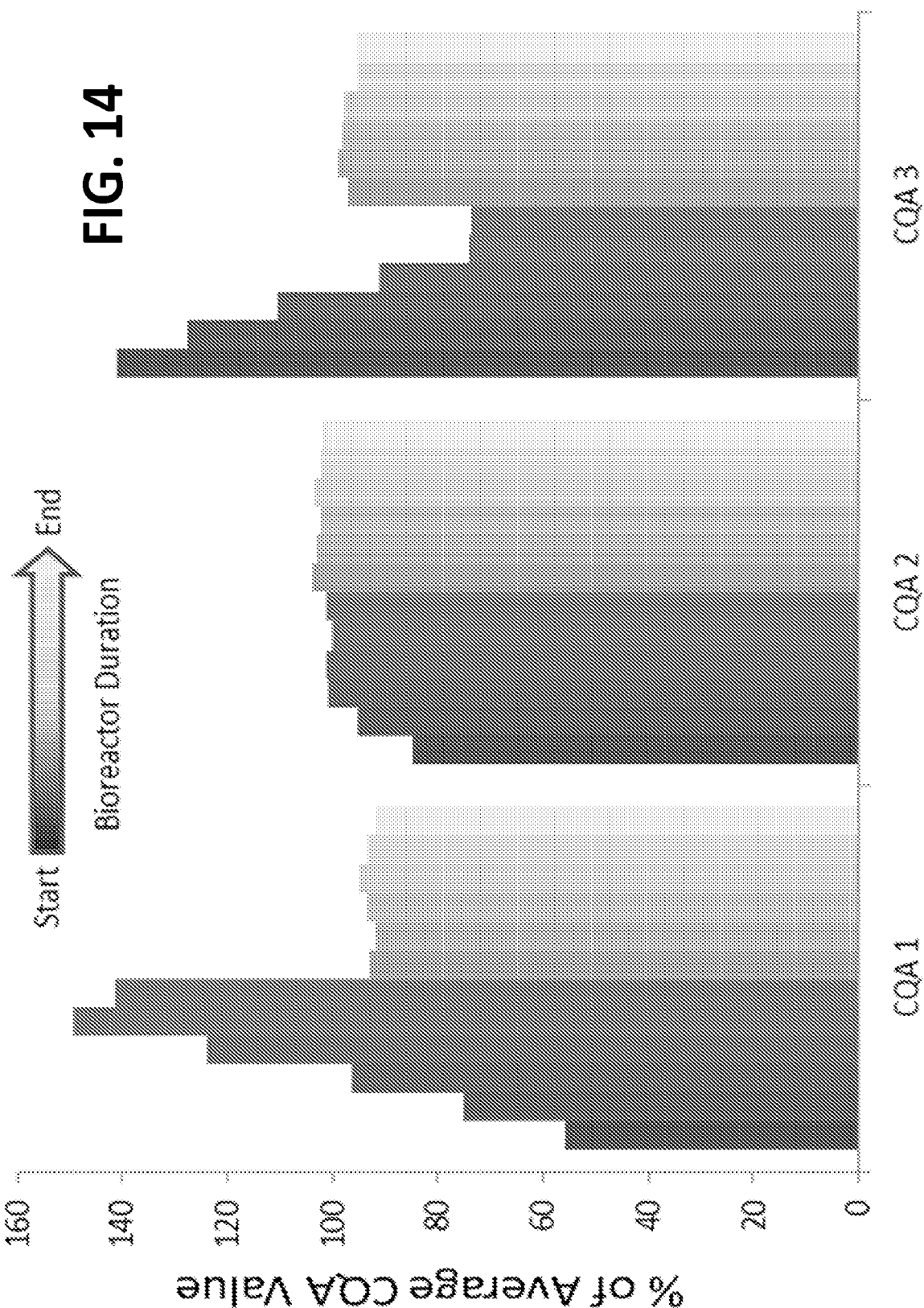
FIG. 14 shows product quality data obtained using the single-step affinity methodology for critical attributes (CQAs) 1, 2, and 3 as a function of harvest duration in a bioreactor.

As shown in FIG. 14, the product quality results for Enzyme 4 indicated significant transience for both CQAs 1 and 3 in the earlier stages of the bioreactor run with a steadier product quality profile in the later stages. CQA 2 was observed to be relatively steady throughout the course of the run.

This product quality information enables process decision-making based on product quality. For example, based on these results from Enzyme 4, the development scientist could choose to study alternative bioreactor control strategies in the early stages of the bioreactor process in order to minimize product quality variations in the process.

Example 7. Analysis of Individual Steps in a Multi-Step Purification Process

Another major application of the single step affinity methodology is for analysis of a downstream purification process and its effect on product quality. In some applications, the technology is most useful for the earliest steps in a purification process, such as clarification, capture chromatography, and intermediate chromatography, where the product purity level is generally lower and requires further purification (FIG. 2).

In this example, an affinity column prepared as described above was used to purify samples of drug substance Enzyme 5 that were obtained at five stages of a multi-step purification process. The glycosylation profile was analyzed for each affinity-purified Enzyme 5 sample. The results for several glycans were normalized to the results obtained for the Enzyme 5 product produced using the multi-step bioprocess (e.g., after step 5).

Figure 15:
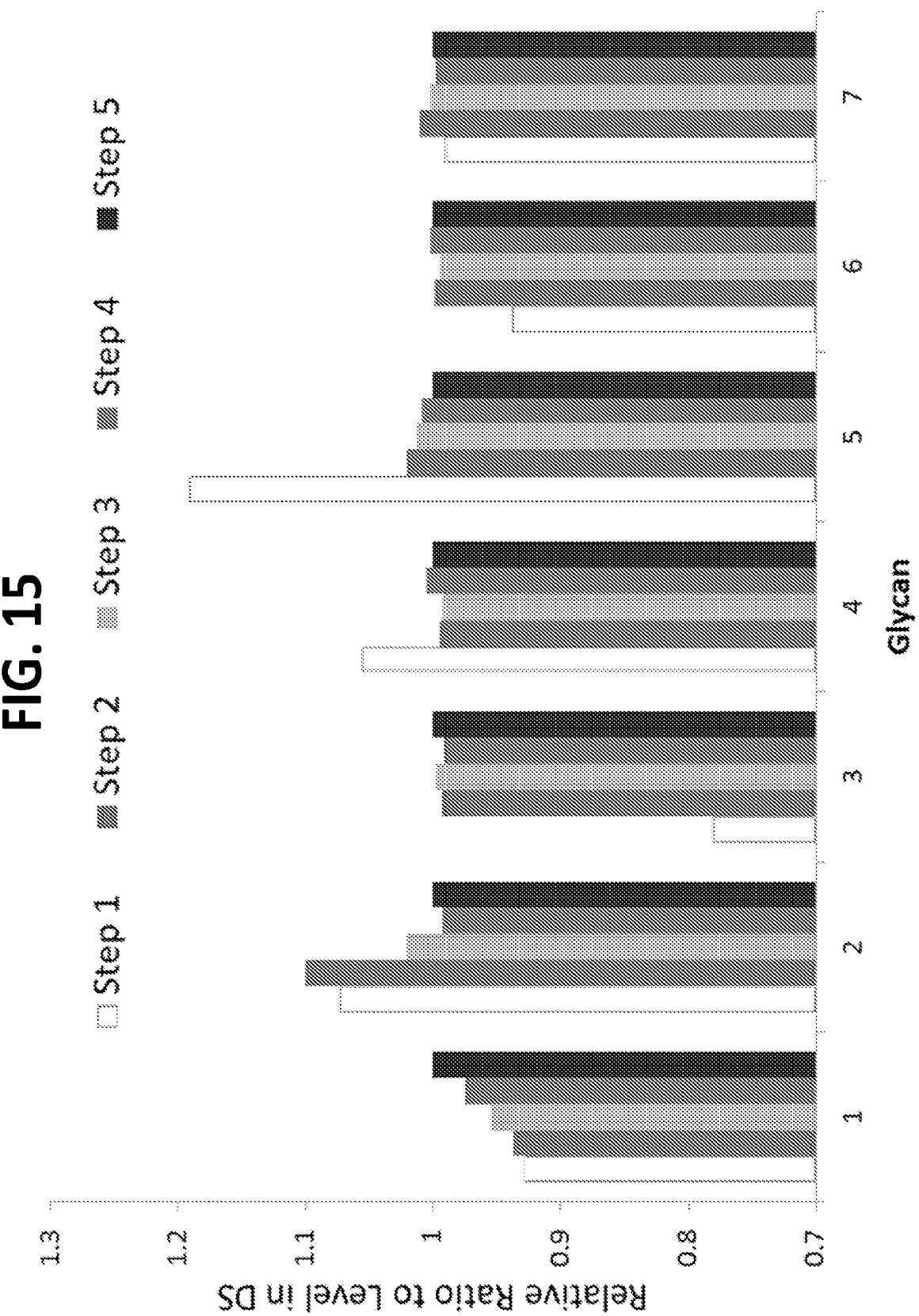
FIG. 15 shows a glycosylation analysis of a downstream purification process of a biotherapeutic enzyme. Results for selected glycans at five steps in the process are presented as a relative ratio to their final level at drug substance (DS). The relative ratio is equal to one at the final step since this is the DS stage.

The results of these glycosylation profile analyses are provided in FIG. 15. From these data, it is clear that significant changes to the relative distribution of glycans 3 and 5 occurred during processing on downstream step 2, with approximately 20% enrichment or loss, respectively. Additionally, an approximately 10% loss of glycan 2 was observed during downstream step 3. Finally, the relative quantity of glycan 7 was unchanged throughout downstream purification.

These similarities or differences would be otherwise unobservable without the affinity column technology due to the low product purity at this stage in the process. Depending on the relative importance of the particular glycan to the safety or efficacy of the biotherapeutic, a particular process step could be re-developed or optimized to avoid (or promote) any observed losses.

BIBLIOGRAPHY

[1] Callis, J. B., Illman, D. L., Kowalski, B. R., Process Analytical. *Analytical Chemistry* 1987, 59, 624A-637A.
[2] Lopes. J. A., Costa, P. F., Alves, T. P., Menezes. J. C., Chemometrics in bioprocess engineering: Process analytical technology (PAT) applications. *Chemometrics and Intelligent Laboratory Systems* 2004, 74, 269-275.

[3] Rathore, A. S., Bhambure, R., Ghare, V., Process analytical technology (PAT) for biopharmaceutical products. *Anal Bioanal Chem* 2010, 398, 137-154.

[4] Zandian, M., Jungbauer, A., An immunoaffinity column with a monoclonal antibody as ligand for human follicle stimulating hormone. *J Sep Sci* 2009, 32, 1585-1591.

[5] Hossler, P., Khattak, S. F., Li. Z. J., Optimal and consistent protein glycosylation in mammalian cell culture. *Glycobiology* 2009, 19, 936-949.

[6] Hirschfeld, T., Callis, J. B., Kowalski, B. R., Chemical sensing in process analysis. *Science* 1984, 226, 312-318.

[7] Read, E. K., Shah, R. B., Riley, B. S., Park, J. T., et al., Process analytical technology (PAT) for biopharmaceutical products: Part H. Concepts and applications. *Biotechnol Bioeng* 2010, 105, 285-295.

[8] Kourti, T., The Process Analytical Technology initiative and multivariate process analysis, monitoring and control. *Analytical and bioanalytical chemistry* 2006, 384, 1043-1048.

[9] Kuribayashi, R., Hashii, N., Harazono. A., Kawasaki, N., Rapid evaluation for heterogencitics in monoclonal antibodies by liquid chromatography/mass spectrometry with a column-switching system. *J Pharm Biomed Anal* 2012, 67-68, 1-9.

[10] Wang, Y., Wu, S. L., Hancock, W. S., Monitoring of glycoprotein products in cell culture lysates using lectin affinity chromatography and capillary HPLC coupled to electrospray linear ion trap-Fourier transform mass spectrometry (LTQ/FTMS). *Biotechnology progress* 2006, 22, 873-880.

[11] Teixeira. A. P., Oliveira, R., Alves, P. M., Carrondo. M. J., Advances in on-line monitoring and control of mammalian cell cultures: Supporting the PAT initiative. *Biotechnol Adv* 2009, 27, 726-732.

[12] Chon, J. H., Zarbis-Papastoitsis, G., Advances in the production and downstream processing of antibodies. *New Biotechnology* 2011, 28, 458-463.

[13] Kelley. B., Very large scale monoclonal antibody purification: The case for conventional unit operations. *Biotechnology progress* 2007, 23, 995-1008.

[14] Le Floch, F., Tessier, B., Chenuet, S., Guillaume, J. M., et al., HPCE monitoring of the N-glycosylation pattern and sialylation of murine erythropoietin produced by CHO cells in batch processes. *Biotechnology progress* 2004, 20, 864-871.

[15] Weber, W., Bertics, P. J., Gill, G. N., Immunoaffinity purification of the epidermal growth factor receptor. Stoichiometry of binding and kinetics of self-phosphorylation. *J Biol Chem* 1984, 259, 14631-14636.

[16] Thompson, N. E., Hager, D. A., Burgess, R. R., Isolation and characterization of a polyol-responsive monoclonal antibody useful for gentle purification of *Escherichia coli* RNA polymerase. *Biochemistry* 1992, 31, 7003-7008.

[17] Burgess, R. R., Thompson, N. E., Advances in gentle immunoaffinity chromatography. *Curr Opin Blotechnol* 2002, 13, 304-308.

[18] Thompson, N. E., Burgess, R. R., Purification of recombinant human transcription factor ITTB by immunoaffinity chromatography. *Protein Expr Purif* 1994, 5, 468-475.

[19] Berry, M. J., Davies, J., Smith. C. G., Smith, I., Immobilization of Fv antibody fragments on porous silica and their utility in affinity chromatography. *J Chromatogr* 1991, 587, 161-169.

[20] Harmsen, M. M., De Haard, H. J., Properties, production, and applications of camelid single-domain antibody fragments. *Appl Microbiol Biotechnol* 2007, 77, 13-22.

[21] Walter, J. G., Stahl, F., Scheper. T., Aptamers as affinity ligands for downstream processing. *Engineering in Life Sciences* 2012, 12, 496-506.

[22] Romig. T. S., Bell. C., Drolet, D. W., Aptamer affinity chromatography: combinatorial chemistry applied to protein purification. *J Chromatogr B Biomed Sci Appl* 1999, 731, 275-284.

[23] Naik, A. D., Menegatti, S., Gurgel, P. V., Carbonell, R. G., Performance of hexamer peptide ligands for affinity purification of immunoglobulin G from commercial cell culture media. *J. Chromatogr A* 2011, 1218, 1691-1700.

[24] Yang, Z., Hancock, W. S., Monitoring glycosylation pattern changes of glycoproteins using multi-lectin affinity chromatography. *J Chromatogr A* 2005, 1070, 57-64.

The invention claimed is:

1. A method of developing a multi-step bioprocess for producing a non-antibody protein (NAP), the method comprising:

a) processing a NAP comprising an engineered protein or enzyme using a particular bioprocess unit operation within the multi-step bioprocess;

b) purifying the NAP from solution within the multi-step bioprocess by:

i) contacting a heterogeneous solution comprising the NAP with an affinity construct comprising a solid support coupled to an affinity ligand that binds the NAP, ii) isolating the affinity-purified NAP from the heterogeneous solution, and iii) determining a critical quality attribute (CQA) of the affinity-purified NAP, wherein the CQA is a physical, chemical, biological, or microbiological property or characteristic of the NAP selected from the group consisting of product purity, potency, charged isoform profile, post-translational modifications, oxidation, reductions, deamidation, adduct formation, clipped forms, enzymatic cleavage, specific activity, peptide map, dimer content, product aggregation, site specific glycosylation, total glycans, and glycosylation profile;

c) providing a transformed CQA of the affinity-purified NAP by calculating a ratio of the determined CQA of the affinity-purified NAP to a determined CQA of the NAP purified by a multi-step process train purification; and d) developing the multi-step bioprocess by modifying the particular bioprocess unit operation based on the transformed CQA.

2. The method of claim 1, wherein the bioprocess unit operation is a bioreactor process, seed train, capture chromatography, intermediate chromatography, filtration, centrifugation, precipitation, flocculation, UV irradiation, or viral inactivation.

3. The method of claim 1, wherein the transformed CQA of the affinity-purified NAP is equivalent to the NAP produced by a bioprocess unit operation within the multi-step bioprocess.

4. The method of claim 1, wherein the CQA of the NAP is determined at the following stages within the multi-step bioprocess:

a) immediately upstream of a particular bioprocess unit operation;

b) immediately downstream of the particular bioprocess unit operation;

c) both upstream and downstream of a particular bioprocess unit operation, or d) within a particular bioprocess unit operation at one or more timepoints.

5. The method of claim 1, wherein the CQA of the NAP is determined at one or more timepoints within the multi-step bioprocess.

6. The method of claim 1, wherein the bioprocess is selected from the group consisting of continuous, semi-continuous, and batch.

7. The method of claim 6, wherein the CQA is measured using a high-throughput or rapid analytical technique.

8. The method of claim 7, wherein the analytical technique is high-performance liquid chromatography, differential refractometry, fluorescence, ultra-performance liquid chromatography, multi-angle laser light scattering analysis, mass spectroscopy, tandem mass spectroscopy, isoelectric focusing, or differential scanning calorimetry.

9. The method of claim 1, wherein the NAP is a biotherapeutic drug substance or a commercial biologic.

10. The method of claim 1, wherein the multi-step bioprocess for the NAP is a commercial or manufacturing process.

11. The method of claim 1, wherein one or more purification steps are performed by a robot.

12. The method of claim 1, wherein the ligand of the affinity ligand-coupled based solid support is an antibody.

13. The method of claim 1, wherein the affinity construct is integrated with the bioprocess in a manner selected from the group consisting of at-line mode, offline mode, and in-line mode.

14. The method of claim 1, wherein the affinity construct comprises a parameter that is optimized to maximize the quality or purity of the affinity-purified NAP.

* * * * *